(12) United States Patent
Iwai et al.

(10) Patent No.: US 9,944,958 B2
(45) Date of Patent: Apr. 17, 2018

(54) METHOD FOR PREPARING TRIACYLGLYCEROL HIGH-PRODUCTIVITY ALGAE

(71) Applicant: TOKYO INSTITUTE OF TECHNOLOGY, Tokyo (JP)

(72) Inventors: Masako Iwai, Tokyo (JP); Hiroyuki Ohta, Tokyo (JP); Mie Shimojima, Tokyo (JP)

(73) Assignee: TOKYO INSTITUTE OF TECHNOLOGY, Tokyo (JP)

( * ) Notice: Subject to any disclaimer, the term of this patent is extended or adjusted under 35 U.S.C. 154(b) by 0 days.

(21) Appl. No.: 15/125,485

(22) PCT Filed: Mar. 12, 2015

(86) PCT No.: PCT/JP2015/057302
§ 371 (c)(1),
(2) Date: Sep. 12, 2016

(87) PCT Pub. No.: WO2015/137449
PCT Pub. Date: Sep. 17, 2015

(65) Prior Publication Data
US 2017/0073711 A1 Mar. 16, 2017

(30) Foreign Application Priority Data
Mar. 13, 2014 (JP) ................. 2014-049651

(51) Int. Cl.
*C12N 1/12* (2006.01)
*C12P 7/64* (2006.01)
*C12N 15/82* (2006.01)
*C12N 9/10* (2006.01)

(52) U.S. Cl.
CPC .............. *C12P 7/64* (2013.01); *C12N 9/1029* (2013.01); *C12N 15/8237* (2013.01); *C12N 15/8247* (2013.01); *C12P 7/6463* (2013.01); *C12Y 203/01085* (2013.01)

(58) Field of Classification Search
CPC ........ C12N 15/8247; C12N 15/09; C12P 7/64
USPC ................................. 435/257.1, 232
See application file for complete search history.

(56) References Cited

U.S. PATENT DOCUMENTS

| 5,922,564 A | 7/1999 | Lefebvre et al. |
| 2016/0244772 A1 | 8/2016 | Ohta et al. |

FOREIGN PATENT DOCUMENTS

| JP | 2001-512977 A | 8/2001 |
| JP | 2012-7146 A | 1/2012 |
| JP | 2014-68638 A | 4/2014 |
| WO | WO 2011/156520 A2 | 12/2011 |
| WO | WO 2015/029997 A1 | 3/2015 |

OTHER PUBLICATIONS

Yu et al. [PNAS, Apr. 16 2002, 99(8): 5732-5737].*
Cakmak Z. E. et al., "Induction of triacylglycerol production in Chlamydomonas reinhardtii: Comparative analysis of different element regimes", Bioresource Technolology, vol. 155, 2014, pp. 379-387.
International Search Report for PCT/JP2015/057302 (PCT/ISA/210) dated Jun. 16, 2015.
Iwai et al., "Ryokuso Chlamydomonas reinhardtii ni Okeru Rin Ketsubo Otosei Promoter o Mochiita Shishitsu Chikuseki Kyoka", Proceedings of the 55th Annual Meeting of the Japanese Society of Plant Physiologists, vol. 55, Apr. 11, 2014, p. 362.
Iwai et al., "Ryokuso Chlamydomonas reinhardtii Yurai no Rin Ketsubo Otosei Promoter o Mochiita Shishitsu Chikuseki Kyoka", Proceedings of the 56th Annual Meeting of the Japanese Society of Plant Physiologists, vol. 56, Mar. 9, 2015, p. 129.
Iwai et al., "Sorui ni Okeru Rin Ketsubo Otosei Promoter o Mochiita Shishitsu Chikuseki Kyoka", Proceedings of the 78th Annual Meeting of the Botanical Society of Japan, vol. 78th, Sep. 1, 2014, p. 162.
Iwai M. et al., "Enhancement of extraplastidic oil synthesis in Chlamydomonas reinhardtii using a type-2 diacylglycerol acyltransferase with a phosphorus starvation-inducible promoter", Plant Biotechnology Journal, vol. 12, 2014, pp. 808-819.
La Russa M. et al., "Functional analysis of three type-2 DGAT homologue genes for triacylglycerol production in the green microalga Chlamydomonas reinhardtii", Jounal of Biotechnology, vol. 162, 2012, pp. 13-20.
Written Opinion of the International Searching Authority for for PCT/JP2015/057302 (PCT/ISA/237) dated Jun. 16, 2015.
English translation of the International Preliminary Report on Patentability and Written Opinion of the International Searching Authority (Forms PCT/IB/338, PCT/IB/373 and PCT/ISA/237) dated Sep. 22, 2016, for International Application No. PCT/JP2015/057302.

* cited by examiner

*Primary Examiner* — Tekchand Saidha
(74) *Attorney, Agent, or Firm* — Birch, Stewart, Kolasch & Birch, LLP

(57) ABSTRACT

The purpose of the present invention is to effectively accumulate triacylglycerol in algae cells, the present invention providing a method for introducing a triacylglycerol synthetase gene, a phosphorus starvation-inducible promoter, and a 3' untranslated region into algae.

15 Claims, 9 Drawing Sheets

N. 2145

All were cultured for 8 days
red: chloroplast
green: neutral lipid

C. reinhardtii
Bars = 10 μm

METHOD FOR PREPARING TRIACYLGLYCEROL HIGH-PRODUCTIVITY ALGAE

TECHNICAL FIELD

The present invention relates to a method for preparing triacylglycerol (hereinafter referred to as "TAG") high-productivity algae, the TAG high-productivity algae, and a method for producing TAG using said algae.

BACKGROUND ART

Accumulating TAG in cells has been previously performed by introducing a TAG synthase gene into algae such as *Chlamydomonas reinhardtii* (hereinafter sometimes referred to as "*C. reinhardtii*") (Patent Literature 1, non-Patent Literature 1).

For example, non-Patent Literature 1 describes a method comprising introducing DGAT2 gene linked to a strong expression promoter of psaD into *C. reinhardtii*, culturing this under nitrogen or sulfur starvation conditions, and accumulating the TAGs in cells. Patent Literature 1 also describes *C. reinhardtii* into which DGAT2 gene linked to psaD was introduced, as is the case with non-Patent Literature 1.

With regard to producing TAGs, algae belonging to *Nannochloropsis* as well as *C. reinhardtii* have been attracting attention. The algae can be cultured at about 100 times higher density than *C. reinhardtii*, so it is assumed that they are more suitable for producing TAGs than *C. reinhardtii*.

Patent Literature

Patent Literature 1
WO 2011/156520

Non-Patent Literature

Non-Patent Literature 1
M. La Russa et al., J. Biotechnol. 2012 Nov. 30; 162(1):13-20

DISCLOSURE OF INVENTION

Technical Problem

As described above, a method for accumulating TAGs in cells by introducing a TAG synthase gene into algae has already known, but a sufficient amount of TAGs could not be accumulated by these methods. For example, non-Patent Literature 1 discloses that there was no statistically significant difference in the accumulated amount of TAGs between a DGAT2 transgenic strain and a wild-type strain under either nitrogen or sulfur starvation conditions (FIG. 5 and the like).

Under these circumstances, the object of the present invention is to provide a means for efficiently accumulating TAGs in cells of algae.

Solution to Problem

The present inventors have first presumed that it is due to a promoter that the sufficient amount of TAGs is not accumulated by the conventional methods. Specifically, the present inventors have presumed that a strong expression promoter such as psaD does not sufficiently function during nutrient starvation though TAGs are accumulated under such nutrient starvation conditions. Thus, the present inventors have obtained an idea of using a nutrient starvation-inducible promoter instead of a strong expression promoter. Further, the present inventors have examined accumulated amount of TAGs and fatty acid composition of TAGs under nitrogen starvation conditions and phosphorus starvation conditions. As a result, it has been found 1) that the accumulated amount of TAG under phosphorus starvation conditions was larger than that under nitrogen starvation conditions when vigorously proliferating cells were subcultured; 2) that under nitrogen starvation conditions, the amount of TAGs containing fatty acids derived from membrane lipids of chloroplast was large and the amount of newly synthesized fatty acids was small; and 3) that cell proliferation was inhibited under either nitrogen or phosphorus starvation conditions, but the proliferation under phosphorus starvation conditions was not inhibited as strongly as that under nitrogen starvation conditions. From these findings, the present inventors have obtained an idea that phosphorus starvation-inducible algae are more preferable than nitrogen starvation-inducible algae as TAG high-productivity algae. Furthermore, the present inventors have obtained a finding that a SQD2a gene promoter of *C. reinhardtii* is preferable as a phosphorus starvation-inducible promoter and DGTT4 gene of *C. reinhardtii* is preferable as a TAG synthase gene.

Based on the above findings, the present inventors have succeeded in preparing a *C. reinhardtii* strain with TAG high-productivity by introducing DGTT4 gene linked to the SQD2a gene promoter into *C. reinhardtii*, and filed a patent application regarding this *C. reinhardtii* strain (JP2014-68638, However, this application had not been published at the time of filing of Japanese Patent application No. 2014-049651, which is the basis of the priority of the present application).

The present inventors have further advanced this study, and succeeded in obtaining a TAG high-productivity algae strain from algae belonging to *Nannochloropsis*, which is more suitable for producing TAGs than *C. reinhardtii*. Further, the present inventors have obtained a finding that a TAG high-productivity strain can be efficiently prepared by introducing a construct having structure that DGTT4 gene is sandwiched between the SQD2a gene promoter and a 3' untranslated region of a gene derived from algae belonging to *Nannochloropsis*.

The present invention has been completed based on the above findings.

Specifically, the present invention provides the following [1] to [19].

[1] A method for preparing triacylglycerol high-productivity algae, the method comprising introducing a construct into algae, wherein the construct contains the following (1) to (3):
(1) a triacylglycerol synthase gene;
(2) a phosphorus starvation-inducible promoter located upstream of the triacylglycerol synthase gene; and
(3) a 3' untranslated region of a gene located downstream of the triacylglycerol synthase gene, wherein the gene is derived from algae of the same species as the algae into which the construct is to be introduced.

[2] The method for preparing triacylglycerol high-productivity algae according to [1], wherein the phosphorus starvation-inducible promoter is a SQD2 gene promoter.

[3] The method for preparing triacylglycerol high-productivity algae according to [1] or [2], wherein the triacylglycerol synthase gene is DGAT2 gene.

[4] The method for preparing triacylglycerol high-productivity algae according to [1] or [2], wherein the triacylglycerol synthase gene is DGTT4 gene.

[5] The method for preparing triacylglycerol high-productivity algae according to any one of [1] to [4], wherein the algae are algae belonging to *Nannochloropsis, Chlamydomonas, Pseudochoricystis, Phaeodactylum, Ostreococcus, Cyanidioschyzon, Klebsormidium, Chlorokybus, Spirogyra, Chara, Coleochaete, Chlorella*, or *Fistulifera*.

[6] The method for preparing triacylglycerol high-productivity algae according to any one of [1] to [4], wherein the algae are algae belonging to *Nannochloropsis*.

[7] Triacylglycerol high-productivity algae into which a construct has been introduced, wherein the construct contains the following (1) to (3):
(1) a triacylglycerol synthase gene;
(2) a phosphorus starvation-inducible promoter located upstream of the triacylglycerol synthase gene; and
(3) a 3' untranslated region of a gene located downstream of the triacylglycerol synthase gene, wherein the gene is derived from algae of the same species as the algae into which the construct is to be introduced.

[8] The triacylglycerol high-productivity algae according to [7], wherein the phosphorus starvation-inducible promoter is a SQD2 gene promoter.

[9] The triacylglycerol high-productivity algae according to [7] or [8], wherein the triacylglycerol synthase gene is DGAT2 gene.

[10] The triacylglycerol high-productivity algae according to [7] or [8], wherein the triacylglycerol synthase gene is DGTT4 gene.

[11] The triacylglycerol high-productivity algae according to any one of [7] to [10], wherein the algae are algae belonging to *Nannochloropsis, Chlamydomonas, Pseudochoricystis, Phaeodactylum, Ostreococcus, Cyanidioschyzon, Klebsormidium, Chlorokybus, Spirogyra, Chara, Coleochaete, Chlorella*, or *Fistulifera*.

[12] The triacylglycerol high-productivity algae according to any one of [7] to [10], wherein the algae are algae belonging to *Nannochloropsis*.

[13] A method for producing triacylglycerols, the method comprising: culturing the triacylglycerol high-productivity algae according to any one of [7] to [12] under phosphorus starvation conditions; accumulating triacylglycerols in the algae cells; and collecting the accumulated triacylglycerols.

[14] A method for preparing triacylglycerol high-productivity algae, the method comprising introducing a construct into algae, wherein the construct contains the following (1) to (2):
(1) a triacylglycerol synthase gene; and
(2) a phosphorus starvation-inducible promoter located upstream of the triacylglycerol synthase gene;

[15] The method for preparing triacylglycerol high-productivity algae according to [14], wherein the phosphorus starvation-inducible promoter is a SQD2 gene promoter.

[16] The method for preparing triacylglycerol high-productivity algae according to [14] or [15], wherein the triacylglycerol synthase gene is DGAT2 gene.

[17] The method for preparing triacylglycerol high-productivity algae according to [14] or [15], wherein the triacylglycerol synthase gene is DGTT4 gene.

[18] The method for preparing triacylglycerol high-productivity algae according to any one of [14] to [17], wherein the algae are algae belonging to *Nannochloropsis, Chlamydomonas, Pseudochoricystis, Phaeodactylum, Ostreococcus, Cyanidioschyzon, Klebsormidium, Chlorokybus, Spirogyra, Chara, Coleochaete, Chlorella*, or *Fistulifera*.

[19] The method for preparing triacylglycerol high-productivity algae according to any one of [14] to [17], wherein the algae are algae belonging to *Nannochloropsis*.

This specification includes the contents as disclosed in the specification and/or drawings of Japanese Patent Application (Patent Application No. 2014-049651), which is a priority document of the present application.

Advantageous Effects of Invention

The high-productivity algae of the present invention, for example, have the following effects.
(1) The accumulated amount of TAGs in the algae of the present invention is larger than that in algae known in the past.
(2) Since the TAG synthase gene is under the control of the phosphorus starvation-inducible promoter, this gene is not expressed strongly during standard culture. Thus, it is possible to control the timing of TAG accumulation.
(3) Although the proliferation efficiency is reduced as compared with the standard condition, cells can proliferate to some extent under phosphorus starvation conditions, so it is also possible to accumulate TAGs while cells are proliferating.
(4) Fatty acids in the accumulated TAGs are ones derived from not already synthesized lipids (lipids in chloroplast and the like) but newly synthesized lipids, so the algae of the present invention are also useful for producing useful specific fatty acids.

DESCRIPTION OF EMBODIMENTS

Figure 1:
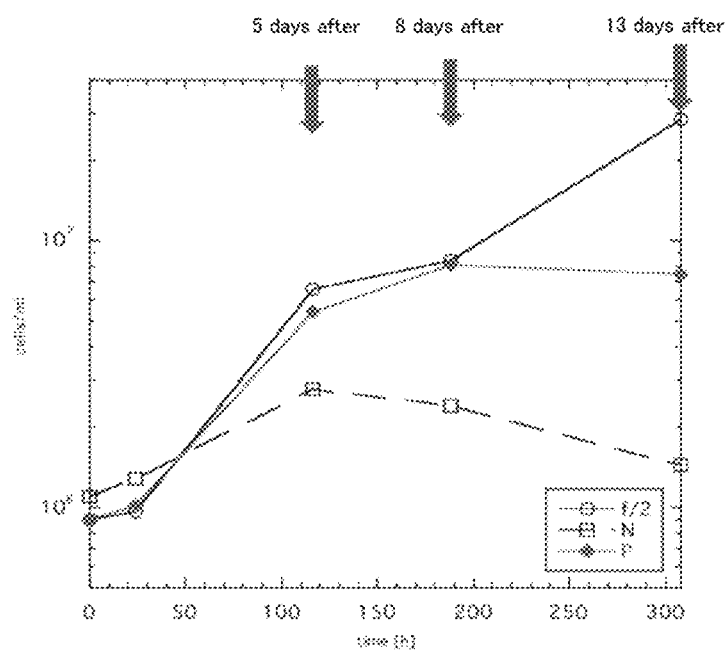
FIG. 1 is a graph showing proliferation curve under nutrient starvation conditions. In the figure, f/2, N, and P indicate the cases of culture in f/2 medium, nitrogen-deficient f/2 medium, and phosphorus-deficient f/2 medium, respectively.
Figure 2:
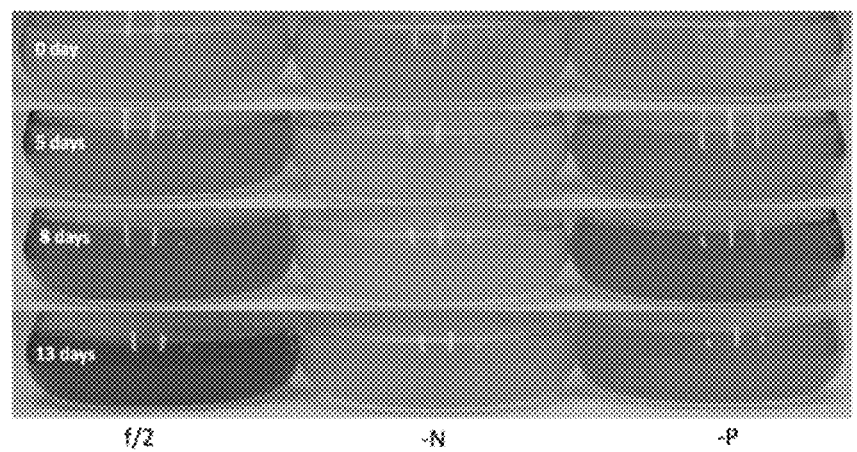
FIG. 2 is a photograph showing the culture solutions at 0, 5, 8, and 13 days after the start of the culture. In the figure, f/2, N, and P indicate the cases of culture in f/2 medium, nitrogen-deficient f/2 medium, and phosphorus-deficient f/2 medium, respectively.
Figure 3:
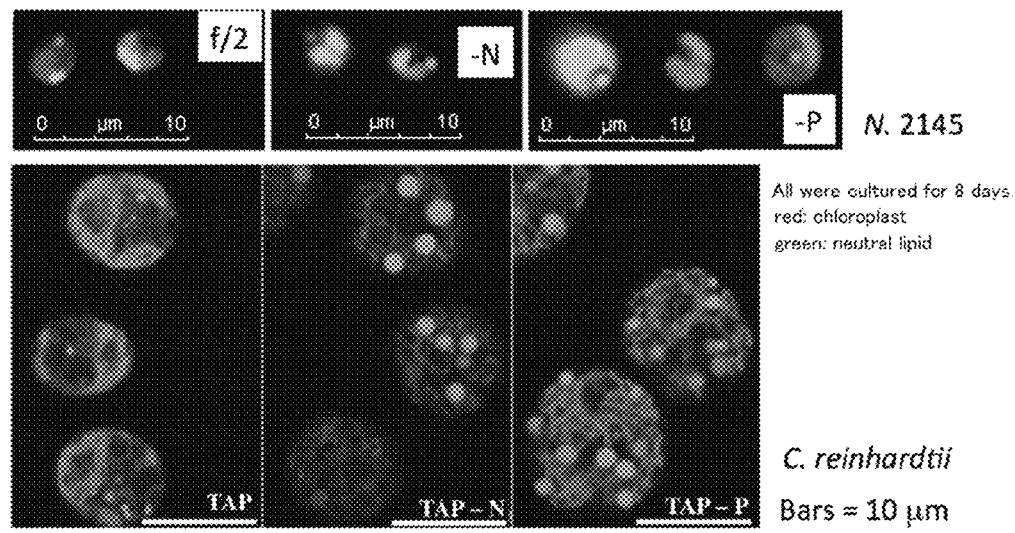
FIG. 3 is a fluorescence micrograph of the cells during nutrient starvation. In the figure, f/2, -N, -P, TAP, TAP-N, and TAP-P indicate the cases of culture in f/2 medium, nitrogen-deficient f/2 medium, phosphorus-deficient f/2 medium, TAP medium, nitrogen-deficient TAP medium, and phosphorus-deficient TAP medium, respectively.
Figure 4:
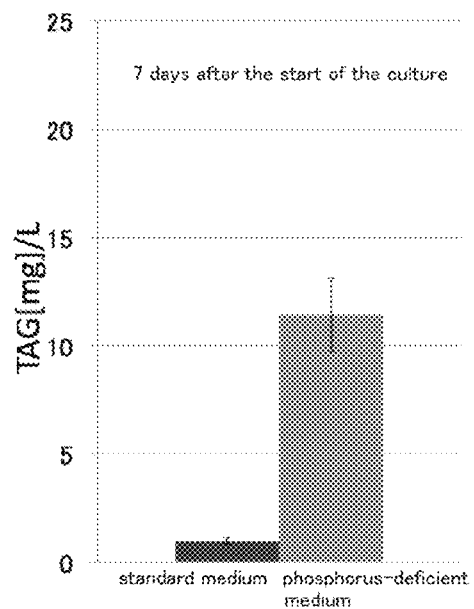
FIG. 4 is a graph showing the amount of TAGs per 1 L of the culture solution.

Hereinafter, the present invention will be described in detail.

The method for preparing triacylglycerol high-productivity algae of the present invention comprises introducing a construct into algae, wherein the construct contains (1) a TAG synthase gene, (2) a phosphorus starvation-inducible promoter located upstream of the TAG synthase gene, and (3) a 3' untranslated region of a gene located downstream of the TAG synthase gene, wherein the gene is derived from algae of the same species as the algae into which the construct is to be introduced.

As the TAG synthase gene, a diacylglycerol acyltransferase (DGAT) gene can be used. There are two isozymes of the DGAT, which are called DGAT1 and DGAT2. Either of them can be used in the present invention, but DGAT2 is preferably used. Since DGAT2 and the gene encoding the same have been reported in many papers (for example, Jay M. Shockey et al., The Plant Cell, Vol. 18 September 2006, 2294-2313, and Miller et al., Plant Physiology, vol. 154 2010, 1737-1752), a person skilled in the art can understand DGAT2 gene. Specific examples of DGAT2 gene include not only DGTT4 gene of C. reinhardtii described later but also DGAT2A gene (The base sequence is shown in SEQ ID NO: 28.), DGAT2B gene (The base sequence is shown in SEQ ID NO: 29.), DGAT2C gene (The base sequence is shown in SEQ ID NO: 30.), DGAT2D gene (The base sequence is shown in SEQ ID NO: 31.), DGAT2E gene (The base sequence is shown in SEQ ID NO: 32.), DGAT2F gene (The base sequence is shown in SEQ ID NO: 33.), DGAT2G gene (The base sequence is shown in SEQ ID NO: 34.), DGAT2H gene (The base sequence is shown in SEQ ID NO: 35.), DGAT2I gene (The base sequence is shown in SEQ ID NO: 36.), DGAT2J gene (The base sequence is shown in SEQ ID NO: 37.), and DGAT2K gene (The base sequence is shown in SEQ ID NO: 38.).

As DGAT2 gene, for example, DGTT4 gene can be used. DGTT4 is a protein belonging to a family of DGAT2 that is contained in C. reinhardtii. Since this protein and the gene encoding the same have been reported in many papers (for example, Boyle et al. The Journal of biological chemistry, 287 (2012), pp. 15811-15825 and Chen J E and Smith A G, J Biotechnol. 2012 Jun. 29), a person skilled in the art can understand DGTT4 gene. The amino acid sequence of DGTT4 and the base sequence of the gene encoding the same are shown in SEQ ID NO: 3 and SEQ ID NO: 2, respectively. DGTT4 gene in the present invention includes not only DGTT4 gene of C. reinhardtii (Cre03.g205050) but also genes corresponding to this gene in other organism (homologues and the like). Specific examples of such DGTT4 gene in organisms other than C. reinhardtii include DGAT2 (JGI protein ID77655) gene of Volvox carteri f. nagariensis and DGAT2 (JGI protein ID 21937) gene of Ostreococcus tauri.

Examples of the base sequence of DGTT4 gene include the base sequence shown in SEQ ID NO: 2. In addition, the base sequence of DGTT4 gene may be a base sequence that shows high identity to the base sequence shown in SEQ ID NO: 2, and that encodes a protein having an activity (diacylglycerol acyltransferase activity and the like). The "high identity" mentioned here means usually an identity of 90% or more, preferably an identity of 95% or more, more preferably an identity of 97% or more, still more preferably an identity of 99% or more. Further, values of "identity" in the present specification can be calculated using homology search programs known to a person skilled in the art. For example, they can be calculated using default parameters in homology algorithm BLAST in NCBI.

Further, the base sequence of DGTT4 gene may encode a protein comprising an amino acid sequence in which one or several amino acids are deleted, substituted, or added in the amino acid sequence of SEQ ID NO: 3 and having an activity (diacylglycerol acyltransferase activity and the like). The "one or several" mentioned here means usually 1-10, preferably 1-5, more preferably 1-3, still more preferably 1. Furthermore, the "deletion, substitution, or addition" includes not only artificial mutation but also naturally occurring mutation (mutant or variant) due to individual differences, differences of species, differences of genus, or the like.

As the TAG synthase gene, an enzyme gene other than DGTT4 gene may be used. For example, if TAGs containing a large amount of polyunsaturated fatty acids intend to be produced in algae, a TAG synthase gene that preferentially incorporates the polyunsaturated fatty acids into the TAGs may be used. Examples of such gene includes DGAT2 gene of Thalassiosira pseudonana (JP-T-2011-507513).

As the phosphorus starvation-inducible promoter, for example, a SQD2 gene promoter can be used. SQD2 is an enzyme involved in the synthesis of sulfoquinovosyldiacylglycerol (SQDG). This enzyme and the gene encoding the same have been reported in many papers (for example, Yu B, Xu C, Benning C., Proc Natl Acad Sci USA. 2002 April; 99(8):5732-7.), and the amino acid sequence of this enzyme has also been published in the database (For example, the amino acid sequence of SQD2 of C. reinhardtii (SQD2a) has been described under GenBank Accession No. XP_001689662.), so a person skilled in the art can understand SQD2 gene. As the SQD2 gene promoter, the SQD2a gene promoter of *C. reinhardtii* (The base sequence is shown in SEQ ID NO: 1.), a SQD2A gene promoter of *Nannochloropsis* sp. (The base sequence is shown in SEQ ID NO: 45.), a SQD2B gene promoter of *Nannochloropsis* sp. (The base sequence is shown in SEQ ID NO: 15.), or the like can be used.

Examples of the base sequence of the SQD2 gene promoter include not only SEQ ID NO: 1, SEQ ID NO: 15 and SEQ ID NO: 45 but also a base sequence maintaining the promoter activity that shows high identity to the base sequence shown in SEQ ID NO: 1, SEQ ID NO: 15 or SEQ ID NO: 45. The "high identity" mentioned here means usually an identity of 90% or more, preferably an identity of 95% or more, more preferably an identity of 97% or more, still more preferably an identity of 99% or more.

Further, the base sequence of the SQD2 gene promoter may be a base sequence in which one or several bases are deleted, substituted, or added in the base sequence of SEQ ID NO: 1, SEQ ID NO: 15 or SEQ ID NO: 45 and that maintains the promoter activity. The "one or several" mentioned here means usually 1-10, preferably 1-5, more preferably 1-3, still more preferably 1. Furthermore, the "deletion, substitution, or addition" includes not only artificial mutation but also naturally occurring mutation (mutant or variant) due to individual differences, differences of species, differences of genus, or the like.

As the phosphorus starvation-inducible promoter, a promoter other than the SQD2 gene promoter may be used. For example, a LDSP gene promoter (The base sequence is shown in SEQ ID NO: 46.), a LPAT-Y gene promoter (The base sequence is shown in SEQ ID NO: 44.), or the like can also be used.

The phosphorus starvation-inducible promoter is located upstream of the TAG synthase gene in the construct that is introduced into the algae. The phosphorus starvation-inducible promoter may be directly connected to the TAG synthase gene or be connected via a linker.

As the 3' untranslated region, a 3' untranslated region of the gene that is derived from algae of the same species as the algae into which the construct is to be introduced is used. In the Example, a 3' untranslated region of VCP (violaxanthin/chlorophyll a-binding protein) 1 is used, but the 3' untranslated region to be used is not particularly limited as long as it is a 3' untranslated region of the gene that is derived from algae of the same species as the algae into which the construct is to be introduced. Examples of the 3' untranslated region of a gene other than VCP1 gene include a 3' untranslated region of T35S of cauliflower mosaic virus and a 3' untranslated region of Rubisco small subunit RBCS2 of algae belonging to *Nannochloropsis* (Genome, Functional Gene Annotation, and Nuclear Transformation of the Heterokont Oleaginous Alga *Nannochloropsis oceanica* CCMP1779, PLoS Genet. 2012 November; 8(11). Epub 2012 Nov. 15.). The length of 3' untranslated region is not particularly limited, but is preferably 500-1500 bases, more preferably 500-700 bases. By incorporating this 3' untranslated region as well as the TAG synthase gene and the phosphorus starvation-inducible promoter into the construct, it becomes possible to efficiently prepare TAG high-productivity algae.

The 3' untranslated region is located downstream of the TAG synthase gene in the construct that is introduced into the algae. The 3' untranslated region may be directly connected to the TAG synthase gene or be connected via a linker.

The construct may contain not only the TAG synthase gene, the promoter, and the 3' untranslated region but also such other genes as an antibiotic resistance gene and a promoter expressing it.

The algae into which the construct is introduced are preferably algae belonging to *Nannochloropsis*, but they may be algae other than this. Examples of such algae include algae belonging to *Chlamydomonas*, algae belonging to *Pseudochoricystis*, algae belonging to *Phaeodactylum*, algae belonging to *Ostreococcus*, algae belonging to *Cyanidioschyzon*, algae belonging to *Klebsormidium*, algae belonging to *Chlorokybus*, algae belonging to *Spirogyra*, algae belonging to *Chara*, algae belonging to *Coleochaete*, algae belonging to *Chlorella*, and algae belonging to *Fistulifera*. Examples of the algae belonging to *Nannochloropsis* include algae belonging to *Nannochloropsis oculata*, algae belonging to *Nannochloropsis salina*, and algae belonging to *Nannochloropsis gaditana*. Examples of the algae belonging to *Chlamydomonas* include algae belonging to *Chlamydomonas reinhardtii*. Examples of the algae belonging to *Pseudochoricystis* include algae belonging to *Pseudochoricystis ellipsoidea*. Examples of the algae belonging to *Phaeodactylum* include algae belonging to *Phaeodactylum tricornutum*. Examples of the algae belonging to *Ostreococcus* include algae belonging to *Ostreococcus tauri*. Examples of the algae belonging to *Cyanidioschyzon* include algae belonging to *Cyanidioschyzon merolae*. Examples of the algae belonging to *Klebsormidium* include algae belonging to *Klebsoiniidium flaccidum*. Examples of the algae belonging to *Chara* include algae belonging to *Chara fragilis*. Examples of the algae belonging to *Coleochaete* include algae belonging to *Coleochaete scutata*. Examples of the algae belonging to *Chlorella* include algae belonging to *Chlorella vulgaris*. Examples of the algae belonging to *Fistulifera* include algae belonging to *Fistulifera solaris*.

As described above, the 3' untranslated region needs to be derived from algae of the same species as the algae into which the construct is to be introduced, but the TAG synthase gene and the phosphorus starvation-inducible promoter may be derived from algae of the same species as or different species from the algae into which the construct is to be introduced.

Such procedures as constructing the construct and introducing it into algae can be performed according to a conventional method.

Except for culture under phosphorus starvation conditions during TAG accumulation, the TAG high-productivity algae prepared by the methods described above can be cultured similarly to the conventional algae. For example, when algae belonging to *Nannochloropsis* are cultured, f/2 medium and the like can be used as medium, the culturing temperature can be about 20-25° C., and the light intensity during culture can be about 10~40 μE/m$^2$/sec. When algae belonging to *Chlamydomonas* are cultured, TAP medium and the like can be used as medium, the culturing temperature can be about 23-25° C., and the light intensity during culture can be about 10~40 μE/m$^2$/sec.

In case of accumulating TAGs in the TAG high-productivity algae, they are cultured under phosphorus starvation conditions. The culture under phosphorus starvation conditions can be performed for example by transferring cells in a logarithmic growth phase to medium obtained by removing phosphorus components (for example, $K_2HPO_4$, $KH_2PO_4$, etc.) from medium used during proliferation or medium in which concentration of phosphorus components was reduced to 33 µM or less to culture them in the medium. Usually, a sufficient amount of TAGs is accumulated in cells in culture of about 8-13 days. Further, in algae that can be cultured at high density such as algae belonging to *Nannochloropsis*, TAG can be also accumulated by culturing at high density for a certain time in the medium used during proliferation without transferring to medium such as medium from which phosphorus components was removed. It is assumed that this is because phosphorus starvation conditions occurred naturally by the culture for long period. Using this method for culturing at high density, a sufficient amount of TAGs is usually accumulated in cells in culture of about 7-20 days. Further, the "culture at high density" mentioned here usually means culture at cell density of $1 \times 10^8$ cells/ml or more.

According to conventional methods, TAGs can be collected from cells in which TAGs has been accumulated.

EXAMPLES

The present invention will be explained more specifically with reference to the following Examples. However, the present invention is not limited thereto.

Example 1

[Experimental Materials]
(1) Algae Strains
*Nannochloropsis* strain NIES-2145 (hereinafter referred to as "N. 2145"), which belongs to Eustigmatophyceae, was used. This strain can be obtained from the National Institute for Environmental Studies, Japan (http://www.nies.gojp/).

*Chlamydomonas reinhardtii* strain C9 (CC-408 mt-), which belongs to Chlorophyceae, was used. This strain can be obtained from *Chlamydomonas* Center (http://chlamycollection.org/).
(2) Gene Names and Protein IDs
Gene names and protein IDs (JGI *Chlamydomonas reinhardtii* 4.0) are as follows.
DGTT4, PID190539
SQD2a, PID116277
CBLP, PID164254
(3) Gene Sequences
The base sequence of the SQD2a promoter from *C. reinhardtii* (pCrSQD2a) is shown in SEQ ID NO: 1.
The base sequence of DGTT4 gene from *C. reinhardtii* (CrDGTT4) is shown in SEQ ID NO: 2.
The base sequence of sh ble gene is shown in SEQ ID NO: 4.
The base sequence of a VCP2 gene promoter from *Nannochloropsis* sp. (NannoVCP2gene promoter) is shown in SEQ ID NO: 5.
The base sequence of the VCP1 gene 3' untranslated region from *Nannochloropsis* sp. (NannoVCP1 (VCP1) 3'UTR) is shown in SEQ ID NO: 6.
[Experimental Procedure]
(1) Culture Condition
As standard culture medium, TAP medium was used to culture *C. reinhardtii*.

Fifty g of $Na_2EDTA.2H_2O$, 2.2 g of $ZnSO_4.7H_2O$, 1.14 g of $H_3BO_3$, 506 mg of $MnCl_2.4H_2O$, 499 mg of $FeSO_4.7H_2O$, 161 mg of $CoCl_2.6H_2O$, 157 mg of $CuSO_4.5H_2O$, 110 mg of $(NH_4)_6Mo_7O_{24}.4H_2O$, and 1.6 g of KOH were dissolved in 1 L of ion-exchanged water and stored as Hutner's trace elements at 4° C.

Four hundred mg of $NH_4Cl$, 51 mg of $CaCl_2.2H_2O$, 100 mg of $MgSO_4.7H_2O$, 119 mg of $K_2HPO_4$, 60.3 mg of $KH_2PO_4$, 10 mL of Hutner's trace elements, 1 mL of acetic acid, and 2.42 g of Tris (hydroxymethyl) aminomethane were dissolved in 998 mL of ion-exchanged water. The solution was used as liquid TAP medium after autoclave sterilization. When the TAP medium was used as plate medium, 12 g of INA Agar was added to the solution before autoclave sterilization.

TAP medium was used as medium for standard culture, and the culture was performed under 20-30 µE/m²/sec at 23° C. by using a rotary culturing method. As phosphorus-deficient medium, TAP medium from which $K_2HPO_4$ and $KH_2PO_4$ were removed was used. As nitrogen-deficient medium, TAP medium from which $NH_4Cl$ was removed was used.

As standard culture medium, f/2 medium or F2N50%SW medium was used to culture N. 2145.

f/2 medium was prepared as follows.

Four hundred forty mg of $Na_2EDTA.2H_2O$, 316 mg of $FeCl_3.6H_2O$, 1.2 mg of $CoSO_4.7H_2O$, 2.1 mg of $ZnSO_4.7H_2O$, 0.18 mg of $MnCl_2.4H_2O$, 0.7 mg of $CuSO_4.5H_2O$, and 0.7 mg of $Na_2MoO_4.2H_2O$ were dissolved in 100 mL of ion-exchanged water and stored as f/2 metal at 4° C. Seven point five mg of $NaNO_3$, 0.6 mg of $NaH_2PO_4.2H_2O$, 0.05 µg of Vitamin $B_{12}$, 0.05 µg of Biotin, 10 µg of Thiamine HCl, 1 mg of $Na_2SiO_3.9H_2O$, and 0.1 mL of the f/2 metal were dissolved in 99.9 mL of artificial seawater. The solution was used as liquid f/2 medium after filter sterilization. When the f/2 medium was used as plate medium, the medium was prepared as follows. Seven point five mg of $NaNO_3$, 0.6 mg of $NaH_2PO_4.2H_2O$, 0.05 µg of Vitamin $B_{12}$, 0.05 µg of Biotin, 10 µg of Thiamine HCl, 1 mg of $Na_2SiO_3.9H_2O$, and 0.1 ml of the f/2 metal were dissolved in 50 mL of 2-times concentrated artificial seawater, and this was sterilized by filtration. In another flask, 8 g of INA Agar was added to 50 mL of ion-exchanged water, and this was autoclaved. Then, these two solutions were mixed.

In experiments using N. 2145 (FIGS. 1-4), f/2 medium was used as medium for standard culture, and the culture was performed under 20-30 µE/m²/sec at 23° C. by using a rotary culturing method. As phosphorus-deficient medium, f/2 medium from which $NaH_2PO_4$ was removed was used. As nitrogen-deficient medium, f/2 medium from which $NaNO_3$ was removed was used.

F2N50%SW medium is F2N medium (PNAS, 2011, vol. 108 (no. 52) 21265-21269) made with 50% artificial seawater. This medium was prepared as follows.

Twelve point one one g of Tris (hydroxymethyl) aminomethane was dissolved in 100 mL of ion-exchanged water and adjusted to pH7.6 with HCl to obtain 1M Tris (pH7.6). Ten mL of 1 M Tris (pH7.6), 26.745 mg of $NH_4Cl$, 7.5 mg of $NaNO_3$, 3.0 mg of $NaH_2PO_4.2H_2O$, 0.25 µg of Vitamin $B_{12}$, 0.25 µg of Biotin, 50 µg of Thiamine HCl, 1 mg of $Na_2SiO_3.9H_2O$, and 0.5 mL of f/2 metal were dissolved in 50% artificial seawater to a total volume of 100 ml. After filter sterilization, the solution was used as liquid F2N50%SW. In experiments using N. 2145 into which a construct for expressing lipid synthesis genes were introduced (FIGS. 6-15), F2N50%SW, F2N50%SW without $NaH_2PO_4$, and F2N50%SW without $NaNO_3$ and $NH_4Cl$ were used as control medium, phosphorus-deficient medium, and nitrogen-deficient medium, respectively.
(2) Lipids Extraction
Culture solution (100-450 mL) was centrifuged at 800 g for 5 minutes to precipitate cultured cells. The cells were suspended in 1 mL of ion-exchanged water and stored at −80° C. Frozen cells were thawed, and 1 mL of chloroform and 2 mL of methanol were added to them. The cells were suspended every 10 minutes and placed at room temperature for 1 hour. Four ml of supernatant was collected by centrifugation with a swing rotor at 800 g for 5 minutes. To the precipitate were added 0.8 ml of 1% (W/V) KCl, 1 mL of chloroform, and 2 mL of methanol, and it was suspended. After that, 3.8 mL of the supernatant was collected by centrifugation with a swing rotor at 800 g for five minutes and mixed with the above-mentioned supernatant. To 7.8 mL of the supernatant were added 2 mL of chloroform and 1.2 mL of 1% (W/V) KCl, and the supernatant was suspended. After that, lipids extract in lower layer was collected by centrifugation with a swing rotor at 800 g for 5 minutes. The lipids extract was dried, dissolved in a mixture of chloroform and methanol (chloroform:methanol=2:1) to a concentration of 60 mg/ml, and stored at −20° C.

(3) Lipid Analysis

Fifty μL of lipids extract was spotted on a thin-layer silica plate and developed in developing solution (hexane:diethyl ether:acetic acid=160:40:4) for 45 minutes. Using 0.001% primuline, TAG was confirmed under UV irradiation. A portion of the silica plate containing TAG was scraped off. To it were added 100 μL of 1 mM pentadecanoic acid and 500 μL of 5% hydrochloric acid/methanol, and it was suspended. After that, the suspension was allowed to stand still at 85° C. for 1 hour. To it was added 500 μL of hexane and it was suspended. After that, methyl esters of fatty acids in the upper layer were collected by centrifugation with a swing rotor at 800 g for 5 minutes. To the lower layer was added again 500 μL of hexane, and it was suspended to collect the upper layer by centrifugation with a swing rotor at 800 g for 5 minutes. The methyl esters of fatty acids were dried, dissolved in 60 μL of hexane, and used as samples of gas chromatography. Gas chromatography was performed using SHIMADZU GC-2014 equipped with HR-SS-10 25 m (length)×0.25 mm (i.d.) (Shinwa Chemical Industries, Ltd., Japan).

(4) Extraction of RNA

To the frozen cells were added 3 or more volumes of RNA extract solution and 3 or more volumes of acidic phenol, and they were pulverized four times in a frozen state with ultrasonic waves (ultrasonic treatment for 15 seconds, ice cooling for 30 seconds). The supernatant (400-500 μL) was collected by centrifugation at 20,000 g for 5 minutes at 4° C. To the supernatant were added 300 μL of acidic phenol and 300 μL of chloroform, and it was suspended. After that, the supernatant (400-500 μL) was collected by centrifugation at 14 k rpm for 5 minutes at 4° C. These processes were repeated five times. To the supernatant were added 1/10 volume of 3M sodium acetate and 1 volume of isopropanol, and it was suspended. After that, the suspension was centrifuged at 20,000 g for 5 minutes at 4° C. To the precipitate was added 1 mL of 70% ethanol, then it was centrifuged at 20,000 g for 5 minutes at 4° C. After these processes were repeated twice, the precipitate was dried. After dissolving the dried precipitate in 400 μL of sterile ion-exchanged water, it was confirmed that the concentration of nucleic acid is 1 μg/μL or more. To 40 μL of the nucleic acid were added 5 μL of 10× DNase I Buffer, 0.5 μL of DNase I, and 4.5 μL of sterile ion-exchanged water, then it was allowed to stand still at 37° C. for 30 minutes. After adding 50 μL of acidic phenol and 50 μL of chloroform to obtain the suspension, 35 μL of the supernatant was collected by centrifugation at 20,000 g for 10 minutes at 4° C. To the supernatant were added 1/10 volume of 3M sodium acetate and 1 volume of isopropanol, and it was suspended. After that, the suspension was centrifuged at 20,000 g for 10 minutes at 4° C. To the precipitate was added 150 μL of 70% ethanol, then it was centrifuged at 20,000 g for 10 minutes at 4° C. After these processes were repeated twice, the precipitate was dried. After dissolving the dried precipitate in 50 μL of sterile ion-exchanged water, it was confirmed that the concentration of RNA is 1 μg/μL or more.

(5) Preparation of cDNA

To 1 μg of RNA were added 0.5 μL of 10 mM dNTP, 0.25 μL of 100 mM oligo dT18, 0.25 μL of 100 mM random 6 mer, and an appropriate amount (0-5 μL) of RNase free water to a total volume of 6 μL. Then, it was treated at 65° C. for 5 minutes and allowed to stand still on ice. Further, to it were added 2 μL of 5× cDNA Synthesis Buffer, 0.5 μL of 0.1 M DTT, 0.5 μL of RNase OUT, 0.5 μL of Thermo Script RT, and 0.5 μL of RNase free water. Then, it was treated at 50° C. (40 minutes), 60° C. (20 minutes), and 85° C. (5 minutes). The resulting cDNA was stored at −20° C.

(6) Quantitative RT-PCR Method

Twelve point five 4 of 2×SYBR Green (TAKARA), 1 μL of 10 μM primer_F, 1 μL of 10 μM primer_R, 2 μL of 5-fold diluted cDNA, 8.5 μL of sterile ion-exchanged water were suspended and used for the reaction.

Primers were used as follows.

```
Nanno_realRT_TUBf:
                                         (SEQ ID NO: 7)
    AGCATGGCATTGACTCCACC Nanno_realRT_TUBr:
                                         (SEQ ID NO: 8)
    AACGGCCTCGTTGTAGTACACG CrDGTT4_realRT_F:
                                         (SEQ ID NO: 9)
    GTTCGTGCAGTTCAGTGTGG CrDGTT4_realRT_R
                                         (SEQ ID NO: 10)
    CGGGCAGAATCCGAACA
```

(7) Acquisition of the Promoter Sequence

PCR was performed using genome of *C. reinhardtii* strain C9 as a template to obtain the promoter region of pCrSQD2a. The resulting sequence of about 1 kb was introduced into pMD20-T vector (TAKARA) or pZErO-2 (Invitrogen).

Five μL of 2× GC Buffer II, 1.6 μL of 2.5 mM dNTP, 1 μL of C9 strain genome, 0.05 μL of LA Taq, 1 μL of 10 μM primer_F, 1 μL of 10 μM primer_R, and 1.35 μL of sterile ion-exchanged water were suspended and used for the PCR.

PCR was performed in the following 3 steps.

step 1: 94° C. for 2 minutes step 2: 40 cycles of 94° C. for 45 seconds, 55° C. for 30 minutes, and 71° C. for 90 seconds step 3: 71° C. for 5 minutes Primers were used as follows.

```
SQD2a_F2:
                                         (SEQ ID NO: 11)
    CGGGATAGTTGTAGCTGTAG

SOD2a_R2:
                                         (SEQ ID NO: 12)
    CGAAGAGTTGAGGTGTGTGTTC
```

(8) Acquisition of CrDGTT4 Gene Sequence

PCR was performed using cDNA of *C. reinhardtii* during phosphorus starvation as a template to obtain a full length of DGTT4 gene. The resulting sequence of about 1 kb was introduced into pMD20-T vector (TAKARA) or pZErO-2 (Invitrogen).

One point five µL of LA PCR×10 buffer, 1.2 µL of 2.5 mM dNTP, 1.05 µL of MgCl$_2$, 0.075 µL of LA Taq, 1.5 µL of 5M betaine, 0.45 µL of DMSO, 1.5 µL of 10 µM primer_F, 1.5 µL of 10 µM primer_R, 0.2 µL of cDNA, and 6.1 µL of sterile ion-exchanged water were suspended and used for the PCR.

PCR was performed in the following 3 steps.
step 1: 94° C. for 3 minutes
step 2: 41 cycles of 94° C. for 30 seconds, 54° C. for 30 minutes, and 72° C. for 1 minute
step 3: 72° C. for 3 minutes
Primers were used as follows.

```
DGTT4_F2:
                                  (SEQ ID NO: 13)
ATGCCGCTCGCAAAGCTGCG

DGTT4_R2:
                                  (SEQ ID NO: 14)
CTACATTATGACCAGCTCCTC
```

(9) Transformation Method of N. 2145

N. 2145 strain was cultured in the standard medium until the density reached 2-3×10$^6$ cells/mL, and 500 mL of the culture was centrifuged at 980 g for 10 minutes at 4° C. to precipitate the cells. After the supernatant was removed, the cells were washed three times with 375 mM sorbitol cooled with ice. The precipitated cells after washing were suspended in 375 mM sorbitol to a final density of 5×10$^8$ cells/mL. To 200 µl of the concentrated cell were added 2-20 µg of the construct DNA and 2 µL of 10 mg/mL carrier ssDNA (Salmon Sperm). The cell suspension was put in a cuvette for electroporation (2 mm wide), and a voltage was applied once to it at 11 kV/cm with time constant of 12 msec. To the cuvette was added 1 mL of the standard medium to suspend the cells, and the cell suspension was transferred to 15 mL tube. Four ml of the standard medium was further added to a total volume of 5 ml. Rotation culture was performed at 10 µE/m$^2$/sec at 23° C. for 48 hours, then the cells were seeded on plates to which 5 mL of 0.4% INA Agar/f/2 and 2 µg/µL Zeocin™ were added. The plates were allowed to stand still at 20-30 µE/m$^2$/sec at 23° C. As transformants, colonies formed on 14-20 days after seeding were subcultured on new plates containing Zeocin™.

[Experimental Results]

(1) Study for Controlling TAG/Membrane Lipid Synthesizing System

As findings on accumulation of lipids in *C. reinhardtii*, which is a model algae, it has been reported that lipids were accumulated under nitrogen starvation conditions; that among the lipids, TAG that is a storage lipid was accumulated; and that the proportion of saturated fatty acids were increased (BMC Biotechnol. 2011; 11:7.). The present inventors found that the lipid accumulation occurred in logarithmic growth phase cells under phosphorus starvation conditions (JP 2014-049651). The present inventors examined whether lipids were similarly accumulated under phosphorus starvation conditions even in N. 2145 belonging to Eustigmatophyceae, which is an ultra microalgae and has high ability to produce oil.

(2) Comparison of Accumulated Amount of TAGs Under Nutrient Starvation Conditions Based on the results of lipid accumulation in *C. reinhardtii*, nitrogen starvation conditions and phosphorus starvation conditions were compared using N. 2145 in a logarithmic growth phase (1×10$^7$ cells/mL), which grows vigorously.

In case of subculture under nitrogen starvation conditions, it was found that the cell growth was strongly inhibited (FIGS. 1-3), as is the case with *C. reinhardtii*. In case of subculture under phosphorus starvation conditions, it was observed that the growth was not inhibited as strongly as under nitrogen starvation conditions and that TAG was accumulated (FIGS. 1-4), as is the case with *C. reinhardtii*. Since the growth was not inhibited as strongly as under nitrogen starvation conditions and a large amount of TAGs were accumulated, the present inventors found that the subculture under phosphorus starvation conditions was suitable for significant changes of fatty acid composition of TAGs from fatty acids of membrane lipids, as is the case with *C. reinhardtii*.

Further, the present inventors found that the accumulated amount of TAGs in N. 2145 is larger than that in *C. reinhardtii* under phosphorus starvation conditions. Under phosphorus starvation conditions, the accumulated amount of TAGs per liter of culture solution (cultured for 1 week) was 12 mg/L, and it was twice the amount in *C. reinhardtii* cultured for the same period. In addition, N. 2145 can be cultured up to such high density as 1×10$^9$ cells/mL in the standard medium or 2×10$^8$ cells/mL in the phosphorus-deficient medium. This is one hundred times the cell density of *C. reinhardtii*. It is expected that 1 g or more TAGs per 1 liter of culture solution will be obtained if N. 2145 is cultured at high density in the phosphorus-deficient medium.

(3) Construct Expressing Lipids Synthesis Genes from *C. reinhardtii*

Diacylglycerol acyltransferase (DGAT) is an enzyme that catalyzes the final step of TAG biosynthesis. DGAT is an enzyme that exists widely in animals and plants, and two types of DGAT (DGAT1 and DGAT2) have been reported.

It is known that there are one type of DGAT1 and five types of DGAT2 (DGTT1-5) in *C. reinhardtii*. Among these, it has been reported that mRNA level of DGTT1 was changed under nitrogen starvation conditions; that mRNA levels of DGTT2 and DGTT3 were little changed under nitrogen starvation conditions; and that DGTT5 was not expressed (Plant Physiol. 2010, Vol. 154, 1737-1752). The present inventor found the promoter pSQD2a that induced a strong expression under phosphorus starvation conditions, and developed a method for enhancing TAG accumulation by linking that promoter to DGTT4 gene (JP2014-049651).

This time, the present inventors amplified a promoter region of SQD2a (pCrSQD2a) by PCR using genome of *C. reinhardtii* as a template. Further, the sequence of CrDGTT4 gene was obtained from cDNA of *C. reinhardtii* under phosphorus starvation conditions. The pCrSQD2a was connected upstream of CrDGTT4 gene, and this was named pCrSQD2aCrDGTT4. The Zeocin™ resistance gene (ble from *S. hindustanus*) for mutant strain selection was connected upstream of pCrSQD2aCrDGTT4 to obtain shblepCrSQD2aCrDGTT4. In reference to Kilian et al. PNAS 2011, the VCP2 promoter of N.2145 and the VCP1 3'UTR of N.2145 were added to 5' end and 3' end of this sequence, respectively to obtain a construct (F) for enhancing TAG productivity. A construct containing only sh ble between the VCP2 promoter of N.2145 and the VCP1 3'UTR of N.2145 was used as a control. Further, in order to confirm whether adding the VCP1 3'UTR of N.2145 to 3' end of pCrSQD2aCrDGTT4 is valid, a construct (R) containing pCrSQD2aCrDGTT4 that was inserted in opposite directions was also produced (FIG. 5).

(4) Increased Production of TAGs in N. 2145

Figure 5:
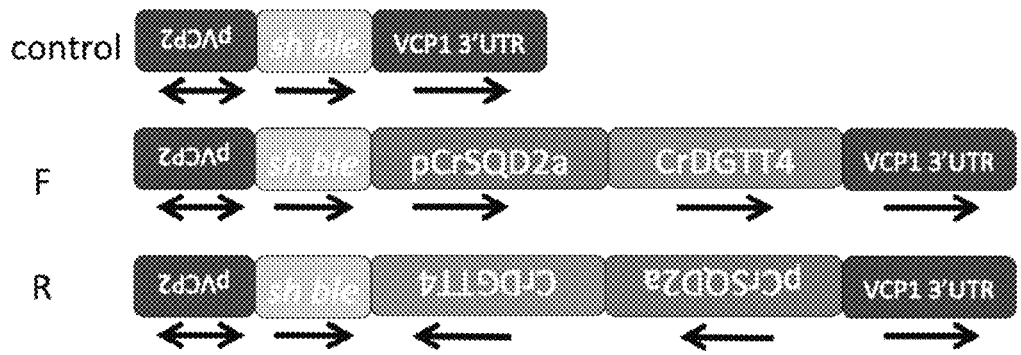
FIG. 5 is a schematic figure showing the structure of constructs for enhancing TAG productivity.
Figure 6:
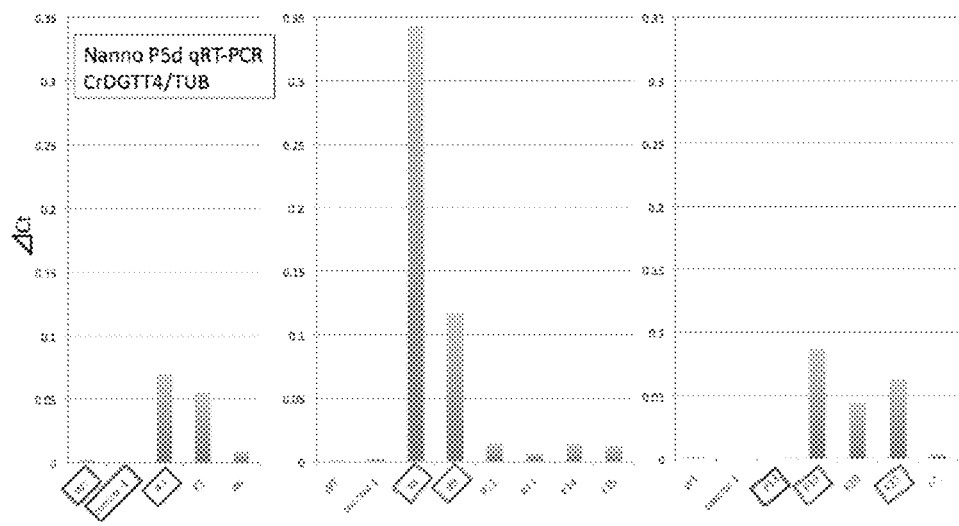
FIG. 6 is a graph showing the results of experiments for detecting expression of CrDGTT4 gene by Quantitative PCR.

N. 2145 was transformed with the constructs shown in FIG. 5 to obtain 20-30 transformants of the control strain and the F strain after selection by Zeocin™. Four transformants of the R strain were obtained. Quantitative RT-PCR was performed using RNA collected from transformants at 5 days after phosphorus depletion, and strains in which an increased expression of CrDGTT4 gene was detected were further selected. In the wild-type strain, the control strain, and the R strain, an increased expression of CrDGTT4 gene was not detected (FIG. 6). Thus, it is assumed that the combination of the promoter pCrSQD2a and the 3'UTR from N.2145 is effective in an increased expression of a gene sandwiched between them.

Five strains (#3, #8, #9, #19, #21) with an increased expression of CrDGTT4 gene and 1 strain (#18) without an increased expression of the gene among the F strains, as well as the wild-type strain and the control strain, were cultured in the phosphorus-deficient medium. The cells were collected at 4 and 7 days after phosphorus depletion to measure the accumulated amount of TAGs (FIGS. 7 and 8).

Figure 7:
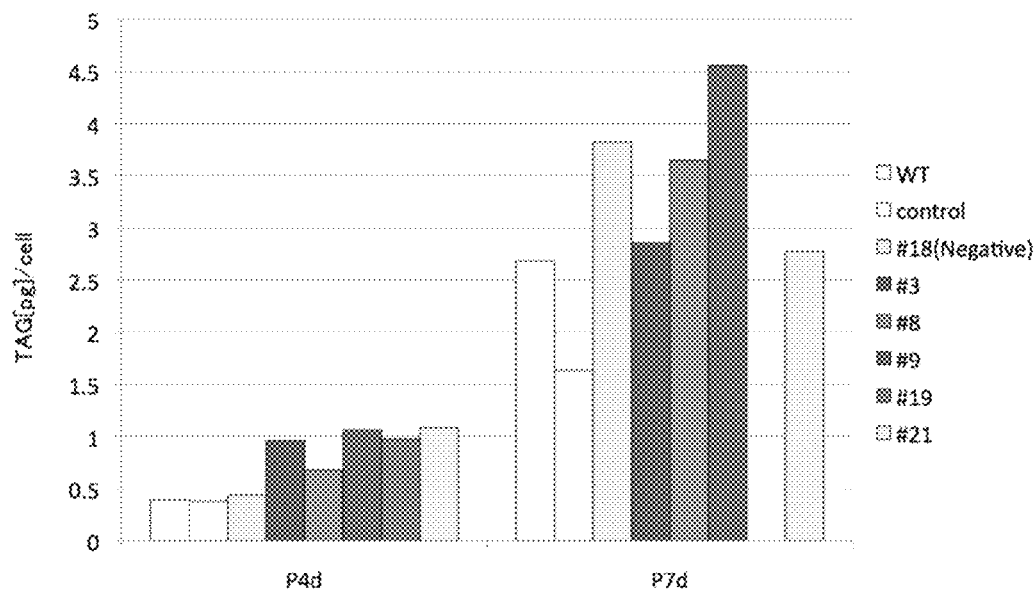
FIG. 7 is a graph showing the amount of TAGs per cell. In the figure, P4d and P7d indicate the amounts of TAGs at 4 days and 7 days after the start of the culture, respectively. Each bar indicates the amount of TAGs in the wild-type strain, the control strain, #18, #3, #8, #9, #19, or #21 (from the left). Further, the amount of TAG in #19 at 7 days after the start of the culture was not measured.
Figure 8:
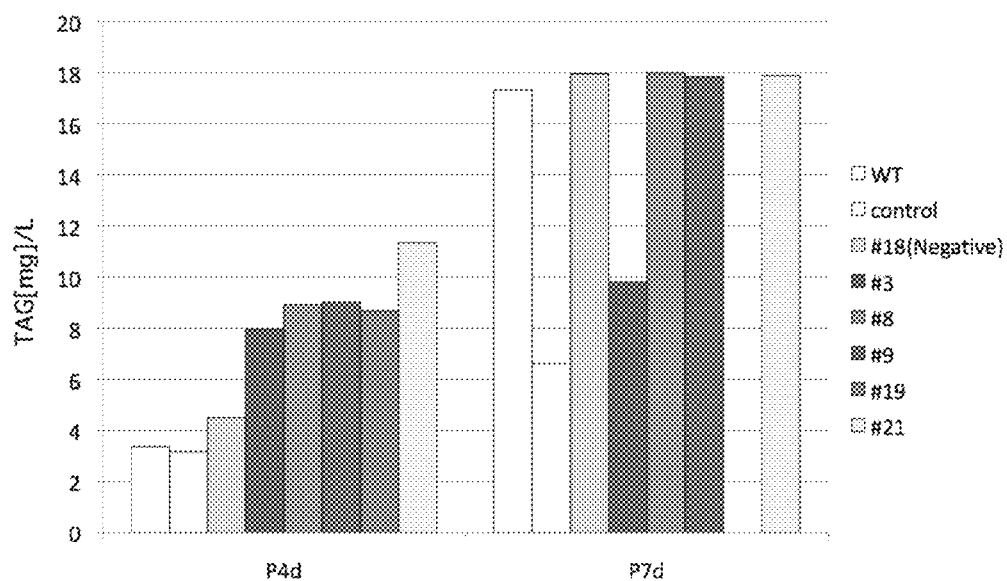
FIG. 8 is a graph showing the amount of TAGs per 1 L of the culture solution. In the figure, P4d and P7d indicate the amounts of TAGs at 4 days and 7 days after the start of the culture, respectively. Each bar indicates the amount of TAGs in the wild-type strain, the control strain, #18, #3, #8, #9, #19, or #21 (from the left). Further, the amount of TAGs in #19 at 7 days after the start of the culture was not measured.

As shown in FIGS. 7 and 8, it was observed that the accumulated amount of TAGs in #18, in which an increased expression of CrDGTT4 gene was not detected, was only equal to the amount accumulated in the control strain at 4 days after phosphorus depletion. It was found that the accumulated amount of TAGs in the five strains (#3, #8, #9, #19, #21) in which an increased expression of CrDGTT4 gene was detected was 2-3 times the accumulated amount in the wild-type strain and the control strain under phosphorus starvation conditions. The difference between the strains in which an increased expression of CrDGTT4 gene was detected and the wild-type strain was smaller at 7 days after phosphorus depletion. It is assumed that this is due to an expression of 11 types of DGAT2 from N. 2145 cell. This method is a method in which lipids can be accumulated efficiently in a short period of time and a method extremely useful for realizing biodiesel production or useful lipids production in algae, whose biomass is larger than that of land plants.

Figure 9:
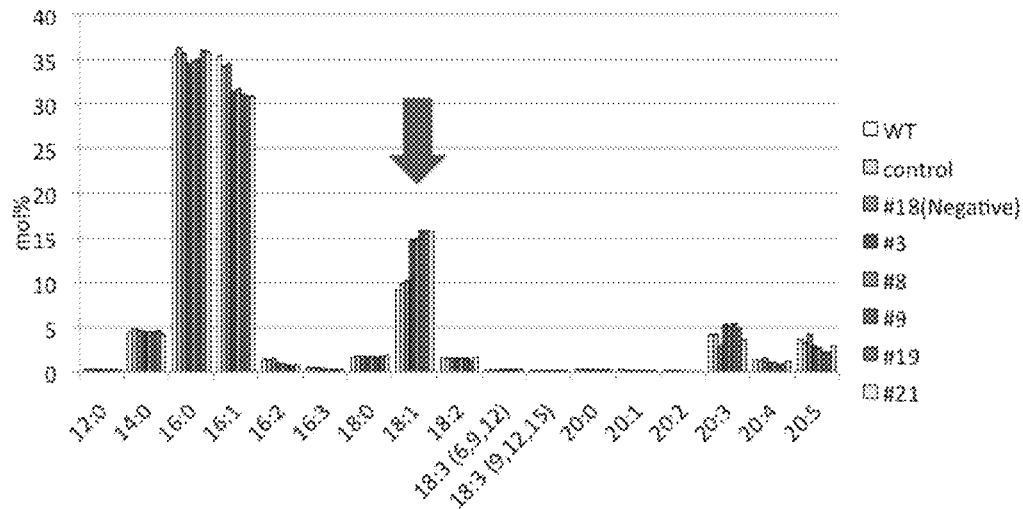
FIG. 9 is a graph showing the fatty acid composition of TAGs at 4 days after the start of the culture. Each bar indicates the amount of TAGs in the wild-type strain, the control strain, #18, #3, #8, #9, #19, or #21 (from the left).
Figure 10:
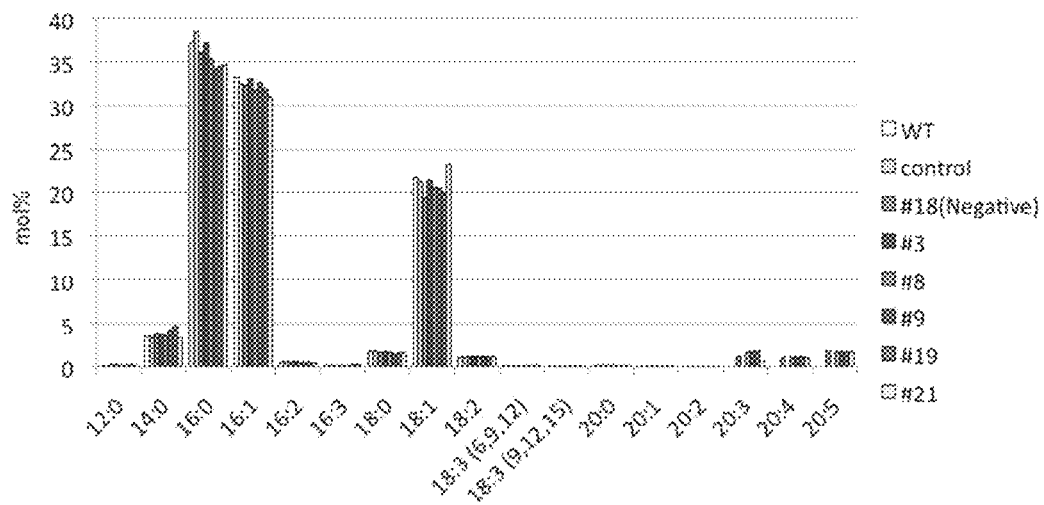
FIG. 10 is a graph showing the fatty acid composition of TAGs at 7 days after the start of the culture. Each bar indicates the amount of TAG in the wild-type strain, the control strain, #18, #3, #8, #9, #19, or #21 (from the left).

Further, as shown in FIG. 9, the fatty acid composition of TAGs at 4 days after phosphorus depletion indicated that the ratio of C18:1 was increased in the strains in which an increased expression of CrDGTT4 gene was detected, as compared to the wild-type strain or the control strain. However, this difference was no longer pronounced at 7 days after phosphorus depletion. It has been reported that CrDGTT4 prefers to use C18:1 as a substrate (Plant Cell 2013 February; 25(2):677-93). Thus, it is assumed that the combination of the promoter pCrSQD2a and the 3'UTR from N.2145 was suitable for significant changes of fatty acid composition of TAGs from fatty acids of membrane lipids.

The combination of the phosphorus starvation-inducible promoter pCrSQD2a and the 3'UTR from N.2145, which is used in the present invention, does not induce the expression during the standard culture, so the timing of oils and fats accumulation can be controlled. The method using this combination is suitable for synthesizing a novel fatty acid because it can accumulate oils and fats while proliferating cells under phosphorus starvation conditions. This is also an effective method to accumulate special fatty acids that are useful.

Example 2

In order to seek a phosphorus starvation-inducible promoter candidate from N. 2145, RNA was collected from cells at 4 and 6 days after nutrient depletion, and quantitative RT-PCR method was performed using it. Since an increased expression of SQD2a was detected in C. reinhardtii, gene expressions of SQD2A, SQD2B, and SQD2C, which are homologous genes of SQD2a in N. 2145, were examined. Further, since LDSP (lipid droplet surface protein) and LPAT were expected to be highly expressed from a prior paper (Plant Physiology, April 2012, Vol. 158, pp. 1562-1569) and a previous study in the laboratory of the present inventors, respectively, gene expressions of them were examined. In these experiments, the expression of actin was used as a control.

Primers were used as follows.

```
NannoACTf:
                                    (SEQ ID NO: 16)
5-ACCTTCTACAACGAGCTGC-3

NannoACTr:
                                    (SEQ ID NO: 17)
5-GAACGTCTCAAACATAATCTGG-3

NannoSQD2A_realRT_F:
                                    (SEQ ID NO: 18)
5-TCCCTTGCTTACTGCTCTGG-3

NannoSQD2A_realRT_R:
                                    (SEQ ID NO: 19)
5-GATTCGCGTAGCCGCTTA-3

NannoSQD2B_realRT_F:
                                    (SEQ ID NO: 20)
5-CTTAATACGACCACACACGTCCTC-3

NannoSQD2B_realRT_R:
                                    (SEQ ID NO: 21)
5-TGATACGCCTCCGCACTTT-3

NannoSQD2C_realRT_F:
                                    (SEQ ID NO: 22)
5-CCACGACTGCCGAATGA-3

NannoSQD2C_realRT_R:
                                    (SEQ ID NO: 23)
5-TGCTAGTGGACCCTTGTTGG-3 qRT_LPATY_L:
                                    (SEQ ID NO: 24)
5-gcttgtcgagtacccattcat-3 qRT_LPATY_:
                                    (SEQ ID NO: 25)
5-cagcagcccaaagaggttc-3 qRT_LDSP_L:
                                    (SEQ ID NO: 26)
5-gtgcctttcgacctetcg-3 qRT_LDSP_R:
                                    (SEQ ID NO: 27)
5-ggcacaaaaagatcctagcaa-3
```

Figure 11:
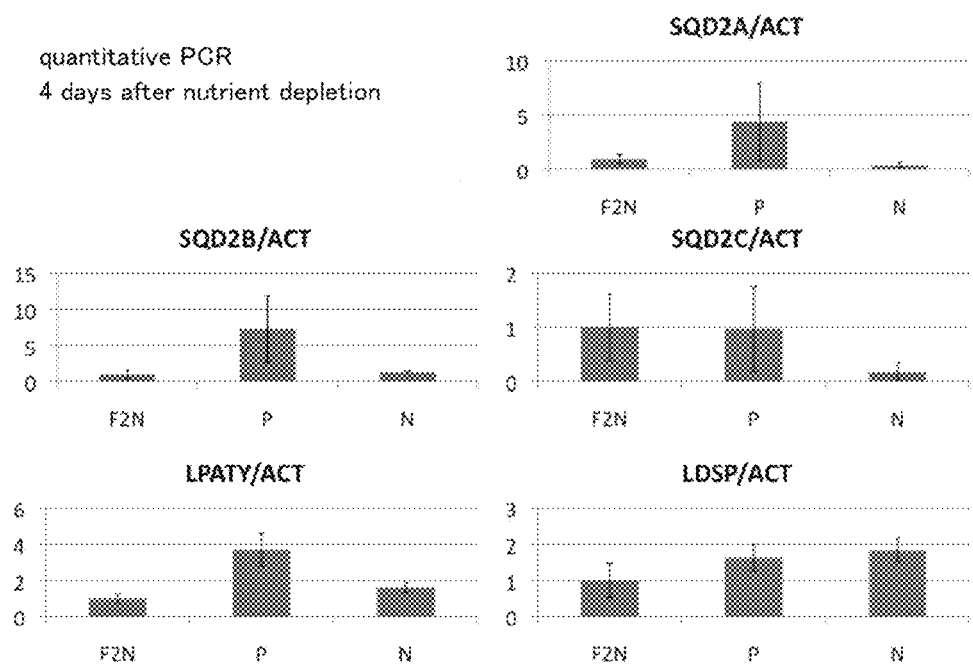
FIG. 11 is a graph showing the changes in expression of genes in N. 2145 cultured under nutrient starvation (4 days after nutrient depletion). In the figure, F2N, P, and N indicate the cases of culture in F2N50%SW medium, phosphorus-deficient F2N50%SW medium, and nitrogen-deficient F2N50%SW medium, respectively. The vertical axis of the graph shows relative value to the expression level of actin.
Figure 12:
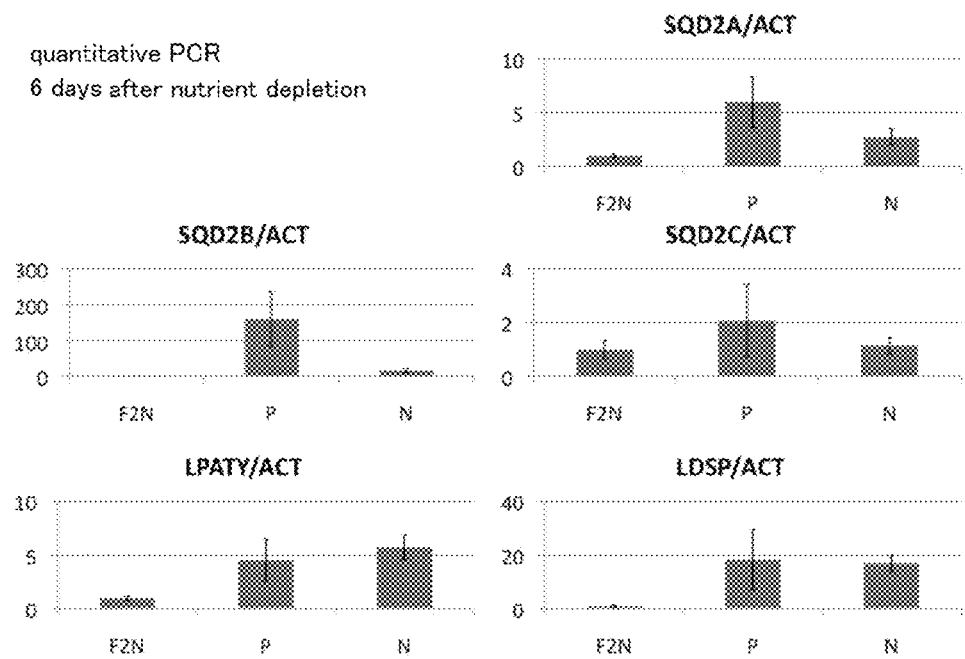
FIG. 12 is a graph showing the changes in expression of genes in N. 2145 cultured under nutrient starvation (6 days after nutrient depletion). In the figure, F2N, P, and N indicate the cases of culture in F2N50%SW medium, phosphorus-deficient F2N50%SW medium, and nitrogen-deficient F2N50%SW medium, respectively. The vertical axis of the graph shows relative value to the expression level of actin.

Expressions of LPAT-Y, SQD2-A, and SQD2-B were increased under phosphorus starvation conditions, and an expression of LDSP was increased under phosphorus starvation conditions and nitrogen starvation conditions (FIGS. 11 and 12). Expressions of 11 types of DGAT2 (DGAT2A-DGAT2K) and 2 types of DGAT1 were also examined, but their expressions were not increased as strongly as those of the above 4 genes. Thus, about 1kb of promoter regions of the above 4 genes were named pNLPATY, pNSQD2A, pNSQD2B, and pNLDSP, which are promoters from N. 2145 that induce a strong expression under phosphorus starvation conditions.

The present inventors amplified pNLPATY and pNSQD2B that are promoter regions of LPAT-Y and SQD2-

Figure 13:
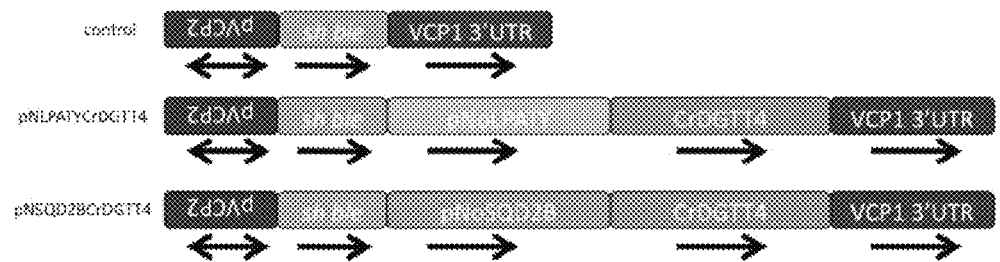
FIG. 13 is a schematic figure showing the structure of constructs in which the promoters from N. 2145 are used.

B, whose expressions were increased under phosphorus starvation conditions, by PCR using genome of *C. reinhardtii* as a template. The pNLPATY or pNSQD2B was connected upstream of CrDGTT4 gene instead of pCrSQD2a, and this was named pNLPATYCrDGTT4, or pNSQD2BCrDGTT4 (FIG. 13). N. 2145 was transformed with the constructs shown in FIG. 13 to obtain transformants after selection by Zeocin™. As is the case with pCrSQD2aCrDGTT4, quantitative RT-PCR was performed using RNA collected from the transformants at 4 and 6 days after phosphorus depletion. For quantitative RT-PCR, the following primers were used.

```
NannoACTf:
                (SEQ ID NO: 47)
5-ACCTTCTACAACGAGCTGC-3

NannoACTr:
                (SEQ ID NO: 48)
5-GAACGTCTCAAACATAATCTGG-3

CrDGTT4_realRT_F:
                (SEQ ID NO: 49)
5-GTTCGTGCAGTTCAGTGTGG-3

CrDGTT4_realRT_R:
                (SEQ ID NO: 50)
5-CGGGCAGAATCCGAACA-3
```

Figure 14:
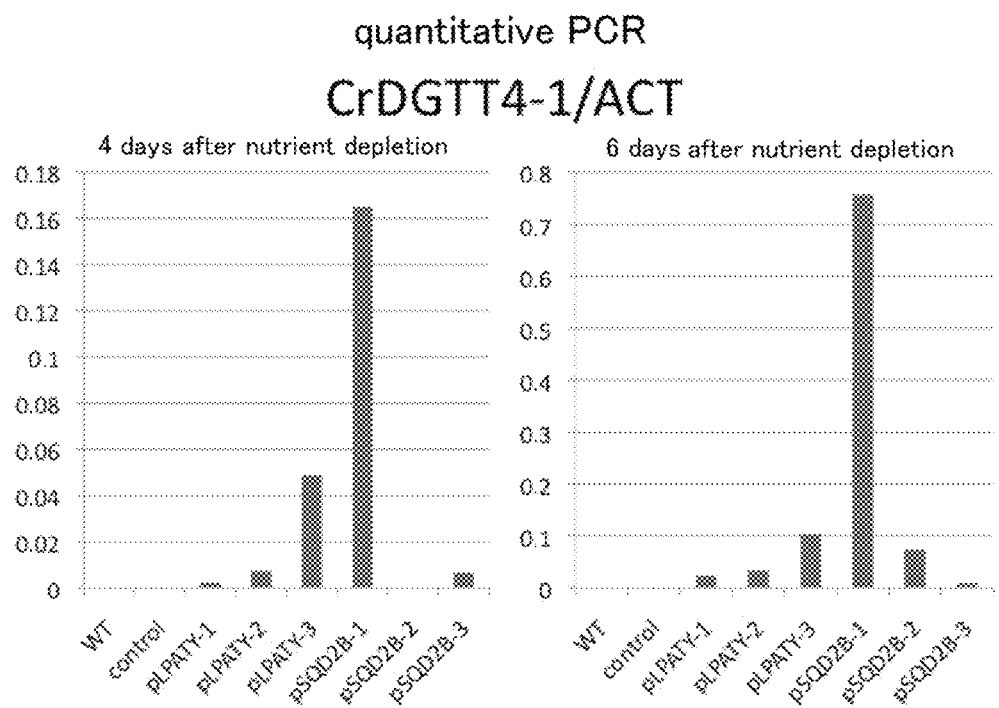
FIG. 14 is a graph showing the results of experiments for detecting expression of CrDGTT4 gene by Quantitative PCR. The left panel shows the result at 4 days after nutrient depletion, and the right panel shows the result at 6 days after nutrient depletion.
Figure 15:
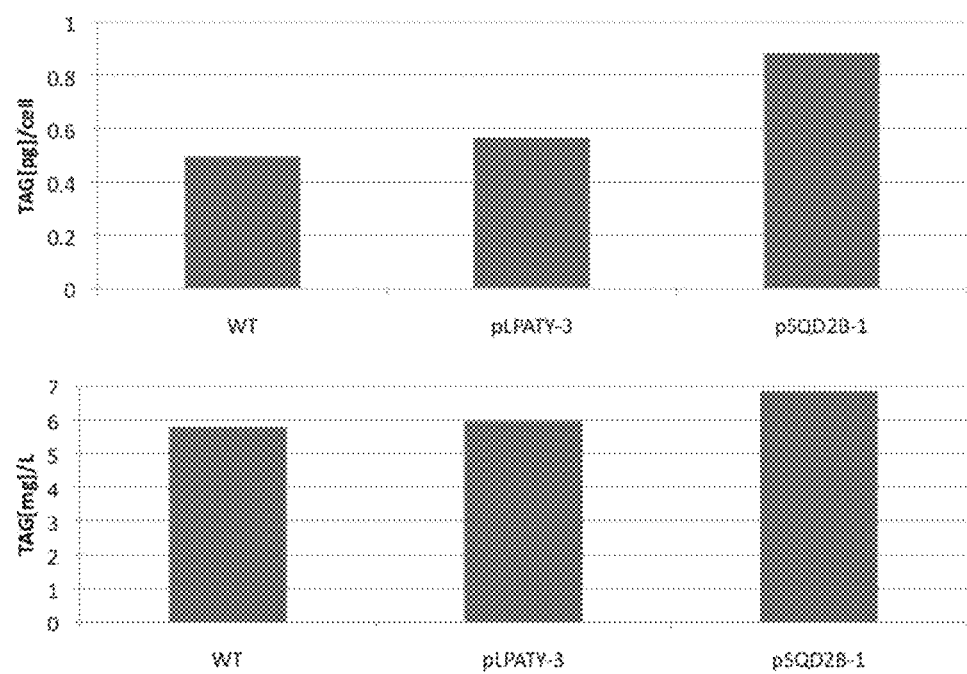
FIG. 15 is a graph showing the amount of TAGs per cell [pg] (upper panel) and the amount of TAGs per culture solution [mg] (lower panel).

The expression of CrDGTT4 gene was not detected in the wild-type strain and the control strain, but the expression of CrDGTT4 gene was detected in the transformants of pLPATY-1, pLPATY-2, pLPATY-3, pSQD2B-1, pSQD2B-2, and pSQD2B-3 (FIG. 14). The cells were cultured in 200 mL of the phosphorus-deficient medium and collected at 4 days after phosphorus depletion to measure the accumulated amount of TAGs (FIG. 15). As shown in FIG. 15, it was found that TAGs were more accumulated in the transformants of pLPATY-3 and pSQD2B-1 in which the increased expression of CrDGTT4 gene was detected than the wild-type strain under phosphorus starvation conditions. Thus, the present method using a promoter region of a phosphorus starvation-inducible gene in the gene expression for increased production of TAGs is a method in which lipids can be accumulated efficiently in a short period of time.

Further, the sequences of genes used in these examples are as follows.

A sequence of DGAT2A gene from N. 2145 is shown in SEQ ID NO: 28.
A sequence of DGAT2B gene from N. 2145 is shown in SEQ ID NO: 29.
A sequence of DGAT2C gene from N. 2145 is shown in SEQ ID NO: 30.
A sequence of DGAT2D gene from N. 2145 is shown in SEQ ID NO: 31.
A sequence of DGAT2E gene from N. 2145 is shown in SEQ ID NO: 32.
A sequence of DGAT2F gene from N. 2145 is shown in SEQ ID NO: 33.
A sequence of DGAT2G gene from N. 2145 is shown in SEQ ID NO: 34.
A sequence of DGAT2H gene from N. 2145 is shown in SEQ ID NO: 35.
A sequence of DGAT2I gene from N. 2145 is shown in SEQ ID NO: 36.
A sequence of DGAT2J gene from N. 2145 is shown in SEQ ID NO: 37.
A sequence of DGAT2K gene from N. 2145 is shown in SEQ ID NO: 38.
A sequence of SQD2A gene from N. 2145 is shown in SEQ ID NO: 39.
A sequence of SQD2B gene from N. 2145 is shown in SEQ ID NO: 40.
A sequence of SQD2C gene from N. 2145 is shown in SEQ ID NO: 41.
A sequence of LPAT-Y gene from N. 2145 is shown in SEQ ID NO: 42.
A sequence of LDSP gene from N. 2145 is shown in SEQ ID NO: 43.
A sequence of LPAT-Y gene promoter from N. 2145 is shown in SEQ ID NO: 44.
A sequence of SQD2A gene promoter from N. 2145 is shown in SEQ ID NO: 45.
A sequence of SQD2B gene promoter from N. 2145 is shown in SEQ ID NO: 15.
A sequence of LDSP gene promoter from N. 2145 is shown in SEQ ID NO: 46.

All the publications, patents, and patent applications cited in the present specification are incorporated into the present specification by reference in their entirety.

INDUSTRIAL APPLICABILITY

The present invention can be used in various industrial fields related to TAG production.

The invention claimed is:

1. A triacylglycerol high-productivity alga into which a construct has been introduced, wherein the construct contains the following (1) to (2):
   (1) a triacylglycerol synthase gene, which comprises a diacylglycerol acyltransferase gene (DGAT) of isozyme DGAT1 or DGAT2; and
   (2) a phosphorus starvation-inducible promoter located upstream of the triacylglycerol synthase, wherein the phosphorus starvation-inducible promoter is a promoter of an SQD2 gene, a LDSP gene or a LPAT-Y gene.

2. The triacylglycerol high-productivity alga according to claim 1, wherein the triacylglycerol synthase gene is DGAT2 gene.

3. The triacylglycerol high-productivity alga according to claim 1, wherein the triacylglycerol synthase gene is DGTT4 gene.

4. The triacylglycerol high-productivity alga according to claim 1, wherein the alga is an alga belonging to *Nannochloropsis, Chlamydomonas, Pseudochoricystis, Phaeodactylum, Ostreococcus, Cyanidioschyzon, Klebsormidium, Chlorokybus, Spirogyra, Chara, Coleochaete, Chlorella*, or *Fistulifera*.

5. The triacylglycerol high-productivity alga according to claim 1, wherein the alga is an alga belonging to *Nannochloropsis*.

6. A method for producing triacylglycerols, the method comprising: culturing the triacylglycerol high-productivity alga according to claim 1 under phosphorus starvation conditions; accumulating triacylglycerols in algae cells; and collecting the accumulated triacylglycerols.

7. A method for preparing triacylglycerol high-productivity alga, the method comprising introducing a construct into algae, wherein the construct contains the following (1) to (2):
   (1) a triacylglycerol synthase gene, which comprises a diacylglycerol acyltransferase gene (DGAT) of isozyme DGAT1 or DGAT2; and
   (2) a phosphorus starvation-inducible promoter located upstream of the triacylglycerol synthase gene, wherein the phosphorus starvation-inducible promoter is a promoter of an SQD2 gene, a LDSP gene or a LPAT-Y gene.

8. The method for preparing triacylglycerol high-productivity alga according to claim 7, wherein the triacylglycerol synthase gene is DGAT2 gene.

9. The method for preparing triacylglycerol high-productivity alga according to claim 7, wherein the triacylglycerol synthase gene is DGTT4 gene.

10. The method for preparing triacylglycerol high-productivity algae according to claim 7, wherein the alga is an alga belonging to *Nannochloropsis, Chlamydomonas, Pseudochoricystis, Phaeodactylum, Ostreococcus, Cyanidioschyzon, Klebsormidium, Chlorokybus, Spirogyra, Chara, Coleochaete, Chlorella*, or *Fistulifera*.

11. The method for preparing triacylglycerol high-productivity algae according to claim 7, wherein the alga is an alga belonging to *Nannochloropsis*.

12. The triacylglycerol high-productivity alga according to claim 1, wherein the construct further contains a 3' untranslated region of a gene located downstream of the triacylglycerol synthase gene, wherein the gene is derived from alga of the same species as the alga into which the construct is to be introduced.

13. The method for preparing triacylglycerol high-productivity algae according to claim 7, wherein the construct further contains a 3' untranslated region of a gene located downstream of the triacylglycerol synthase gene, wherein the gene is derived from alga of the same species as the alga into which the construct is to be introduced.

14. A triacylglycerol high-productivity *Nannochloropsis* alga into which a construct has been introduced, wherein the construct contains the following (1) to (2):
   (1) a triacylglycerol synthase gene, which comprises a diacylglycerol acyltransferase gene (DGAT) of isozyme DGAT1 or DGAT2; and
   (2) a phosphorus starvation-inducible promoter located upstream of the triacylglycerol synthase gene, wherein the phosphorus starvation-inducible promoter is a promoter of an SQD2 gene.

15. A method for preparing triacylglycerol high-productivity *Nannochloropsis* alga, the method comprising introducing a construct into algae, wherein the construct contains the following (1) to (2):
   (1) a triacylglycerol synthase gene, which comprises a diacylglycerol acyltransferase gene (DGAT) of isozyme DGAT1 or DGAT2; and
   (2) a phosphorus starvation-inducible promoter located upstream of the triacylglycerol synthase gene, wherein the phosphorus starvation-inducible promoter is a promoter of an SQD2 gene.

* * * * *

SEQUENCE LISTING

```
<160> NUMBER OF SEQ ID NOS: 50

<210> SEQ ID NO 1
<211> LENGTH: 963
<212> TYPE: DNA
<213> ORGANISM: Chlamydomonas reinhardtii
<220> FEATURE:
<221> NAME/KEY: promoter
<222> LOCATION: (1)..(963)

<400> SEQUENCE: 1
cgggatagtg tagctgtagc tgttggcggg cgcgggcgag ggctgcagcc tgttgggggc      60
```

-continued

```
ggtgttgccg tttgccgagg ccacggggcg cggggcgtg gtggtgtggc cttggctggg    120
tgtggcggcg gcgaggacgc ccctgcgccg gtcgctgcgg tgtcggcagc ggccagtgga    180
cgccgctcct ggtgccgcgc aggtccgcac ggccgtgtac gggctgttgg ggcccggccc    240
tggcgccagt tccggggctg agaaaagtgc gcccaaggtg gaggccgctg atggcgcaga    300
tgcctgaggg taaactgcgc cccggcctgc atggcggctg gctcggttgg cggttgcggg    360
cacggtcgcg gtgacggtgc ctccgacagc cccaaatggc cgaacgccgc gcggcaggcg    420
cgtcgccggt aatgccgcta acatattttc tctattaatt cctccaactg cagtggcaac    480
gttgatttgg gttctcaaca ggcaacaatc gaggacttgc agaccgagac gctgggtttg    540 taccctgat gcggtgacaa tattttaaat tgagcatata gcaagacctg caatcaaagg    600
gagtcaacaa ccgctccgtt gggcgggcct catggcctgc aacgtgcatc ggaccatcgc    660
gtctctttgg ccgcttgcac tagggtttgc gtcagacgac aagtgagcca tatgtgattg    720
tgtgcgtgac caaaggtgag ctcacttgca gcatgcgctg caagcctccc gccaaaggca    780
agcataaacc gcttcgtatg gctcctcatt ctcctgaact tactgcaggc tggtctacga    840
gcgcaattga gctgcttaca ttgaaggcca cgcgcggcgc cggcgaagcc cgacgcaagc    900
tgtgataccg gaatatcagt atcagcgcgt cgatgcgcta cttttagagg gccaagagcg    960
aca                                                                963
```

<210> SEQ ID NO 2
<211> LENGTH: 984
<212> TYPE: DNA
<213> ORGANISM: Chlamydomonas reinhardtii
<220> FEATURE:
<221> NAME/KEY: CDS
<222> LOCATION: (1)..(981)

<400> SEQUENCE: 2

```
atg ccg ctc gca aag ctg cga aac gtg gtg ctg gag tac gcg gcc ata     48
Met Pro Leu Ala Lys Leu Arg Asn Val Val Leu Glu Tyr Ala Ala Ile
  1               5                  10                  15 gcc atc tac gtc agc gcc atc tac acc tcg gtg gtg ctg ctg ccc tcg     96
Ala Ile Tyr Val Ser Ala Ile Tyr Thr Ser Val Val Leu Leu Pro Ser
             20                  25                  30 gcg ctc gcg ctg ttc tac ctg ttt ggg gcc acc agc ccc tcg gcc tgg    144
Ala Leu Ala Leu Phe Tyr Leu Phe Gly Ala Thr Ser Pro Ser Ala Trp
         35                  40                  45 ctg ctg cta gcc gcc ttc ctg gcc ctc acc ttc acg ccg ctg cag ctg    192
Leu Leu Leu Ala Ala Phe Leu Ala Leu Thr Phe Thr Pro Leu Gln Leu
     50                  55                  60 acc acc ggt gcg ctg tcg gag cgg ttc gtg cag ttc agt gtg gcg cgg    240
Thr Thr Gly Ala Leu Ser Glu Arg Phe Val Gln Phe Ser Val Ala Arg
 65                  70                  75                  80 gcg gcg gcc tac ttc ccc acc cgc gtg gtg gtc acg gac ccg gag gcc    288
Ala Ala Ala Tyr Phe Pro Thr Arg Val Val Val Thr Asp Pro Glu Ala
                 85                  90                  95 ttc cgc act gac cgc ggc tac ttg ttc gga ttc tgc ccg cac tcg gct    336
Phe Arg Thr Asp Arg Gly Tyr Leu Phe Gly Phe Cys Pro His Ser Ala
            100                 105                 110 ctg ccc atc gca ctg ccc atc gcc ttc gcc acc acc tcg ccg ctg ctg    384
Leu Pro Ile Ala Leu Pro Ile Ala Phe Ala Thr Thr Ser Pro Leu Leu
        115                 120                 125 ccc aag gag ctg cgc ggc cgc aca cac ggc ttg gcg tcg tcc gtg tgc    432
Pro Lys Glu Leu Arg Gly Arg Thr His Gly Leu Ala Ser Ser Val Cys
    130                 135                 140
```

```
ttc agc gcg ccc ata gtg cgg cag ctg tac tgg tgg ctg ggc gtg cgg      480
Phe Ser Ala Pro Ile Val Arg Gln Leu Tyr Trp Trp Leu Gly Val Arg
145                 150                 155                 160 ccc gcc acg cgg cag agc atc agc ggc ctg ttg cgg gcg cgc aag gtg      528
Pro Ala Thr Arg Gln Ser Ile Ser Gly Leu Leu Arg Ala Arg Lys Val
                165                 170                 175 gcg gtg ctg gtg ccg ggg ggc gtg cag gag gtg ctc aac atg gag cac      576
Ala Val Leu Val Pro Gly Gly Val Gln Glu Val Leu Asn Met Glu His
            180                 185                 190 ggc aag gag gtg gcc tac ctc tcc agc cgc acc ggc ttc gtg cga ctg      624
Gly Lys Glu Val Ala Tyr Leu Ser Ser Arg Thr Gly Phe Val Arg Leu
        195                 200                 205 gcc gtg cag cac ggc gcg ccg ctg gtg cca gtg tgg gcg ttc ggc cag      672
Ala Val Gln His Gly Ala Pro Leu Val Pro Val Trp Ala Phe Gly Gln
    210                 215                 220 acg cgc gcg tac agc tgg ttc cgg ccg ggg ccg ccg ctc gtg ccc acg      720
Thr Arg Ala Tyr Ser Trp Phe Arg Pro Gly Pro Pro Leu Val Pro Thr
225                 230                 235                 240 tgg ctc gtg gag cgc atc tca cgt gcc gcc ggc gcc gta ccc atc ggc      768
Trp Leu Val Glu Arg Ile Ser Arg Ala Ala Gly Ala Val Pro Ile Gly
                245                 250                 255 atg ttt ggg cag tac ggc acg ccc atg ccg cac cgc gag ccc ctc acc      816
Met Phe Gly Gln Tyr Gly Thr Pro Met Pro His Arg Glu Pro Leu Thr
                260                 265                 270 att gtg gtg ggt cgc ccc atc ccg gtg ccg gag ctg gcg ccg ggc cag      864
Ile Val Val Gly Arg Pro Ile Pro Val Pro Glu Leu Ala Pro Gly Gln
            275                 280                 285 ctc gag ccc gag ccc gag gtg ctg gcg gcg ctc ctc aag cgc ttc acg      912
Leu Glu Pro Glu Pro Glu Val Leu Ala Ala Leu Leu Lys Arg Phe Thr
        290                 295                 300 gac gac ctg cag gcg ctg tac gac aag cac aag gcg cag ttc ggc aag      960
Asp Asp Leu Gln Ala Leu Tyr Asp Lys His Lys Ala Gln Phe Gly Lys
305                 310                 315                 320 ggc gag gag ctg gtc ata atg tag                                      984
Gly Glu Glu Leu Val Ile Met
                325

<210> SEQ ID NO 3
<211> LENGTH: 327
<212> TYPE: PRT
<213> ORGANISM: Chlamydomonas reinhardtii

<400> SEQUENCE: 3

Met Pro Leu Ala Lys Leu Arg Asn Val Val Leu Glu Tyr Ala Ala Ile
1               5                   10                  15

Ala Ile Tyr Val Ser Ala Ile Tyr Thr Ser Val Val Leu Leu Pro Ser
                20                  25                  30

Ala Leu Ala Leu Phe Tyr Leu Phe Gly Ala Thr Ser Pro Ser Ala Trp
            35                  40                  45

Leu Leu Leu Ala Ala Phe Leu Ala Leu Thr Phe Thr Pro Leu Gln Leu
        50                  55                  60

Thr Thr Gly Ala Leu Ser Glu Arg Phe Val Gln Phe Ser Val Ala Arg
65                  70                  75                  80

Ala Ala Ala Tyr Phe Pro Thr Arg Val Val Val Thr Asp Pro Glu Ala
                85                  90                  95

Phe Arg Thr Asp Arg Gly Tyr Leu Phe Gly Phe Cys Pro His Ser Ala
            100                 105                 110

Leu Pro Ile Ala Leu Pro Ile Ala Phe Ala Thr Thr Ser Pro Leu Leu
        115                 120                 125
```

```
Pro Lys Glu Leu Arg Gly Arg Thr His Gly Leu Ala Ser Ser Val Cys
    130                 135                 140

Phe Ser Ala Pro Ile Val Arg Gln Leu Tyr Trp Leu Gly Val Arg
145                 150                 155                 160

Pro Ala Thr Arg Gln Ser Ile Ser Gly Leu Leu Arg Ala Arg Lys Val
                    165                 170                 175

Ala Val Leu Val Pro Gly Gly Val Gln Glu Val Leu Asn Met Glu His
                180                 185                 190

Gly Lys Glu Val Ala Tyr Leu Ser Ser Arg Thr Gly Phe Val Arg Leu
            195                 200                 205

Ala Val Gln His Gly Ala Pro Leu Val Pro Val Trp Ala Phe Gly Gln
        210                 215                 220

Thr Arg Ala Tyr Ser Trp Phe Arg Pro Gly Pro Leu Val Pro Thr
225                 230                 235                 240

Trp Leu Val Glu Arg Ile Ser Arg Ala Ala Gly Ala Val Pro Ile Gly
                245                 250                 255

Met Phe Gly Gln Tyr Gly Thr Pro Met Pro His Arg Glu Pro Leu Thr
                260                 265                 270

Ile Val Val Gly Arg Pro Ile Pro Val Pro Glu Leu Ala Pro Gly Gln
                275                 280                 285

Leu Glu Pro Glu Pro Glu Val Leu Ala Ala Leu Leu Lys Arg Phe Thr
            290                 295                 300

Asp Asp Leu Gln Ala Leu Tyr Asp Lys His Lys Ala Gln Phe Gly Lys
305                 310                 315                 320

Gly Glu Glu Leu Val Ile Met
                325

<210> SEQ ID NO 4
<211> LENGTH: 375
<212> TYPE: DNA
<213> ORGANISM: Streptoalloteichus hindustanus
<220> FEATURE:
<221> NAME/KEY: CDS
<222> LOCATION: (1)..(372)

<400> SEQUENCE: 4 atg gcc aag ttg acc agt gcc gtt ccg gtg ctc acc gcg cgc gac gtc      48
Met Ala Lys Leu Thr Ser Ala Val Pro Val Leu Thr Ala Arg Asp Val
1               5                   10                  15 gcc gga gcg gtc gag ttc tgg acc gac cgg ctc ggg ttc tcc cgg gac      96
Ala Gly Ala Val Glu Phe Trp Thr Asp Arg Leu Gly Phe Ser Arg Asp
                20                  25                  30 ttc gtg gag gac gac ttc gcc ggt gtg gtc cgg gac gac gtg acc ctg     144
Phe Val Glu Asp Asp Phe Ala Gly Val Val Arg Asp Asp Val Thr Leu
            35                  40                  45 ttc atc agc gcg gtc cag gac cag gtg gtg ccg gac aac acc ctg gcc     192
Phe Ile Ser Ala Val Gln Asp Gln Val Val Pro Asp Asn Thr Leu Ala
        50                  55                  60 tgg gtg tgg gtg cgc ggc ctg gac gag ctg tac gcc gag tgg tcg gag     240
Trp Val Trp Val Arg Gly Leu Asp Glu Leu Tyr Ala Glu Trp Ser Glu
65                  70                  75                  80 gtc gtg tcc acg aac ttc cgg gac gcc tcc ggg ccg gcc atg acc gag     288
Val Val Ser Thr Asn Phe Arg Asp Ala Ser Gly Pro Ala Met Thr Glu
                85                  90                  95 atc ggc gag cag ccg tgg ggg cgg gag ttc gcc ctg cgc gac ccg gcc     336
Ile Gly Glu Gln Pro Trp Gly Arg Glu Phe Ala Leu Arg Asp Pro Ala
                100                 105                 110
```

```
ggc aac tgc gtg cac ttc gtg gcc gag gag cag gac taa              375
Gly Asn Cys Val His Phe Val Ala Glu Glu Gln Asp
        115                 120
```

<210> SEQ ID NO 5
<211> LENGTH: 751
<212> TYPE: DNA
<213> ORGANISM: Nannochloropsis sp.
<220> FEATURE:
<221> NAME/KEY: promoter
<222> LOCATION: (1)..(751)

<400> SEQUENCE: 5

```
caagcaagac ggaacaagat ggcacgcgtc tgcaacagac cggctcgcgc cgaacgtgcc      60
tcctgctttt caacgatcct gcgaggtcaa ccaggatttg ctcgccggga cgatttcatc     120
cccttatcaa cgagcccttg aggctccagg cgtgcttcca cacccagtt ggtaacagga      180
cattggggca tcttgcctat cttgtcttag tgccgaaagc ctcaacgacc tcccatgggg     240
tctgctcaac gcctcaacct tgcagtaagg atccccgagg gcaagacccg caaagccttc     300
tgtcgtcgga caaagcggag cgagggaaca ggctcagctc aaccctcttg agagcccata     360
agtgccccct gatctatctt caacagtctt cccctgtcac aagaaaaccc agctagttga     420
ccaagttgct agagctgaca tccttgtact tcgctctttc tgtgctttac ctgattggac     480
atggacagac ctcccttgc tcttccttct aggagcctgg gctctcgctc ttgttctttc      540
gagagacctt tcccttgagt tgcgtatcca gcgatcaagt atgaagagtg ctttcaaacc     600
tagatacgtt ctgcccagtt ctcttgccct tttccacacg tgctccacat cttcacacga     660
ctcgcaccat acccgacgaa acccctcaaa acatcgcaac acttacatcc cgctcgtgtc     720
ccaccccgga tgccatatcc tctacagcag c                                    751
```

<210> SEQ ID NO 6
<211> LENGTH: 664
<212> TYPE: DNA
<213> ORGANISM: Nannochloropsis sp.
<220> FEATURE:
<221> NAME/KEY: 3'UTR
<222> LOCATION: (1)..(664)

<400> SEQUENCE: 6

```
gcttctgtgg aagagccagt ggtagtagca gtagcagcag cagtagcagc cgcagcactc      60
agtgttggcg cgagagattg tccatccctt cttaacctac cggaagagaa ataaggcctt     120
tctcccgtag ctgtcttcgt ttgtttgtgc tgattgcttg gtatgagagt gttgaattcc     180
tgcatcatgt ttttctctgt agtccttccc tacccccgtc attttctttt ctccctggtt    240
cttcttttgt caccccttatt ttacataaaa ttttctttgt ttatagtgag aggaaggtag    300
agaggggaaa acaagaacaa cgaacgcaag cgtgtgaaag gagggcgaat agaagagaaa     360
cagatctgtt gagcattgag agtggagccg ggggaaaggc ttgtgtgttg ttttgaaaa      420
agtttgttta aatcacgaat ccgttagttc tcatgtgtac ctctttcact acatgtgatg    480
gagaaaacaa aagtgtgagg attaattgaa gaaaagaag agttcgacac gtcaaaccgc     540
ccaaaagacg tcacaaagag aacttgattc tctttgccgt gttgatcttg tcttttcccc    600
cagcttttct tgccacccgt ggcacacgag atggacaaga tcagctgcag gcatgcaagc     660
ttgg                                                                  664
```

<210> SEQ ID NO 7
<211> LENGTH: 20

```
<212> TYPE: DNA
<213> ORGANISM: Artificial Sequence
<220> FEATURE:
<223> OTHER INFORMATION: Description of Artificial Sequence:primer

<400> SEQUENCE: 7
agcatggcat tgactccacc                                                    20

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence:primer

<400> SEQUENCE: 8
aacggcctcg ttgtagtaca cg                                                 22

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence:primer

<400> SEQUENCE: 9
gttcgtgcag ttcagtgtgg                                                    20

<210> SEQ ID NO 10
<211> LENGTH: 17
<212> TYPE: DNA
<213> ORGANISM: Artificial Sequence
<220> FEATURE:
<223> OTHER INFORMATION: Description of Artificial Sequence:primer

<400> SEQUENCE: 10
cgggcagaat ccgaaca                                                       17

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence:primer

<400> SEQUENCE: 11
cgggatagtt gtagctgtag                                                    20

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence:primer

<400> SEQUENCE: 12
cgaagagttg aggtgtgtgt tc                                                 22

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence:primer

<400> SEQUENCE: 13
```
atgccgctcg caaagctgcg                                           20

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence:primer

<400> SEQUENCE: 14
ctacattatg accagctcct c                                         21

<210> SEQ ID NO 15
<211> LENGTH: 1097
<212> TYPE: DNA
<213> ORGANISM: Nannochloropsis sp.
<220> FEATURE:
<221> NAME/KEY: promoter
<222> LOCATION: (1)..(1097)

<400> SEQUENCE: 15
aggagtagga gggagtatgg ggggagggat gggcggaggg ctgaacgggg gcagtactca      60
catgtctttc gttggctcca cacaacctac ctcgtcggcg actggcatgc aagcatcgcc     120
gccactgtct tccggcttcg tctcgacggg tgggggagc ttgagtgtga gccaatcggg      180
tggggatggg ggaggacaaa ggacgatgta tggtgcgcaa agtgatagct ttttgcaaca     240
gcaccaacag tttgcgccat catcctatcc gcctgccgtg cctggagggt ggcagcagca     300
gcaatggccc cagcaatcgc agccacagcc gtggcaacaa gcatcggagc cgcagcaggg     360
acagagacca tcgtctgctg ggccgcagcc accaaagcca caggcgcagc aagacaatcc     420
cttcgacgca tttatgtaga attgcattta tgtgtgttac tagagtatgg agaagatgaa     480
agataaataa atgaaaacag ttgggttgtg tttcagaaaa gtgggtggtg tgacgggttg     540
gtttattttt atttgatggc gatgttgctc cgttgctttt gaatttcaac ctgcgtgctt     600
caactcgccg ttgttcgtca gagaatctct gctgggccga gccacaccat gccttccaag     660
tctcgactac agccctaaaa gggcttgcaa tacatctggc tagaatattt gaacatgcaa     720
catcatgtct gttttgaaaa cctgtacttt ttcttgtttc tttgcagtct ttcgaccttc     780
gcatgctgct gggattgtcg gactgaatca cacaacattc cttcccctg cagcgccttg      840
ccacatccca attttcgtga acgggcttcc tgcctaagaa ttcttctcat atttgcgttg     900
aaaagacttt gccctgtcat gctgaccttg tttcaaccaa gtctcacgat aacacgccgc     960
ccgccactcc catattcgca cacatattcg cacacagagc acttgctacc ctcccgcgcc    1020
gaggccgaag acaagatcgt tgcttcttcc cgcccgagtt ataacccgca catctcaaaa    1080
gctacgccgt gaccgag                                                    1097

<210> SEQ ID NO 16
<211> LENGTH: 19
<212> TYPE: DNA
<213> ORGANISM: Artificial Sequence
<220> FEATURE:
<223> OTHER INFORMATION: Description of Artificial Sequence:primer

<400> SEQUENCE: 16
accttctaca acgagctgc                                            19

<210> SEQ ID NO 17
<211> LENGTH: 22
<212> TYPE: DNA

```
<213> ORGANISM: Artificial Sequence
<220> FEATURE:
<223> OTHER INFORMATION: Description of Artificial Sequence:primer

<400> SEQUENCE: 17
gaacgtctca aacataatct gg                                              22

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence:primer

<400> SEQUENCE: 18
tcccttgctt actgctctgg                                                 20

<210> SEQ ID NO 19
<211> LENGTH: 18
<212> TYPE: DNA
<213> ORGANISM: Artificial Sequence
<220> FEATURE:
<223> OTHER INFORMATION: Description of Artificial Sequence:primer

<400> SEQUENCE: 19
gattcgcgta gccgctta                                                   18

<210> SEQ ID NO 20
<211> LENGTH: 24
<212> TYPE: DNA
<213> ORGANISM: Artificial Sequence
<220> FEATURE:
<223> OTHER INFORMATION: Description of Artificial Sequence:primer

<400> SEQUENCE: 20
cttaatacga ccacacacgt cctc                                            24

<210> SEQ ID NO 21
<211> LENGTH: 19
<212> TYPE: DNA
<213> ORGANISM: Artificial Sequence
<220> FEATURE:
<223> OTHER INFORMATION: Description of Artificial Sequence:primer

<400> SEQUENCE: 21
tgatacgcct ccgcactttt                                                 19

<210> SEQ ID NO 22
<211> LENGTH: 17
<212> TYPE: DNA
<213> ORGANISM: Artificial Sequence
<220> FEATURE:
<223> OTHER INFORMATION: Description of Artificial Sequence:primer

<400> SEQUENCE: 22
ccacgactgc cgaatga                                                    17

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence:primer

<400> SEQUENCE: 23
tgctagtgga cccttgttgg                                                 20
```

-continued

```
<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence:primer

<400> SEQUENCE: 24
gcttgtcgag tacccattca t                                              21

<210> SEQ ID NO 25
<211> LENGTH: 19
<212> TYPE: DNA
<213> ORGANISM: Artificial Sequence
<220> FEATURE:
<223> OTHER INFORMATION: Description of Artificial Sequence:primer

<400> SEQUENCE: 25
cagcagccca agaggttc                                                  19

<210> SEQ ID NO 26
<211> LENGTH: 18
<212> TYPE: DNA
<213> ORGANISM: Artificial Sequence
<220> FEATURE:
<223> OTHER INFORMATION: Description of Artificial Sequence:primer

<400> SEQUENCE: 26
gtgcctttcg acctctcg                                                  18

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence:primer

<400> SEQUENCE: 27
ggcacaaaaa gatcctagca a                                              21

<210> SEQ ID NO 28
<211> LENGTH: 1092
<212> TYPE: DNA
<213> ORGANISM: Nannochloropsis sp.
<220> FEATURE:
<221> NAME/KEY: CDS
<222> LOCATION: (1)..(1089)

<400> SEQUENCE: 28 atg acg ccg caa gcc gac atc acc agc aag acg aca ccc aac ctc aag      48
Met Thr Pro Gln Ala Asp Ile Thr Ser Lys Thr Thr Pro Asn Leu Lys
  1               5                  10                  15 acg gct gcg tca tcc ccc tcc aag acc tcg ccc gcc ccc tcc gtt caa      96
Thr Ala Ala Ser Ser Pro Ser Lys Thr Ser Pro Ala Pro Ser Val Gln
             20                  25                  30 tac aag gcg gcg aat ggc aag gtg atc acg gtg gcc atg gcc gag caa     144
Tyr Lys Ala Ala Asn Gly Lys Val Ile Thr Val Ala Met Ala Glu Gln
         35                  40                  45 gac gac ggg aac atg ggc att ttc cgc gag tgt ttt gca atg gtg aca     192
Asp Asp Gly Asn Met Gly Ile Phe Arg Glu Cys Phe Ala Met Val Thr
     50                  55                  60 atg ggc ata att atg tcg tgg tat tac atc gtc gtc att ctc tcc ctc     240
Met Gly Ile Ile Met Ser Trp Tyr Tyr Ile Val Val Ile Leu Ser Leu
 65                  70                  75                  80
```

```
ctc tgc ttg gtg ggg atc tgc atc ttc cct gcc tgg cgg gcg gta gcg      288
Leu Cys Leu Val Gly Ile Cys Ile Phe Pro Ala Trp Arg Ala Val Ala
                85                  90                  95 gcc acg gtt ttt gtg ctt atg tgg agt gcg gcg cta ttg ccg ctt gac      336
Ala Thr Val Phe Val Leu Met Trp Ser Ala Ala Leu Leu Pro Leu Asp
        100                 105                 110 tac cag gga tgg gat gct ttc tgc aac tcc ttt atc ttc agg ctg tgg      384
Tyr Gln Gly Trp Asp Ala Phe Cys Asn Ser Phe Ile Phe Arg Leu Trp
    115                 120                 125 cgg gac tac ttc cac tat gaa tac gtc ctg gag gag atg atc gac cca      432
Arg Asp Tyr Phe His Tyr Glu Tyr Val Leu Glu Glu Met Ile Asp Pro
130                 135                 140 aac aag cgc tac ctc ttt gct gag atg cct cac ggt atc ttc ccc tgg      480
Asn Lys Arg Tyr Leu Phe Ala Glu Met Pro His Gly Ile Phe Pro Trp
145                 150                 155                 160 gga gag gtg att tcc att tcg atc acc aaa cag ctt ttt ccc ggg agc      528
Gly Glu Val Ile Ser Ile Ser Ile Thr Lys Gln Leu Phe Pro Gly Ser
                165                 170                 175 cgc gta ggc tcc atc ggt gcg agt gtc atc ttc ctc ctt ccc ggt ctc      576
Arg Val Gly Ser Ile Gly Ala Ser Val Ile Phe Leu Leu Pro Gly Leu
            180                 185                 190 agg cac ttc ttc gct tgg atc ggg tgt cgg ccc gcg agc cca gag aac      624
Arg His Phe Phe Ala Trp Ile Gly Cys Arg Pro Ala Ser Pro Glu Asn
        195                 200                 205 atc aaa aag att ttt gag gat ggg cag gac tgt gcc gtg acg gtg ggg      672
Ile Lys Lys Ile Phe Glu Asp Gly Gln Asp Cys Ala Val Thr Val Gly
    210                 215                 220 ggg gtc gcc gag atg ttt cta gtc gga gga gac aag gaa cga ctg tac      720
Gly Val Ala Glu Met Phe Leu Val Gly Gly Asp Lys Glu Arg Leu Tyr
225                 230                 235                 240 ctg aag aag cac aag ggt ttc gtt cga gaa gcc atg aag aat ggg gcg      768
Leu Lys Lys His Lys Gly Phe Val Arg Glu Ala Met Lys Asn Gly Ala
                245                 250                 255 gac ctg gtt cct gtc ttc tgc ttc ggc aac agc aag ctg ttc aat gtg      816
Asp Leu Val Pro Val Phe Cys Phe Gly Asn Ser Lys Leu Phe Asn Val
            260                 265                 270 gtg ggg gag agc agt cgg gtt tct atg ggc ctg atg aag cgc ctc tca      864
Val Gly Glu Ser Ser Arg Val Ser Met Gly Leu Met Lys Arg Leu Ser
        275                 280                 285 agg agg att aag gcc agc gtc ctc atc ttt tac ggc cgt ctc ttc ctg      912
Arg Arg Ile Lys Ala Ser Val Leu Ile Phe Tyr Gly Arg Leu Phe Leu
    290                 295                 300 ccc att ccg att cga cac ccg ctc ttg ttc gtg gtg ggg aag ccc ctg      960
Pro Ile Pro Ile Arg His Pro Leu Leu Phe Val Val Gly Lys Pro Leu
305                 310                 315                 320 ccg gtc gtg cac aag gca gag ccg acc aag gag gag atc gcg gca acg     1008
Pro Val Val His Lys Ala Glu Pro Thr Lys Glu Glu Ile Ala Ala Thr
                325                 330                 335 cac gca ctc ttt tgc gag aag gtc gag gag ctt tac tac aaa tac agg     1056
His Ala Leu Phe Cys Glu Lys Val Glu Glu Leu Tyr Tyr Lys Tyr Arg
            340                 345                 350 ccg gag tgg gag acg cgc ccg ttg tcc att gag taa                     1092
Pro Glu Trp Glu Thr Arg Pro Leu Ser Ile Glu
        355                 360
```

<210> SEQ ID NO 29
<211> LENGTH: 1083
<212> TYPE: DNA
<213> ORGANISM: Nannochloropsis sp.
<220> FEATURE:

<221> NAME/KEY: CDS
<222> LOCATION: (1)..(1080)

<400> SEQUENCE: 29

```
atg gcc aag gcc aac ttc cca ccc tcg gca cgc tat gtt aat atg acg      48
Met Ala Lys Ala Asn Phe Pro Pro Ser Ala Arg Tyr Val Asn Met Thr
 1               5                  10                  15 cag gtc tat gcg aca ggt gct cac aat atg ccg gac gag gac cgt ctc      96
Gln Val Tyr Ala Thr Gly Ala His Asn Met Pro Asp Glu Asp Arg Leu
             20                  25                  30 aag gtg atg aat gga ctt tcc aag ccc ttg acg gag gcc aag ccc ggt     144
Lys Val Met Asn Gly Leu Ser Lys Pro Leu Thr Glu Ala Lys Pro Gly
         35                  40                  45 gat ttg ggg ttt ggg gat gtg gag tcc atg acg ttc tgt gaa gag ttt     192
Asp Leu Gly Phe Gly Asp Val Glu Ser Met Thr Phe Cys Glu Glu Phe
     50                  55                  60 gta gcg att atg ttc tta ttg atc att gtc ggg agc atg ctt tgg ata     240
Val Ala Ile Met Phe Leu Leu Ile Ile Val Gly Ser Met Leu Trp Ile
 65                  70                  75                  80 ccg att gca gtg ttg ggt ttc gcc ctg tat gtc cgc agc gca atg gcg     288
Pro Ile Ala Val Leu Gly Phe Ala Leu Tyr Val Arg Ser Ala Met Ala
                 85                  90                  95 tgg gtg gtg atg ctc atc gtg ttc ttc acc ctg agc ctg cac cca gtc     336
Trp Val Val Met Leu Ile Val Phe Phe Thr Leu Ser Leu His Pro Val
            100                 105                 110 ccg cgc atc cat gat atg gtt cat tcc cca ttg aat cac ttc ata ttc     384
Pro Arg Ile His Asp Met Val His Ser Pro Leu Asn His Phe Ile Phe
        115                 120                 125 aag tac ttc agt cta aaa atg gcg agt gat gca cca ctg gat agt gct     432
Lys Tyr Phe Ser Leu Lys Met Ala Ser Asp Ala Pro Leu Asp Ser Ala
    130                 135                 140 ggg cgc tat att ttt gtc gct ccg cca cat ggc gtg ctg cct atg ggg     480
Gly Arg Tyr Ile Phe Val Ala Pro Pro His Gly Val Leu Pro Met Gly
145                 150                 155                 160 aat ctt atg acg gtg cac gcg atg aag gcg tgt ggt gga ttg gag ttc     528
Asn Leu Met Thr Val His Ala Met Lys Ala Cys Gly Gly Leu Glu Phe
                165                 170                 175 cgt ggg ctg acg act gat gtc gcg ctt agg ctg cct ttg ttt cga cac     576
Arg Gly Leu Thr Thr Asp Val Ala Leu Arg Leu Pro Leu Phe Arg His
            180                 185                 190 tat tta ggc gct att ggt act att gcc gcg acg agg cac gtg gcg aag     624
Tyr Leu Gly Ala Ile Gly Thr Ile Ala Ala Thr Arg His Val Ala Lys
        195                 200                 205 cag tac ctc gac aaa gga tgg tca ata ggt ata tct tcg ggc gga gtc     672
Gln Tyr Leu Asp Lys Gly Trp Ser Ile Gly Ile Ser Ser Gly Gly Val
    210                 215                 220 gcg gag att ttc gaa gtt aac aat aag gat gag gtg gtg ttg atg aag     720
Ala Glu Ile Phe Glu Val Asn Asn Lys Asp Glu Val Val Leu Met Lys
225                 230                 235                 240 gag cga aag ggc ttt gtg aag ctt gcc ctt cgc acg ggg act ccg ttg     768
Glu Arg Lys Gly Phe Val Lys Leu Ala Leu Arg Thr Gly Thr Pro Leu
                245                 250                 255 gta gct tgt tat att ttt ggg aat acc aag ctg ttg tcg gcg tgg tat     816
Val Ala Cys Tyr Ile Phe Gly Asn Thr Lys Leu Leu Ser Ala Trp Tyr
            260                 265                 270 gat gat ggg ggg gtg ttg gag ggc ctg tcg cgt tat ttg aaa tgt ggt     864
Asp Asp Gly Gly Val Leu Glu Gly Leu Ser Arg Tyr Leu Lys Cys Gly
        275                 280                 285 gta ttg cca ctt tgg ggt cgc ttt ggt ttg ccg ctt atg cac cgt cat     912
Val Leu Pro Leu Trp Gly Arg Phe Gly Leu Pro Leu Met His Arg His
```

```
                   290                  295                 300
cct gta ttg ggc gcg atg gca aag ccg atc gta gtt ccc aag gtg gag     960
Pro Val Leu Gly Ala Met Ala Lys Pro Ile Val Val Pro Lys Val Glu
305                 310                 315                 320 gga gag ccc acg cag gag atg att gat gag tac cat agt ctc ttc tgt    1008
Gly Glu Pro Thr Gln Glu Met Ile Asp Glu Tyr His Ser Leu Phe Cys
                325                 330                 335 cag acg ctg gtc gat cta ttt gat aga tac aag acc ttg tat ggc tgg    1056
Gln Thr Leu Val Asp Leu Phe Asp Arg Tyr Lys Thr Leu Tyr Gly Trp
            340                 345                 350 ccg gac aag aag ctg ctt att aag tga                                1083
Pro Asp Lys Lys Leu Leu Ile Lys
        355                 360

<210> SEQ ID NO 30
<211> LENGTH: 1692
<212> TYPE: DNA
<213> ORGANISM: Nannochloropsis sp.
<220> FEATURE:
<221> NAME/KEY: CDS
<222> LOCATION: (1)..(1689)

<400> SEQUENCE: 30 atg cta ttg cag gga tta agc tgg tct ttt ttg acg ctg tcc att gtg      48
Met Leu Leu Gln Gly Leu Ser Trp Ser Phe Leu Thr Leu Ser Ile Val
1               5                   10                  15 gta gaa atc ttg ttt gtt atc tcg acg ttt gcg gtg ggg ttt gag ttg      96
Val Glu Ile Leu Phe Val Ile Ser Thr Phe Ala Val Gly Phe Glu Leu
                20                  25                  30 ttt gtg gga gcg gct gtg gta gcg ggc ggc ttc ttt ttg gtc tcg gaa     144
Phe Val Gly Ala Ala Val Val Ala Gly Gly Phe Phe Leu Val Ser Glu
            35                  40                  45 gtg ttg atg att gtg agc ttg cat ttt tac atg cct acg acg act acg     192
Val Leu Met Ile Val Ser Leu His Phe Tyr Met Pro Thr Thr Thr Thr
        50                  55                  60 act gtg acc act acg gga ttg acg gtg atg gag aag aag gtg gag gag     240
Thr Val Thr Thr Thr Gly Leu Thr Val Met Glu Lys Lys Val Glu Glu
65                  70                  75                  80 gtg gag gag atg ttg gtg gag agg gag gga gtg gag aag gac gag atg     288
Val Glu Glu Met Leu Val Glu Arg Glu Gly Val Glu Lys Asp Glu Met
                85                  90                  95 atg atg gag gaa aag gtg gac gtg acg aca gcg gcg acg aca aac gct     336
Met Met Glu Glu Lys Val Asp Val Thr Thr Ala Ala Thr Thr Asn Ala
            100                 105                 110 ctc cta aga acc gga aag cag cgg ctg ctc ttg gcc aaa gaa agt gct     384
Leu Leu Arg Thr Gly Lys Gln Arg Leu Leu Leu Ala Lys Glu Ser Ala
        115                 120                 125 acg aca act act acc gtg aca atg acc acg gag cag acc agc aag          432
Thr Thr Thr Thr Thr Val Thr Met Thr Thr Glu Gln Thr Ser Lys
130                 135                 140 acg tct act tca ttt atg cct gtc cgg gtc gac gag gct tcc ctt gag     480
Thr Ser Thr Ser Phe Met Pro Val Arg Val Asp Glu Ala Ser Leu Glu
145                 150                 155                 160 caa ttc cgc cgg ctc acc gtt ata acc gtt ctg agc aac atg caa tac     528
Gln Phe Arg Arg Leu Thr Val Ile Thr Val Leu Ser Asn Met Gln Tyr
                165                 170                 175 ctg ccc ttc ctc ctt ccc atc ctt ccc ttt att ctc tcc ggt ctc cct     576
Leu Pro Phe Leu Leu Pro Ile Leu Pro Phe Ile Leu Ser Gly Leu Pro
            180                 185                 190 ctc cct gtg gca tct ttg cac tgg ttc ggg gct ttt tgt tgt ctg aca     624
Leu Pro Val Ala Ser Leu His Trp Phe Gly Ala Phe Cys Cys Leu Thr
```

-continued

```
              195                 200                 205
tca gca gtc gtt ttg aat gcc tat gtc aaa acc acg ttg gcc aaa gcg    672
Ser Ala Val Val Leu Asn Ala Tyr Val Lys Thr Thr Leu Ala Lys Ala
210                 215                 220 ggg cat cgt ctt aac tcc ttc cag cgc tcc ctt ctt cat gcc ctc ccc    720
Gly His Arg Leu Asn Ser Phe Gln Arg Ser Leu Leu His Ala Leu Pro
225                 230                 235                 240 tcg ctc att tat gca gcc ccg ggc gtt att tgc ttt ttt gcg tgg aag    768
Ser Leu Ile Tyr Ala Ala Pro Gly Val Ile Cys Phe Phe Ala Trp Lys
                245                 250                 255 caa cac caa ggt ggg agg ggg gac ggg aag cag ggc gcg gtg tcc gcg    816
Gln His Gln Gly Gly Arg Gly Asp Gly Lys Gln Gly Ala Val Ser Ala
                260                 265                 270 ttc ccg gct tgg gcg gtg ctc acg gcc atg cat tat ctg tac ctt ttt    864
Phe Pro Ala Trp Ala Val Leu Thr Ala Met His Tyr Leu Tyr Leu Phe
            275                 280                 285 ctc acg ttt cgc gga aaa ccg gaa gtg acg gga gag aga tat ttg ggc    912
Leu Thr Phe Arg Gly Lys Pro Glu Val Thr Gly Glu Arg Tyr Leu Gly
        290                 295                 300 gaa aag tta gag ttg tgg aaa ggc ggt tgg tct ctt tac tat ttt ttg    960
Glu Lys Leu Glu Leu Trp Lys Gly Gly Trp Ser Leu Tyr Tyr Phe Leu
305                 310                 315                 320 gaa ggg ata gat caa tat ttt cag gcg agg ttt gtt ttt atg gac ccg   1008
Glu Gly Ile Asp Gln Tyr Phe Gln Ala Arg Phe Val Phe Met Asp Pro
                325                 330                 335 aat ctg gat ctg aag ggg aaa ccg cat gtg ttg gcg ttt cac ccg cat   1056
Asn Leu Asp Leu Lys Gly Lys Pro His Val Leu Ala Phe His Pro His
                340                 345                 350 gga gtt cag cca ttt acg acg tgt tgg att caa ctt tcg cgg gcc tgg   1104
Gly Val Gln Pro Phe Thr Thr Cys Trp Ile Gln Leu Ser Arg Ala Trp
            355                 360                 365 aga gag ggg gtg ggg aaa gga cag agg ttt tgt gta atg act gcg agt   1152
Arg Glu Gly Val Gly Lys Gly Gln Arg Phe Cys Val Met Thr Ala Ser
        370                 375                 380 gtc atg cac tat gtg cct ttg atg cgc gat att cta cag tgg ctc ggg   1200
Val Met His Tyr Val Pro Leu Met Arg Asp Ile Leu Gln Trp Leu Gly
385                 390                 395                 400 ggg cgg gaa gtg agc agg gaa gcc att tcg tac gca ctg ggc cgt cga   1248
Gly Arg Glu Val Ser Arg Glu Ala Ile Ser Tyr Ala Leu Gly Arg Arg
                405                 410                 415 gag tct gtg cta ttg gtc cca ggc gga cag caa gag atg atg gag tcc   1296
Glu Ser Val Leu Leu Val Pro Gly Gly Gln Gln Glu Met Met Glu Ser
                420                 425                 430 caa tct cag atg ggc gaa att cgg atc atc acg aag cac gtc ggc ttt   1344
Gln Ser Gln Met Gly Glu Ile Arg Ile Ile Thr Lys His Val Gly Phe
            435                 440                 445 att aga tta gcg ctc caa aca ggc gca ccg ctc gtg cct gtg ctc tca   1392
Ile Arg Leu Ala Leu Gln Thr Gly Ala Pro Leu Val Pro Val Leu Ser
        450                 455                 460 ttt ggc gaa gtt gaa gtg atg gac ttt gtc cgg tac ccg cgt cta cag   1440
Phe Gly Glu Val Glu Val Met Asp Phe Val Arg Tyr Pro Arg Leu Gln
465                 470                 475                 480 cgt ttc ttt atc tcg cgc att ggt atc ccg gtt ccc ttc ttt cca tac   1488
Arg Phe Phe Ile Ser Arg Ile Gly Ile Pro Val Pro Phe Phe Pro Tyr
                485                 490                 495 gga ttg ttt gga ttt ccc atc ccg agg ccc gtg ccc gtg acg gtc gta   1536
Gly Leu Phe Gly Phe Pro Ile Pro Arg Pro Val Pro Val Thr Val Val
                500                 505                 510 ttt ggc cgg ccc att cca gtg gag aag gtt gag cag ccg acg cag gaa   1584
```

| | | | | | | | | | | | | | | | |
|---|---|---|---|---|---|---|---|---|---|---|---|---|---|---|---|
| Phe | Gly | Arg | Pro | Ile | Pro | Val | Glu | Lys | Val | Glu | Gln | Pro | Thr | Gln | Glu |
| | | 515 | | | | 520 | | | | 525 | | | | | |

```
gag gtt cga aaa ttg tcg aaa aag tac ttt gaa agt att cag gag gtg        1632
Glu Val Arg Lys Leu Ser Lys Lys Tyr Phe Glu Ser Ile Gln Glu Val
        530                 535                 540 ttt gat aaa aat aag act gag gcc cta ggg cat ggg aat cat agg ctg        1680
Phe Asp Lys Asn Lys Thr Glu Ala Leu Gly His Gly Asn His Arg Leu
545                 550                 555                 560 gtc ctg ttg taa                                                        1692
Val Leu Leu
```

<210> SEQ ID NO 31
<211> LENGTH: 972
<212> TYPE: DNA
<213> ORGANISM: Nannochloropsis sp.
<220> FEATURE:
<221> NAME/KEY: CDS
<222> LOCATION: (1)..(969)

<400> SEQUENCE: 31

```
atg acg ata gcc atg gcc aca acc tcg tcg cct aaa cat cct ccg cct          48
Met Thr Ile Ala Met Ala Thr Thr Ser Ser Pro Lys His Pro Pro Pro
  1               5                  10                  15 gat ctg aag gaa cgc ctt att ggg ggg tta ctc ctc gct tcg cta atc         96
Asp Leu Lys Glu Arg Leu Ile Gly Gly Leu Leu Leu Ala Ser Leu Ile
             20                  25                  30 cat gta tgg ctc ttt ggt gtc atc gtt gta ccc ttg gcc atg tac cag        144
His Val Trp Leu Phe Gly Val Ile Val Val Pro Leu Ala Met Tyr Gln
         35                  40                  45 ttg ctg gca cag ggc gac tac cgc atc gcc ctt ggc ctc ctc ctt tat        192
Leu Leu Ala Gln Gly Asp Tyr Arg Ile Ala Leu Gly Leu Leu Leu Tyr
 50                  55                  60 tac gcc tac cgc tcg gtc ttt ccg acg aag gaa tgg ggc atc gtt cgc        240
Tyr Ala Tyr Arg Ser Val Phe Pro Thr Lys Glu Trp Gly Ile Val Arg
 65                  70                  75                  80 aac atc tat aga gca ggc aac cga tat ttc tac cca caa gag gtc att        288
Asn Ile Tyr Arg Ala Gly Asn Arg Tyr Phe Tyr Pro Gln Glu Val Ile
                 85                  90                  95 ttt gat ggc ttc aat gag atc aaa ccc gat tcg agg tca ttg att tgc        336
Phe Asp Gly Phe Asn Glu Ile Lys Pro Asp Ser Arg Ser Leu Ile Cys
            100                 105                 110 atg cac ccg cac ggg atc ttg acg att ggt tgg gcg ttg acc agc acg        384
Met His Pro His Gly Ile Leu Thr Ile Gly Trp Ala Leu Thr Ser Thr
        115                 120                 125 agt ccg acc atg gcg cac gcc aac gtg aag tgg ctg gtg aca gaa gct        432
Ser Pro Thr Met Ala His Ala Asn Val Lys Trp Leu Val Thr Glu Ala
    130                 135                 140 ttg ttg cgg ctg cct ttt atc agc gac ttc ctc tcc tgg aac ggt tgt        480
Leu Leu Arg Leu Pro Phe Ile Ser Asp Phe Leu Ser Trp Asn Gly Cys
145                 150                 155                 160 gca cac gcc agc aag agc tac atg caa aat cgt atg acg aag ggt gcg        528
Ala His Ala Ser Lys Ser Tyr Met Gln Asn Arg Met Thr Lys Gly Ala
                165                 170                 175 aat ctt gct ctg ctc ccc ggc gga ttt gaa gag gct tct ctc tat caa        576
Asn Leu Ala Leu Leu Pro Gly Gly Phe Glu Glu Ala Ser Leu Tyr Gln
            180                 185                 190 cgc aac act tat cgt gtt tac gtc aga aag cgc aca ggc ttt att gtg        624
Arg Asn Thr Tyr Arg Val Tyr Val Arg Lys Arg Thr Gly Phe Ile Val
        195                 200                 205 tat gcc ctc agg tat ggg tac aag att tac cca tcg ttc gtc ttt ggg        672
Tyr Ala Leu Arg Tyr Gly Tyr Lys Ile Tyr Pro Ser Phe Val Phe Gly
```

```
                    210                 215                 220
gag gaa aag tgt tat ttc tcc ttg ata ccc gac tgg ggt tgg ctg aca       720
Glu Glu Lys Cys Tyr Phe Ser Leu Ile Pro Asp Trp Gly Trp Leu Thr
225                 230                 235                 240 gcg acc agg tta tgg ttg aac cag tac cgg ata ccg gca gtt gcg ttc       768
Ala Thr Arg Leu Trp Leu Asn Gln Tyr Arg Ile Pro Ala Val Ala Phe
                245                 250                 255 gtc gga aag tta ttt ttg gtt cct ggt tgg gat tca cat ttg ata acg       816
Val Gly Lys Leu Phe Leu Val Pro Gly Trp Asp Ser His Leu Ile Thr
                260                 265                 270 gtg atc ggc gcc ccc gtg gtg ttg ccg agg ctg gac aag ccg act gag       864
Val Ile Gly Ala Pro Val Val Leu Pro Arg Leu Asp Lys Pro Thr Glu
                275                 280                 285 gag gag gtg ggg aaa tac cat tta atg tat gtg agt gca ttg atg gaa       912
Glu Glu Val Gly Lys Tyr His Leu Met Tyr Val Ser Ala Leu Met Glu
290                 295                 300 tta ttc gag aag cac aaa cgg caa tat tgt gaa aag ggg gcg aag ttg       960
Leu Phe Glu Lys His Lys Arg Gln Tyr Cys Glu Lys Gly Ala Lys Leu
305                 310                 315                 320 gag ttg tgg tag                                                        972
Glu Leu Trp <210> SEQ ID NO 32
<211> LENGTH: 1026
<212> TYPE: DNA
<213> ORGANISM: Nannochloropsis sp.
<220> FEATURE:
<221> NAME/KEY: CDS
<222> LOCATION: (1)..(1023)

<400> SEQUENCE: 32 atg aca tcc tcc cca cca gcc tca cca tct gca cct gag aat ccc tat        48
Met Thr Ser Ser Pro Pro Ala Ser Pro Ser Ala Pro Glu Asn Pro Tyr
1               5                   10                  15 aac cta ttg cca cct aag cgg cca aat ccg cag tac tgg cgg tat gca        96
Asn Leu Leu Pro Pro Lys Arg Pro Asn Pro Gln Tyr Trp Arg Tyr Ala
                20                  25                  30 agc ctg acc gct ttc att ctc att tgc ttc caa gcc cct tca agt gac       144
Ser Leu Thr Ala Phe Ile Leu Ile Cys Phe Gln Ala Pro Ser Ser Asp
            35                  40                  45 tcg tgg ggc acc gcc ctc cgc cgc gcc tgc tgg gcg gcg tac tgg atg       192
Ser Trp Gly Thr Ala Leu Arg Arg Ala Cys Trp Ala Ala Tyr Trp Met
    50                  55                  60 acc tac ctg gac aca agc tat aag gat ggc tca cgg gcc tgg ccc tgg       240
Thr Tyr Leu Asp Thr Ser Tyr Lys Asp Gly Ser Arg Ala Trp Pro Trp
65                  70                  75                  80 ttt cag cgc tta agg atc tgg cgt ttg tac tgc ggc tat tta cag ggc       288
Phe Gln Arg Leu Arg Ile Trp Arg Leu Tyr Cys Gly Tyr Leu Gln Gly
                85                  90                  95 aaa gta att tgt acg gtg ccc ttg gac ccg gca cag caa ttc atc ttc       336
Lys Val Ile Cys Thr Val Pro Leu Asp Pro Ala Gln Gln Phe Ile Phe
                100                 105                 110 gca gct cat ccc cac ggc att ggc acc tgg aat cat ttc cta acc atg       384
Ala Ala His Pro His Gly Ile Gly Thr Trp Asn His Phe Leu Thr Met
            115                 120                 125 act gac ggc tgt cgc ttc ctc tcc tca tcc tac ccc cgc ccg cgg ctc       432
Thr Asp Gly Cys Arg Phe Leu Ser Ser Ser Tyr Pro Arg Pro Arg Leu
    130                 135                 140 gac ctg ggt gcg acg gta ctt ttc ttc atc ccc ttc tta aag gaa att       480
Asp Leu Gly Ala Thr Val Leu Phe Phe Ile Pro Phe Leu Lys Glu Ile
145                 150                 155                 160
```

```
ctg ctc tgg ctg ggc tgt gtg gat gct gga gcg tcc acg gcc cac gca      528
Leu Leu Trp Leu Gly Cys Val Asp Ala Gly Ala Ser Thr Ala His Ala
            165                 170                 175 atc ttg gcg cgg ggc tac tca tcc ctc att tac att ggt gga gaa aag      576
Ile Leu Ala Arg Gly Tyr Ser Ser Leu Ile Tyr Ile Gly Gly Glu Lys
        180                 185                 190 gag cag att tta acg cag cga ggc aaa gac atc gtg gtg gta cgt ccc      624
Glu Gln Ile Leu Thr Gln Arg Gly Lys Asp Ile Val Val Val Arg Pro
    195                 200                 205 cgc aag ggt ttt tgc cag ctg gcc ctg caa cat gac tgc ccc atc gta      672
Arg Lys Gly Phe Cys Gln Leu Ala Leu Gln His Asp Cys Pro Ile Val
210                 215                 220 ccc gtc tac gcg ttt ggg gag aac gat ctc tat cgc aca ttc aac cac      720
Pro Val Tyr Ala Phe Gly Glu Asn Asp Leu Tyr Arg Thr Phe Asn His
225                 230                 235                 240 ctg aag gac gtc caa ctg tgg gtg gcc agc acc ttt aag ctg gct ttt      768
Leu Lys Asp Val Gln Leu Trp Val Ala Ser Thr Phe Lys Leu Ala Phe
            245                 250                 255 cct cct tgt tgg ggc gtc ccc ttc ctc ccc ttc ctc cct ctg cca gtc      816
Pro Pro Cys Trp Gly Val Pro Phe Leu Pro Phe Leu Pro Leu Pro Val
        260                 265                 270 ccc gtc acg gtg gtg atg ggc gaa ccc ttg cgg ccc aga aca gga gaa      864
Pro Val Thr Val Val Met Gly Glu Pro Leu Arg Pro Arg Thr Gly Glu
    275                 280                 285 gga aag gag gga agg gct ggt gga gaa aaa gga gtg aag ccc aca agg      912
Gly Lys Glu Gly Arg Ala Gly Gly Glu Lys Gly Val Lys Pro Thr Arg
290                 295                 300 gag gag gtg gac gag ctg cac acc cgg tac gtg gag gcc ctg cag agg      960
Glu Glu Val Asp Glu Leu His Thr Arg Tyr Val Glu Ala Leu Gln Arg
305                 310                 315                 320 ttg ttc gac gca cac aag ggc agg cac ggg ggg agg agc gaa gag gcc     1008
Leu Phe Asp Ala His Lys Gly Arg His Gly Gly Arg Ser Glu Glu Ala
            325                 330                 335 acc tta gtg gtc agg tga                                             1026
Thr Leu Val Val Arg
            340

<210> SEQ ID NO 33
<211> LENGTH: 1464
<212> TYPE: DNA
<213> ORGANISM: Nannochloropsis sp.
<220> FEATURE:
<221> NAME/KEY: CDS
<222> LOCATION: (1)..(1461)

<400> SEQUENCE: 33 atg gct cac ctc ttc cgt cgt aga agc aaa ggc gag ggc aac agc act       48
Met Ala His Leu Phe Arg Arg Arg Ser Lys Gly Glu Gly Asn Ser Thr
1               5                   10                  15 agc agc cgc tgc tta tct tta tcg gaa ggc aat aag gcc atg tta atc       96
Ser Ser Arg Cys Leu Ser Leu Ser Glu Gly Asn Lys Ala Met Leu Ile
            20                  25                  30 ctc tct tcc gaa atc gag ccg ccc gct tcc gcc acg tcc aaa gcc gcg      144
Leu Ser Ser Glu Ile Glu Pro Pro Ala Ser Ala Thr Ser Lys Ala Ala
        35                  40                  45 aca agc ggc atc aaa gag att ggg gac ccg tca ttg ccc acc gtc gca      192
Thr Ser Gly Ile Lys Glu Ile Gly Asp Pro Ser Leu Pro Thr Val Ala
    50                  55                  60 cta tta tca cta cct agc ata agc aag gca gat aca aat tcc gcc act      240
Leu Leu Ser Leu Pro Ser Ile Ser Lys Ala Asp Thr Asn Ser Ala Thr
65                  70                  75                  80
```

```
gct gca gta gca gca gga aca ctg gag gat gca gca gca ggc gcc ctg         288
Ala Ala Val Ala Ala Gly Thr Leu Glu Asp Ala Ala Ala Gly Ala Leu
                    85                  90                  95 aca gct cca ttc gcc gac cga tct gtg aag aag caa tac ggg cag gat         336
Thr Ala Pro Phe Ala Asp Arg Ser Val Lys Lys Gln Tyr Gly Gln Asp
                100                 105                 110 ggt gat ggg gcg cag tgt aag gag gca gaa ggt gga cga aaa cgc agt         384
Gly Asp Gly Ala Gln Cys Lys Glu Ala Glu Gly Gly Arg Lys Arg Ser
            115                 120                 125 gga agc gtt ggt aat ctc cta ctg tct tct atg act tcg ttt tct aaa         432
Gly Ser Val Gly Asn Leu Leu Leu Ser Ser Met Thr Ser Phe Ser Lys
        130                 135                 140 ggc acg tcc ctt tcc ttc ttg acc ggc gag gac aag aca ccg tct cct         480
Gly Thr Ser Leu Ser Phe Leu Thr Gly Glu Asp Lys Thr Pro Ser Pro
145                 150                 155                 160 cct gag aca ggg cct gct ggg att gat ttc tcg aca ccg gcg cac cca         528
Pro Glu Thr Gly Pro Ala Gly Ile Asp Phe Ser Thr Pro Ala His Pro
                165                 170                 175 acg atg caa ttc gtg gac ttt atc atc acc ttt ctc ttg gtg cac tac         576
Thr Met Gln Phe Val Asp Phe Ile Ile Thr Phe Leu Leu Val His Tyr
                180                 185                 190 att caa gtc ttc tac tcc ctc gtg ttc ctc ttc atc tac ctc gtc aag         624
Ile Gln Val Phe Tyr Ser Leu Val Phe Leu Phe Ile Tyr Leu Val Lys
            195                 200                 205 cac ggt cac cga tgg ccg tat ttc ctc gct gcc atc tac gcg cct tcc         672
His Gly His Arg Trp Pro Tyr Phe Leu Ala Ala Ile Tyr Ala Pro Ser
        210                 215                 220 tac ttc att cct ttg cag cgc ttg ggg gga tgg ccg ttc aaa gga ttc         720
Tyr Phe Ile Pro Leu Gln Arg Leu Gly Gly Trp Pro Phe Lys Gly Phe
225                 230                 235                 240 atg cgc cgc ccc ttc tgg cgg tgt gtg cag cgg acc ctt gct ctc cag         768
Met Arg Arg Pro Phe Trp Arg Cys Val Gln Arg Thr Leu Ala Leu Gln
                245                 250                 255 gtg gag aga gag gtt gag cta agc ccg gac gaa caa tac atc ttt ggt         816
Val Glu Arg Glu Val Glu Leu Ser Pro Asp Glu Gln Tyr Ile Phe Gly
                260                 265                 270 tgg cac ccc cac ggg atc ttg ctg ttg tcc cgg ttt gcc atc tat ggg         864
Trp His Pro His Gly Ile Leu Leu Leu Ser Arg Phe Ala Ile Tyr Gly
            275                 280                 285 ggt ctg tgg gag aag ctc ttt ccg ggt ata cat ttt aag acg ctg gct         912
Gly Leu Trp Glu Lys Leu Phe Pro Gly Ile His Phe Lys Thr Leu Ala
        290                 295                 300 gca agt cct cta ttt tgg att cca cct att cgc gag gtg tcg atc ttg         960
Ala Ser Pro Leu Phe Trp Ile Pro Pro Ile Arg Glu Val Ser Ile Leu
305                 310                 315                 320 ctg ggg ggg gta gat gca ggc agg gca tcc gca gca cgg gcg ctt acg        1008
Leu Gly Gly Val Asp Ala Gly Arg Ala Ser Ala Ala Arg Ala Leu Thr
                325                 330                 335 gac ggc tac tcc gtt tct ctt tat ccg ggg gga agc aag gaa atc tac        1056
Asp Gly Tyr Ser Val Ser Leu Tyr Pro Gly Gly Ser Lys Glu Ile Tyr
                340                 345                 350 acc acc gac ccc tac act cct gaa acg acc ctg gtc ctt aaa atc cgc        1104
Thr Thr Asp Pro Tyr Thr Pro Glu Thr Thr Leu Val Leu Lys Ile Arg
            355                 360                 365 aaa ggc ttc att cgc atg gcc ctc cgg tat ggc tgt gcc ctt gtc ccg        1152
Lys Gly Phe Ile Arg Met Ala Leu Arg Tyr Gly Cys Ala Leu Val Pro
        370                 375                 380 gtg tac acg ttt gga gaa aaa tat gcc tat cat cgt cta ggg caa gcc        1200
Val Tyr Thr Phe Gly Glu Lys Tyr Ala Tyr His Arg Leu Gly Gln Ala
```

```
                            385                390                395                400
aca ggc ttc gcg cgc tgg ctg ctg gcg gtg cta aaa gtg cca ttt ttg      1248
Thr Gly Phe Ala Arg Trp Leu Leu Ala Val Leu Lys Val Pro Phe Leu
                            405                410                415 atc ttt tgg gga cga tgg gga acg ttc atg ccg ctc aag gag acg cag      1296
Ile Phe Trp Gly Arg Trp Gly Thr Phe Met Pro Leu Lys Glu Thr Gln
                    420                425                430 gta tcg gtg gtg gtg ggc acg ccg ttg cgg gtg ccc aaa atc gag gga      1344
Val Ser Val Val Val Gly Thr Pro Leu Arg Val Pro Lys Ile Glu Gly
                435                440                445 gaa ccc tcc ccg gag gtg gtg gaa gag tgg ctg cag aaa tac tgt gat      1392
Glu Pro Ser Pro Glu Val Val Glu Glu Trp Leu Gln Lys Tyr Cys Asp
450                455                460 gaa gtc caa gca ctg ttc agg cgg cac aag cat aaa tac gcg aag ccc      1440
Glu Val Gln Ala Leu Phe Arg Arg His Lys His Lys Tyr Ala Lys Pro
465                470                475                480 gag gag ttc gtt gcg atc tct tga                                      1464
Glu Glu Phe Val Ala Ile Ser
                485

<210> SEQ ID NO 34
<211> LENGTH: 1029
<212> TYPE: DNA
<213> ORGANISM: Nannochloropsis sp.
<220> FEATURE:
<221> NAME/KEY: CDS
<222> LOCATION: (1)..(1026)

<400> SEQUENCE: 34 atg ttg ctg gcg tcg tct cgg cgg ccg gca tcg tcc ttg gtg gat cct      48
Met Leu Leu Ala Ser Ser Arg Arg Pro Ala Ser Ser Leu Val Asp Pro
1               5                   10                  15 ttg cca tta acg ggg aaa ctg cct acc ggg gca atc agg ctt ttc acg      96
Leu Pro Leu Thr Gly Lys Leu Pro Thr Gly Ala Ile Arg Leu Phe Thr
                20                  25                  30 tcc cgg cct gct tcc tgg cgt aca act ccc atg gtg gtg ggc ggg tcc      144
Ser Arg Pro Ala Ser Trp Arg Thr Thr Pro Met Val Val Gly Gly Ser
            35                  40                  45 ttg ctg gtg gtg gga tca ttc gtc tgg gta ccc cta gtt atc tgg ctg      192
Leu Leu Val Val Gly Ser Phe Val Trp Val Pro Leu Val Ile Trp Leu
        50                  55                  60 ggt tgg agg aaa tgt gag aca cgg aag cga cgc atc atc tat gtc ctt      240
Gly Trp Arg Lys Cys Glu Thr Arg Lys Arg Arg Ile Ile Tyr Val Leu
65                  70                  75                  80 gtt ttg tgt gtt gtt ctg act cta cct aca cga cgg tgg gac gcg gtg      288
Val Leu Cys Val Val Leu Thr Leu Pro Thr Arg Arg Trp Asp Ala Val
                85                  90                  95 gtc ttg aac ggc ctc tgg agc cgt ttt gtg gaa tat ttt tca gtc gag      336
Val Leu Asn Gly Leu Trp Ser Arg Phe Val Glu Tyr Phe Ser Val Glu
            100                 105                 110 gtg gtg ggg gac gac ccc ttg ccc aag gac cgc tct gcg gtc tac gcc      384
Val Val Gly Asp Asp Pro Leu Pro Lys Asp Arg Ser Ala Val Tyr Ala
        115                 120                 125 gtc att cct cac ggc acc ttc ccc ttt ggt ctc ggc gtg gtc tcc ctc      432
Val Ile Pro His Gly Thr Phe Pro Phe Gly Leu Gly Val Val Ser Leu
    130                 135                 140 ggt ccc ttg aac aag atc ttc aat aag gtt cgg ccc gtg gtg gcc tcg      480
Gly Pro Leu Asn Lys Ile Phe Asn Lys Val Arg Pro Val Val Ala Ser
145                 150                 155                 160 gcc gtc ttg cgc ttt ccg ggc ttc ggc caa ctt ata ggc ttc gcc ggc      528
Ala Val Leu Arg Phe Pro Gly Phe Gly Gln Leu Ile Gly Phe Ala Gly
```

-continued

```
                    165                 170                 175
ggg gta gat gca ggg cct aat gaa gta agc aag gcc atc aag gag ggc     576
Gly Val Asp Ala Gly Pro Asn Glu Val Ser Lys Ala Ile Lys Glu Gly
                180                 185                 190 tgt tca gtg agt atc tgt ccg ggg ggc atc gca gag atg ttc tgg gga     624
Cys Ser Val Ser Ile Cys Pro Gly Gly Ile Ala Glu Met Phe Trp Gly
            195                 200                 205 tat cca aag gag ggc tgc tta ccg cgg gag gaa tac gcg ttc ttg cag     672
Tyr Pro Lys Glu Gly Cys Leu Pro Arg Glu Glu Tyr Ala Phe Leu Gln
        210                 215                 220 tcg agg aaa ggg ttt ata cga atg gcc atg aaa cat aat gtg cct gtg     720
Ser Arg Lys Gly Phe Ile Arg Met Ala Met Lys His Asn Val Pro Val
225                 230                 235                 240 atc cct gta tac tgt ttt ggt aac acc cat gcg atg cat aag gct aag     768
Ile Pro Val Tyr Cys Phe Gly Asn Thr His Ala Met His Lys Ala Lys
                245                 250                 255 acg cct tgg gtc ttg gag gcg ctc tca agg ctt ctg aag acc tct ctc     816
Thr Pro Trp Val Leu Glu Ala Leu Ser Arg Leu Leu Lys Thr Ser Leu
            260                 265                 270 ata ttg act tgg ggc cgg tgg ggg ctg ccc att ccc tac cgt gtg cct     864
Ile Leu Thr Trp Gly Arg Trp Gly Leu Pro Ile Pro Tyr Arg Val Pro
        275                 280                 285 ctc ctc tat gcc gtc ggc aag ccc ctc cac ctc ctg cat gct gaa aat     912
Leu Leu Tyr Ala Val Gly Lys Pro Leu His Leu Leu His Ala Glu Asn
    290                 295                 300 cca acc cct ggt cag att gag gtg gcg cac gcc gag ttc tgc agg gcc     960
Pro Thr Pro Gly Gln Ile Glu Val Ala His Ala Glu Phe Cys Arg Ala
305                 310                 315                 320 ctt tcg gat ttg ttc gat cgg tac aag ttt tat tat gga tgg ggg cac    1008
Leu Ser Asp Leu Phe Asp Arg Tyr Lys Phe Tyr Tyr Gly Trp Gly His
                325                 330                 335 aag acg ctt cgc atc gtc tga                                        1029
Lys Thr Leu Arg Ile Val
            340

<210> SEQ ID NO 35
<211> LENGTH: 1176
<212> TYPE: DNA
<213> ORGANISM: Nannochloropsis sp.
<220> FEATURE:
<221> NAME/KEY: CDS
<222> LOCATION: (1)..(1173)

<400> SEQUENCE: 35 atg aag aaa atc ttg cgc atc ccg gag tcg ccc atc tcg gac gac acc      48
Met Lys Lys Ile Leu Arg Ile Pro Glu Ser Pro Ile Ser Asp Asp Thr
1               5                   10                  15 ctg gtg aag aat gga ggc aag aag acc gag ctc tcc acg ccg gtc acc      96
Leu Val Lys Asn Gly Gly Lys Lys Thr Glu Leu Ser Thr Pro Val Thr
            20                  25                  30 gct cct acg tcg gac cgc acg cgc atc tac agt gat ggc tat tcg acc     144
Ala Pro Thr Ser Asp Arg Thr Arg Ile Tyr Ser Asp Gly Tyr Ser Thr
        35                  40                  45 ccc aag tcc tac aca ttg gaa gtc gat cca aaa ttt tac aag cga gta     192
Pro Lys Ser Tyr Thr Leu Glu Val Asp Pro Lys Phe Tyr Lys Arg Val
    50                  55                  60 tgt gat gct gac gat gtg tgg aca cgc aca cag ggg gcc ttt gct ctc     240
Cys Asp Ala Asp Asp Val Trp Thr Arg Thr Gln Gly Ala Phe Ala Leu
65                  70                  75                  80 ctc atg ctc tgg ggc gtt tgg ctt gcc ggg tcc ttt tct gtg ttt tgg     288
Leu Met Leu Trp Gly Val Trp Leu Ala Gly Ser Phe Ser Val Phe Trp
```

```
                        85                  90                  95
tgg ccc tat tta gta atg aag ggg tac tac act gca gcc ctt gtc atg        336
Trp Pro Tyr Leu Val Met Lys Gly Tyr Tyr Thr Ala Ala Leu Val Met
            100                 105                 110 gca gtg atc atg gca tat ccg tat gtt gtc aag gtc aag caa agc ccg        384
Ala Val Ile Met Ala Tyr Pro Tyr Val Val Lys Val Lys Gln Ser Pro
            115                 120                 125 gca ttt att cgg ttc atc ttg agc ggc gcg ggt tgg ttt aag ggc ggg        432
Ala Phe Ile Arg Phe Ile Leu Ser Gly Ala Gly Trp Phe Lys Gly Gly
130                 135                 140 act tgt ttg tat ttg gag gag tcg atg aag cag atc gac acc agc gag        480
Thr Cys Leu Tyr Leu Glu Glu Ser Met Lys Gln Ile Asp Thr Ser Glu
145                 150                 155                 160 tct gtc ctc ctc tgc cag cat ccg cac ggt ctc ttc acc tac ggc ttc        528
Ser Val Leu Leu Cys Gln His Pro His Gly Leu Phe Thr Tyr Gly Phe
                165                 170                 175 att cag aac ggg tcc gcc gcc cgc atc gat gcc cgc aaa cca gag gtt        576
Ile Gln Asn Gly Ser Ala Ala Arg Ile Asp Ala Arg Lys Pro Glu Val
            180                 185                 190 tat gtg cct gcc gca ttt cgt cac atg aaa ccc aac gcc aag gcc ttc        624
Tyr Val Pro Ala Ala Phe Arg His Met Lys Pro Asn Ala Lys Ala Phe
            195                 200                 205 gtg gag ccc ttg ctt ttc aaa atc ccg ctc atc cgt cac ttc att acc        672
Val Glu Pro Leu Leu Phe Lys Ile Pro Leu Ile Arg His Phe Ile Thr
210                 215                 220 gcc ttc ggc aat gcc gct ccg gcg aca aag aaa gaa atg cac cgg ctc        720
Ala Phe Gly Asn Ala Ala Pro Ala Thr Lys Lys Glu Met His Arg Leu
225                 230                 235                 240 atg tcc acc aaa att ccc ctg ggg ctt cta ccc ggt ggg tcg gaa gag        768
Met Ser Thr Lys Ile Pro Leu Gly Leu Leu Pro Gly Gly Ser Glu Glu
                245                 250                 255 atc ata cta agc cac cac ggc cat gag cgg gcc tac ata ctt aaa cgg        816
Ile Ile Leu Ser His His Gly His Glu Arg Ala Tyr Ile Leu Lys Arg
            260                 265                 270 aaa ggc ttc ctc aag tac gca tta caa cat ggc tac acg att tgc att        864
Lys Gly Phe Leu Lys Tyr Ala Leu Gln His Gly Tyr Thr Ile Cys Ile
            275                 280                 285 gga tac acg ttc ggg gag tcc gac tcg tac cgc acc ttg gac tgg ggc        912
Gly Tyr Thr Phe Gly Glu Ser Asp Ser Tyr Arg Thr Leu Asp Trp Gly
290                 295                 300 gtg aag ttt cgt atg tgg tat ctg aaa acc ttc cgt gtt cca ctt ttc        960
Val Lys Phe Arg Met Trp Tyr Leu Lys Thr Phe Arg Val Pro Leu Phe
305                 310                 315                 320 gcg tgc tgg ggg att tgg tgg tgt ccc ctc ttg ccg cgg ggg cag gtg        1008
Ala Cys Trp Gly Ile Trp Trp Cys Pro Leu Leu Pro Arg Gly Gln Val
                325                 330                 335 gcg ctt gag aca gtc gtt ggg aac ccg ttt cgg ttg ccc aag atc tca        1056
Ala Leu Glu Thr Val Val Gly Asn Pro Phe Arg Leu Pro Lys Ile Ser
            340                 345                 350 gat ccg agc cag gag gat att gac aag tgg cat gcg gtg tat gtg caa        1104
Asp Pro Ser Gln Glu Asp Ile Asp Lys Trp His Ala Val Tyr Val Gln
            355                 360                 365 aaa ctt gtg gat ctg ttt gat cgg aac aaa gcc aag ttc ggg tat ggg        1152
Lys Leu Val Asp Leu Phe Asp Arg Asn Lys Ala Lys Phe Gly Tyr Gly
370                 375                 380 gac agg gag ctg gag ctt tat tag                                        1176
Asp Arg Glu Leu Glu Leu Tyr
385                 390
```

```
<210> SEQ ID NO 36
<211> LENGTH: 1185
<212> TYPE: DNA
<213> ORGANISM: Nannochloropsis sp.
<220> FEATURE:
<221> NAME/KEY: CDS
<222> LOCATION: (1)..(1182)

<400> SEQUENCE: 36
```

| | | | | | | | | | | | | | | | | |
|---|---|---|---|---|---|---|---|---|---|---|---|---|---|---|---|---|
| atg | ggt | cta | ttt | ggc | agt | ggg | atc | atc | gag | cag | caa | gag | cag | gcg | aag | 48 |
| Met | Gly | Leu | Phe | Gly | Ser | Gly | Ile | Ile | Glu | Gln | Gln | Glu | Gln | Ala | Lys | |
| 1 | | | | 5 | | | | | 10 | | | | | 15 | | |
| ctg | aag | cag | aaa | ccg | tct | ccg | ctg | cgg | gag | ctc | aag | gga | ggc | aat | aaa | 96 |
| Leu | Lys | Gln | Lys | Pro | Ser | Pro | Leu | Arg | Glu | Leu | Lys | Gly | Gly | Asn | Lys | |
| | | | 20 | | | | | 25 | | | | | 30 | | | |
| agc | agc | aag | cac | aag | gaa | ccc | ctg | acg | ccc | tcc | agt | aat | ctg | agg | ccg | 144 |
| Ser | Ser | Lys | His | Lys | Glu | Pro | Leu | Thr | Pro | Ser | Ser | Asn | Leu | Arg | Pro | |
| | | 35 | | | | | 40 | | | | | 45 | | | | |
| gcc | cgc | tcc | ccg | acc | gag | gta | gac | tgg | agc | tct | ttt | ccc | gag | ggc | agc | 192 |
| Ala | Arg | Ser | Pro | Thr | Glu | Val | Asp | Trp | Ser | Ser | Phe | Pro | Glu | Gly | Ser | |
| | 50 | | | | | 55 | | | | | 60 | | | | | |
| tac | acg | cgc | ttc | ggg | cat | ggc | ggg | gat | tgg | tgg | acg | ctg | atc | aag | ggg | 240 |
| Tyr | Thr | Arg | Phe | Gly | His | Gly | Gly | Asp | Trp | Trp | Thr | Leu | Ile | Lys | Gly | |
| 65 | | | | | 70 | | | | | 75 | | | | | 80 | |
| acg | ata | gcc | att | ttg | ttc | acg | tgg | gga | acc | tgg | ctg | gcc | ggc | ggc | ttg | 288 |
| Thr | Ile | Ala | Ile | Leu | Phe | Thr | Trp | Gly | Thr | Trp | Leu | Ala | Gly | Gly | Leu | |
| | | | | 85 | | | | | 90 | | | | | 95 | | |
| tct | ccc | gtt | tgg | atg | act | tgg | ttg | ttt | tgg | cac | gga | tac | aaa | aag | acg | 336 |
| Ser | Pro | Val | Trp | Met | Thr | Trp | Leu | Phe | Trp | His | Gly | Tyr | Lys | Lys | Thr | |
| | | | 100 | | | | | 105 | | | | | 110 | | | |
| ttt | tat | tcg | atc | ttg | ggc | cct | ttg | ctc | tat | ccg | ctt | ttg | ttg | cca | gtg | 384 |
| Phe | Tyr | Ser | Ile | Leu | Gly | Pro | Leu | Leu | Tyr | Pro | Leu | Leu | Leu | Pro | Val | |
| | | 115 | | | | | 120 | | | | | 125 | | | | |
| ccg | gcc | tgg | cct | gga | ttc | gtc | cga | ttc | att | cta | aac | atg | gct | ggg | tat | 432 |
| Pro | Ala | Trp | Pro | Gly | Phe | Val | Arg | Phe | Ile | Leu | Asn | Met | Ala | Gly | Tyr | |
| | 130 | | | | | 135 | | | | | 140 | | | | | |
| ttt | gag | ggc | ggt | gca | gcg | atg | tac | gtt | gaa | aac | tcc | ttc | aaa | ggc | cgc | 480 |
| Phe | Glu | Gly | Gly | Ala | Ala | Met | Tyr | Val | Glu | Asn | Ser | Phe | Lys | Gly | Arg | |
| 145 | | | | | 150 | | | | | 155 | | | | | 160 | |
| aac | gtg | aac | ggc | cct | atc | atg | ttg | gcc | atg | cat | ccc | cac | ggc | atc | atg | 528 |
| Asn | Val | Asn | Gly | Pro | Ile | Met | Leu | Ala | Met | His | Pro | His | Gly | Ile | Met | |
| | | | | 165 | | | | | 170 | | | | | 175 | | |
| cct | cac | tct | ttc | ctt | ctc | aac | ggt | gcc | ggg | cgg | atc | cac | gcg | cag | aaa | 576 |
| Pro | His | Ser | Phe | Leu | Leu | Asn | Gly | Ala | Gly | Arg | Ile | His | Ala | Gln | Lys | |
| | | | 180 | | | | | 185 | | | | | 190 | | | |
| cca | gag | gta | ttc | ctc | cct | cca | cac | tat | caa | gat | atg | tct | ctc | aaa | tcg | 624 |
| Pro | Glu | Val | Phe | Leu | Pro | Pro | His | Tyr | Gln | Asp | Met | Ser | Leu | Lys | Ser | |
| | | 195 | | | | | 200 | | | | | 205 | | | | |
| acg | ggc | gta | gcg | gag | cct | ttg | ttg | ttt | cgg | att | ccg | ttt | atc | tcg | gcg | 672 |
| Thr | Gly | Val | Ala | Glu | Pro | Leu | Leu | Phe | Arg | Ile | Pro | Phe | Ile | Ser | Ala | |
| | 210 | | | | | 215 | | | | | 220 | | | | | |
| ttt | cta | tac | ttt | ttc | gga | tgt | gcc | gaa | cca | gcg | tca | aag | gag | atg | atg | 720 |
| Phe | Leu | Tyr | Phe | Phe | Gly | Cys | Ala | Glu | Pro | Ala | Ser | Lys | Glu | Met | Met | |
| 225 | | | | | 230 | | | | | 235 | | | | | 240 | |
| cac | gac | atc | ttg | ggg | agg | cag | gtg | ccg | ttt | ggg | att | ctg | gtt | ggt | ggc | 768 |
| His | Asp | Ile | Leu | Gly | Arg | Gln | Val | Pro | Phe | Gly | Ile | Leu | Val | Gly | Gly | |
| | | | | 245 | | | | | 250 | | | | | 255 | | |
| tca | gaa | gaa | att | ctc | ctc | atg | gag | tac | cag | aag | gaa | aac | atc | tac | atc | 816 |
| Ser | Glu | Glu | Ile | Leu | Leu | Met | Glu | Tyr | Gln | Lys | Glu | Asn | Ile | Tyr | Ile | |
| | | | 260 | | | | | 265 | | | | | 270 | | | |
| ctg | gaa | cgc | aaa | ggc | ttc | atc | aaa | tac | gcc | ctc | caa | cac | ggc | tac | acc | 864 |

```
                Leu Glu Arg Lys Gly Phe Ile Lys Tyr Ala Leu Gln His Gly Tyr Thr
                            275                 280                 285 att gct att ggc tat ctg ttc ggg gaa tcc aac ctc tac cac acc atc            912
Ile Ala Ile Gly Tyr Leu Phe Gly Glu Ser Asn Leu Tyr His Thr Ile
290                 295                 300 acc tgg ggc cgc aag acc cgc ctc gct ctc ttc aaa aaa ttc aag atc            960
Thr Trp Gly Arg Lys Thr Arg Leu Ala Leu Phe Lys Lys Phe Lys Ile
305                 310                 315                 320 ccc ctc ttc ttg gct tgg ggg cgt tgg ttc ttc ccc tta ctt cct gag           1008
Pro Leu Phe Leu Ala Trp Gly Arg Trp Phe Phe Pro Leu Leu Pro Glu
                325                 330                 335 cga gcc gcg cct ttg aat gct gtc gta ggt aac ccg ata gat ttg ccc           1056
Arg Ala Ala Pro Leu Asn Ala Val Val Gly Asn Pro Ile Asp Leu Pro
            340                 345                 350 agg ata gct aac cca agc cag gcc gac att gac aaa tac cat gcg ttg           1104
Arg Ile Ala Asn Pro Ser Gln Ala Asp Ile Asp Lys Tyr His Ala Leu
        355                 360                 365 tat att gag aag ttg aca gac ttg ttc gaa cgg aat aag gcg gcc ttc           1152
Tyr Ile Glu Lys Leu Thr Asp Leu Phe Glu Arg Asn Lys Ala Ala Phe
370                 375                 380 ggg tat tct gat cgg acg ttg aat ttc ttt tag                               1185
Gly Tyr Ser Asp Arg Thr Leu Asn Phe Phe
385                 390

<210> SEQ ID NO 37
<211> LENGTH: 1227
<212> TYPE: DNA
<213> ORGANISM: Nannochloropsis sp.
<220> FEATURE:
<221> NAME/KEY: CDS
<222> LOCATION: (1)..(1224)

<400> SEQUENCE: 37 atg ggc gct acc acc gag acc cag act aaa aag acg ttt gta atg cgg             48
Met Gly Ala Thr Thr Glu Thr Gln Thr Lys Lys Thr Phe Val Met Arg
1               5                   10                  15 aca gtc gca gta cga aac gag gat ata gcg ctg gaa gca gcg aca gga            96
Thr Val Ala Val Arg Asn Glu Asp Ile Ala Leu Glu Ala Ala Thr Gly
            20                  25                  30 gac ggg gca gca ggg gat gca act gct ggt ggc ctt tca cgc tcg ata           144
Asp Gly Ala Ala Gly Asp Ala Thr Ala Gly Gly Leu Ser Arg Ser Ile
        35                  40                  45 cta aca gag gct ccg gcg gcg tcc act tca ctt tca tcg cga ctg gca           192
Leu Thr Glu Ala Pro Ala Ala Ser Thr Ser Leu Ser Ser Arg Leu Ala
    50                  55                  60 ccg tcc tca gca caa gct tca gct tcg cct ata atg gtt cgg ccc gaa           240
Pro Ser Ser Ala Gln Ala Ser Ala Ser Pro Ile Met Val Arg Pro Glu
65                  70                  75                  80 gca cgc ccc cca ggt cta cta ggc cgt cta caa acg tta ggt gcg gtg           288
Ala Arg Pro Pro Gly Leu Leu Gly Arg Leu Gln Thr Leu Gly Ala Val
                85                  90                  95 gta ttt ttg ggg ctc atg gga tcc tcg ctg tac cta gtg ata gcg tct           336
Val Phe Leu Gly Leu Met Gly Ser Ser Leu Tyr Leu Val Ile Ala Ser
            100                 105                 110 gcg ctt tac atc gtg att ggt ttc ggc gta ttg ggc cac cgt att tgc           384
Ala Leu Tyr Ile Val Ile Gly Phe Gly Val Leu Gly His Arg Ile Cys
        115                 120                 125 cct tcg atc tta ctg ggg gtt tgg gta gga caa ggt cta att tct gtc           432
Pro Ser Ile Leu Leu Gly Val Trp Val Gly Gln Gly Leu Ile Ser Val
    130                 135                 140 aag gtg ctg cac caa gac ccg gaa ggt atc aag cgg tcg tgg ctc ttc           480
```

```
                Lys Val Leu His Gln Asp Pro Glu Gly Ile Lys Arg Ser Trp Leu Phe
                145                 150                 155                 160 cga gaa atg gct aac ttt ttt gat gtg aca ttg gtg atg gag cag aaa         528
Arg Glu Met Ala Asn Phe Phe Asp Val Thr Leu Val Met Glu Gln Lys
                165                 170                 175 ttg gac act tcc aag aag tac ttg ttc gca cag cat ccg cac ggt atc         576
Leu Asp Thr Ser Lys Lys Tyr Leu Phe Ala Gln His Pro His Gly Ile
            180                 185                 190 ctt cct ctc gcc ccc gtg ttg tcc gct tac ttt atc tcg gac gtg gtg         624
Leu Pro Leu Ala Pro Val Leu Ser Ala Tyr Phe Ile Ser Asp Val Val
        195                 200                 205 ccc ggc gga ggc aag att ttc tgt ttg ata cat agc gga atg ttc tac         672
Pro Gly Gly Gly Lys Ile Phe Cys Leu Ile His Ser Gly Met Phe Tyr
    210                 215                 220 ttg ccc atc gtc cga ttt ttc atg ggc gaa tgg ggt gcg ctc ccc gca         720
Leu Pro Ile Val Arg Phe Phe Met Gly Glu Trp Gly Ala Leu Pro Ala
225                 230                 235                 240 aac aag gag tct gtc gcc gaa gcc aag caa caa gga cag cat tgc tcc         768
Asn Lys Glu Ser Val Ala Glu Ala Lys Gln Gln Gly Gln His Cys Ser
                245                 250                 255 atc gtc gtc ggc ggg gtc gca gag att ttc ctt caa aac gga gag acc         816
Ile Val Val Gly Gly Val Ala Glu Ile Phe Leu Gln Asn Gly Glu Thr
            260                 265                 270 gaa caa ctg caa ctc agg aag ggt ttt att cgt gag gcg att cgc aac         864
Glu Gln Leu Gln Leu Arg Lys Gly Phe Ile Arg Glu Ala Ile Arg Asn
        275                 280                 285 gga tat gac ctt gtg ccc atg ttc cat ttt gga gcc acg cgc atg tat         912
Gly Tyr Asp Leu Val Pro Met Phe His Phe Gly Ala Thr Arg Met Tyr
    290                 295                 300 aat ttt atc ggc ccc gcc tca ttt tgg cgg tcc ttg tca aac cgc ctg         960
Asn Phe Ile Gly Pro Ala Ser Phe Trp Arg Ser Leu Ser Asn Arg Leu
305                 310                 315                 320 ccg ttt ccc ttc ttt ctg att ggg gga tgg ggg aaa gga atg acc ctg        1008
Pro Phe Pro Phe Phe Leu Ile Gly Gly Trp Gly Lys Gly Met Thr Leu
                325                 330                 335 ctt ccc aaa ccc gtg cgt atc gtt att gct gtt ggc tca cca ata ggt        1056
Leu Pro Lys Pro Val Arg Ile Val Ile Ala Val Gly Ser Pro Ile Gly
            340                 345                 350 ctg gcg gct ctg tat ggc gtg ccg gaa gga cag tcg gtg cct gat cca        1104
Leu Ala Ala Leu Tyr Gly Val Pro Glu Gly Gln Ser Val Pro Asp Pro
        355                 360                 365 gac ccg gcg aag gtg gat ttg att tat gag gag tgg aag aag cat ttg        1152
Asp Pro Ala Lys Val Asp Leu Ile Tyr Glu Glu Trp Lys Lys His Leu
    370                 375                 380 gca ggc ctt tat tat cgg cag cga cct gag tgg gag acg cga gag ttg        1200
Ala Gly Leu Tyr Tyr Arg Gln Arg Pro Glu Trp Glu Thr Arg Glu Leu
385                 390                 395                 400 gag att tgg gac tgt ccg aag tcg tga                                    1227
Glu Ile Trp Asp Cys Pro Lys Ser
                405

<210> SEQ ID NO 38
<211> LENGTH: 1431
<212> TYPE: DNA
<213> ORGANISM: Nannochloropsis sp.
<220> FEATURE:
<221> NAME/KEY: CDS
<222> LOCATION: (1)..(1428)

<400> SEQUENCE: 38 atg tcc tcc ttc ttg cgt tgg cct cgt cgc tcc agg act cct aaa cgt          48
```

```
                Met Ser Ser Phe Leu Arg Trp Pro Arg Arg Ser Arg Thr Pro Lys Arg
                 1               5                  10                 15 act gcc gct gca cct ccc acc gca gca ggc acc acg gcc acc atc ctg            96
Thr Ala Ala Ala Pro Pro Thr Ala Ala Gly Thr Thr Ala Thr Ile Leu
             20                  25                  30 tgc gat ggc ctg cgc ctt gac agc agc agc agt agc atc aac gcc agc           144
Cys Asp Gly Leu Arg Leu Asp Ser Ser Ser Ser Ser Ile Asn Ala Ser
         35                  40                  45 agt agc agt gac agc aac gtc gac agc aag acc gaa tcg atg ggg agc           192
Ser Ser Ser Asp Ser Asn Val Asp Ser Lys Thr Glu Ser Met Gly Ser
     50                  55                  60 agc acc gac gag agc ccc ccg act tcc ccc cag acc acc tcc aaa gct           240
Ser Thr Asp Glu Ser Pro Pro Thr Ser Pro Gln Thr Thr Ser Lys Ala
 65                  70                  75                  80 ctc acg ctc acc ctt ggc gac gtc tgc ccc ggc act cgc cta acc ttg           288
Leu Thr Leu Thr Leu Gly Asp Val Cys Pro Gly Thr Arg Leu Thr Leu
                 85                  90                  95 cct tgg tgg gaa gaa gca ctc ctc ccc tgc ttc gtt gtg ctg tgt               336
Pro Trp Trp Glu Glu Ala Leu Leu Pro Cys Phe Val Val Leu Cys
             100                 105                 110 gcc ccc atc ttt tca ttt atg atg ctt ggc cta tcg ttt gtg cca ttt           384
Ala Pro Ile Phe Ser Phe Met Met Leu Gly Leu Ser Phe Val Pro Phe
         115                 120                 125 ttc ggg tgg gtg tgg gcc agc act agc tac ctc tcc gca ttc tcc ttc           432
Phe Gly Trp Val Trp Ala Ser Thr Ser Tyr Leu Ser Ala Phe Ser Phe
     130                 135                 140 tac tgg gtc ctg ctg tac ttc gac ctc gtc cct cgc cgg gaa cgc ctt           480
Tyr Trp Val Leu Leu Tyr Phe Asp Leu Val Pro Arg Arg Glu Arg Leu
145                 150                 155                 160 agt cct ccc tgc ctc tct acc tgg ttc ctg cgg gcc atg gtg cgg tac           528
Ser Pro Pro Cys Leu Ser Thr Trp Phe Leu Arg Ala Met Val Arg Tyr
                 165                 170                 175 ttc aac tat ttt gtc ata gtc gaa gat cct tcc tcc atc cag ccc tcc           576
Phe Asn Tyr Phe Val Ile Val Glu Asp Pro Ser Ser Ile Gln Pro Ser
             180                 185                 190 act ccc tac atc ggt gtg cag agc ccg cac ggc att tat ccc att gca           624
Thr Pro Tyr Ile Gly Val Gln Ser Pro His Gly Ile Tyr Pro Ile Ala
         195                 200                 205 agc gtc tgt gcc gct ccc ttc agc ccc agt ctc ttc cga ggc cgc gat           672
Ser Val Cys Ala Ala Pro Phe Ser Pro Ser Leu Phe Arg Gly Arg Asp
     210                 215                 220 tca tat tgt atg gcg gcg tcg gcg ttg cag ttg cag cct ttt ttg tgg           720
Ser Tyr Cys Met Ala Ala Ser Ala Leu Gln Leu Gln Pro Phe Leu Trp
225                 230                 235                 240 caa tgg ctg gag aca ctg ggg ggg cga ccg ata tcg gcg gca ggg atc           768
Gln Trp Leu Glu Thr Leu Gly Gly Arg Pro Ile Ser Ala Ala Gly Ile
                 245                 250                 255 acg aag gtg gtg gag cag gga gac gta tgt tgt att cta ccg gga gga           816
Thr Lys Val Val Glu Gln Gly Asp Val Cys Cys Ile Leu Pro Gly Gly
             260                 265                 270 atc gca gaa atg ttc atg ctg gat cca tca aac gag acg gag aag gtc           864
Ile Ala Glu Met Phe Met Leu Asp Pro Ser Asn Glu Thr Glu Lys Val
         275                 280                 285 ctg att cga cgg ggt ttc ata cgc gaa gcg ttg aag aac cgt gtg gat           912
Leu Ile Arg Arg Gly Phe Ile Arg Glu Ala Leu Lys Asn Arg Val Asp
     290                 295                 300 atc atc ccg atg tat cac ttt aac cac acg cag acg ttc agc tac atc           960
Ile Ile Pro Met Tyr His Phe Asn His Thr Gln Thr Phe Ser Tyr Ile
305                 310                 315                 320
```

| | | |
|---|---|---|
| ctt cct cct tcg ctc aat gaa ttg ttg gca acc gtg tgt cgg aag agt<br>Leu Pro Pro Ser Leu Asn Glu Leu Leu Ala Thr Val Cys Arg Lys Ser<br>325 330 335 | | 1008 |
| ggg ttg cct ggc tgc ttt ttg atc gga cga tgg gga tta ttt gtc cct<br>Gly Leu Pro Gly Cys Phe Leu Ile Gly Arg Trp Gly Leu Phe Val Pro<br>340 345 350 | | 1056 |
| cat aag gtc aag atg ttc tcg gtt gtg ggg agg ccg att cag gtg cgg<br>His Lys Val Lys Met Phe Ser Val Val Gly Arg Pro Ile Gln Val Arg<br>355 360 365 | | 1104 |
| cga cgc cac tgc agc agc agc agc agc agc agc agc agc agc agc<br>Arg Arg His Cys Ser Ser Ser Ser Ser Ser Ser Ser Ser Ser Ser<br>370 375 380 | | 1152 |
| agc tgc aaa aac aac agt ggg aat ggg aag att ccg ggg acg gag gat<br>Ser Cys Lys Asn Asn Ser Gly Asn Gly Lys Ile Pro Gly Thr Glu Asp<br>385 390 395 400 | | 1200 |
| gga agg gcg aag aag gta ggc atg gag gga gag aag tat gag cca acg<br>Gly Arg Ala Lys Lys Val Gly Met Glu Gly Glu Lys Tyr Glu Pro Thr<br>405 410 415 | | 1248 |
| gag gag gag att gag gca gtg gtt gtg gag tac aag gag gca cta cgc<br>Glu Glu Glu Ile Glu Ala Val Val Val Glu Tyr Lys Glu Ala Leu Arg<br>420 425 430 | | 1296 |
| cgc att tat tac act ttt cga ccg gcg gat gaa cag cgg gag ctg gtg<br>Arg Ile Tyr Tyr Thr Phe Arg Pro Ala Asp Glu Gln Arg Glu Leu Val<br>435 440 445 | | 1344 |
| ctg gtg gat aac cag aag ggg aac agc gct agc agc agc agc agc agc<br>Leu Val Asp Asn Gln Lys Gly Asn Ser Ala Ser Ser Ser Ser Ser Ser<br>450 455 460 | | 1392 |
| agc agc agc agt agc agc ggt aag aat aat agc cat tag<br>Ser Ser Ser Ser Ser Ser Gly Lys Asn Asn Ser His<br>465 470 475 | | 1431 |

<210> SEQ ID NO 39
<211> LENGTH: 1446
<212> TYPE: DNA
<213> ORGANISM: Nannochloropsis sp.
<220> FEATURE:
<221> NAME/KEY: CDS
<222> LOCATION: (1)..(1443)

<400> SEQUENCE: 39

| | | |
|---|---|---|
| atg ttg ata gtc gtc gtt tgc ctt cta tcg cgt ccg tgt cac gcg ttt<br>Met Leu Ile Val Val Val Cys Leu Leu Ser Arg Pro Cys His Ala Phe<br>1 5 10 15 | | 48 |
| acg ccc ggc gtc agc aga tgt ccc cac acc agc aag acg ctc aat gtg<br>Thr Pro Gly Val Ser Arg Cys Pro His Thr Ser Lys Thr Leu Asn Val<br>20 25 30 | | 96 |
| cct gga agc acc cgc ctg act ccc ttg ctt act gct ctg gac gac gac<br>Pro Gly Ser Thr Arg Leu Thr Pro Leu Leu Thr Ala Leu Asp Asp Asp<br>35 40 45 | | 144 |
| gaa atc gct gtt gtg acc cag gcg gac gct gcc gtg aat gcc atg ttt<br>Glu Ile Ala Val Val Thr Gln Ala Asp Ala Ala Val Asn Ala Met Phe<br>50 55 60 | | 192 |
| aag aag cca ctg cgt gtg ggg ctg ttg gtg gag ccg acg ccc ttc acg<br>Lys Lys Pro Leu Arg Val Gly Leu Leu Val Glu Pro Thr Pro Phe Thr<br>65 70 75 80 | | 240 |
| cac gta agc ggc tac gcg aat cgg ttc aag gag atg ctc aag cac ctg<br>His Val Ser Gly Tyr Ala Asn Arg Phe Lys Glu Met Leu Lys His Leu<br>85 90 95 | | 288 |
| cac cgc acg ggg gac caa gtg gag atc tgt aca acg gat gac gtc cct<br>His Arg Thr Gly Asp Gln Val Glu Ile Cys Thr Thr Asp Asp Val Pro<br>100 105 110 | | 336 |

```
gaa gcc ccc aag aag ttt ctt gat tac caa att cag tac acc cct ggc         384
Glu Ala Pro Lys Lys Phe Leu Asp Tyr Gln Ile Gln Tyr Thr Pro Gly
        115                 120                 125 ttc cgt ttt ccg ctc tac gat cac att tgc cta aca ttt gac tat aaa         432
Phe Arg Phe Pro Leu Tyr Asp His Ile Cys Leu Thr Phe Asp Tyr Lys
130                 135                 140 atg atc gcg tac aat ttc ctc aag ctc ttt cgc cca cat atc atc cac         480
Met Ile Ala Tyr Asn Phe Leu Lys Leu Phe Arg Pro His Ile Ile His
145                 150                 155                 160 gtc tcc acc cct ggg tgt ctc tgt ttt gct gca gca atc tac gca agg         528
Val Ser Thr Pro Gly Cys Leu Cys Phe Ala Ala Ala Ile Tyr Ala Arg
                165                 170                 175 gtc ctg cgg att ccc ttg ctc ttt tcg tat cac acc cac ctg ccc att         576
Val Leu Arg Ile Pro Leu Leu Phe Ser Tyr His Thr His Leu Pro Ile
            180                 185                 190 tac gcc cga gac tac atg ggc ttt gtc cct ggt atc gtc ggc ctg aca         624
Tyr Ala Arg Asp Tyr Met Gly Phe Val Pro Gly Ile Val Gly Leu Thr
        195                 200                 205 aga ttc gtc att cgt gtg gtg cac aac tgg gcg gac tta acg ctg gtg         672
Arg Phe Val Ile Arg Val Val His Asn Trp Ala Asp Leu Thr Leu Val
210                 215                 220 acc agc cca cag ctc aag gac gaa ttg cag ggt ttt ggc gtg aag cgt         720
Thr Ser Pro Gln Leu Lys Asp Glu Leu Gln Gly Phe Gly Val Lys Arg
225                 230                 235                 240 gtg gca gtt tgg aag aaa ggg gtc gac acg gac cgt ttc cat ccg aag         768
Val Ala Val Trp Lys Lys Gly Val Asp Thr Asp Arg Phe His Pro Lys
                245                 250                 255 ttt cgg agt gcg gcc atg cgg gat cgc ttg acg gat gga cat cca gag         816
Phe Arg Ser Ala Ala Met Arg Asp Arg Leu Thr Asp Gly His Pro Glu
            260                 265                 270 gcg cca ctg tta gtg tat gtg gga cgg ttg ggt gcc gag aag aag ttg         864
Ala Pro Leu Leu Val Tyr Val Gly Arg Leu Gly Ala Glu Lys Lys Leu
        275                 280                 285 aag atg ctc aaa gga gtg atg gag agg att cct gcg gcg agg ctt gcg         912
Lys Met Leu Lys Gly Val Met Glu Arg Ile Pro Ala Ala Arg Leu Ala
290                 295                 300 ctg gtg ggt gga gga cca gcc gag gct gat ctg cga gag cat ttc aag         960
Leu Val Gly Gly Gly Pro Ala Glu Ala Asp Leu Arg Glu His Phe Lys
305                 310                 315                 320 ggg aca aat act gtg ttt acg ggt gtg tta cac gga gag gag tta agc        1008
Gly Thr Asn Thr Val Phe Thr Gly Val Leu His Gly Glu Glu Leu Ser
                325                 330                 335 cag gcg ttt gcc tcg gcg gac gta ttt ttg atg cct tcg gat tcg gag        1056
Gln Ala Phe Ala Ser Ala Asp Val Phe Leu Met Pro Ser Asp Ser Glu
            340                 345                 350 acg ctg ggc ttc gtt gtg ttg gag tcg atg gcg agt ggg gtg cct gtg        1104
Thr Leu Gly Phe Val Val Leu Glu Ser Met Ala Ser Gly Val Pro Val
        355                 360                 365 ata ggg gca aga gcg ggg ggg atc cct aat gtg att gca cat ggg aag        1152
Ile Gly Ala Arg Ala Gly Gly Ile Pro Asn Val Ile Ala His Gly Lys
370                 375                 380 acg gga ttt ttg gcc cca gtg ggc gac gag gag gcg ttt gcg gta cgg        1200
Thr Gly Phe Leu Ala Pro Val Gly Asp Glu Glu Ala Phe Ala Val Arg
385                 390                 395                 400 gca ctg cag ttg ttg ggg gat aaa tca ttg atg gtg aag atg aag gag        1248
Ala Leu Gln Leu Leu Gly Asp Lys Ser Leu Met Val Lys Met Lys Glu
                405                 410                 415 gcg ggg agg gcg gag gcg gag aga ttg gat tgg gcg tgc gcg atg gaa        1296
Ala Gly Arg Ala Glu Ala Glu Arg Leu Asp Trp Ala Cys Ala Met Glu
            420                 425                 430
```

```
cat ttg aga aat ata cat tac aag cgt gcg gtg atg att cac agg cga      1344
His Leu Arg Asn Ile His Tyr Lys Arg Ala Val Met Ile His Arg Arg
        435                 440                 445 agg aca ttg agt gcg ttt ttg gca tgg gcg ggg acg ttg aag cag cga      1392
Arg Thr Leu Ser Ala Phe Leu Ala Trp Ala Gly Thr Leu Lys Gln Arg
450                 455                 460 aca gtg aag agc gtg aag cag agt atg gag ggt atg ttc gcg aca gct      1440
Thr Val Lys Ser Val Lys Gln Ser Met Glu Gly Met Phe Ala Thr Ala
465                 470                 475                 480 acg taa                                                              1446
Thr

<210> SEQ ID NO 40
<211> LENGTH: 1686
<212> TYPE: DNA
<213> ORGANISM: Nannochloropsis sp.
<220> FEATURE:
<221> NAME/KEY: CDS
<222> LOCATION: (1)..(1683)

<400> SEQUENCE: 40 atg gcc tcc ttc gat tcc ggt gag atc aag cgt ttg gtg ctt gtg acc        48
Met Ala Ser Phe Asp Ser Gly Glu Ile Lys Arg Leu Val Leu Val Thr
1               5                   10                  15 gat gcg tgg cag ccc cag gtg aac ggc gtg gtt cga aca ctt aat acg        96
Asp Ala Trp Gln Pro Gln Val Asn Gly Val Val Arg Thr Leu Asn Thr
                20                  25                  30 acc aca cac gtc ctc cgc gcc tta ggc gtc gag gtg cac gtt atc agt       144
Thr Thr His Val Leu Arg Ala Leu Gly Val Glu Val His Val Ile Ser
            35                  40                  45 cct caa gaa ttc aac aca gta cct tgt cca acc tat ccc agc atc caa       192
Pro Gln Glu Phe Asn Thr Val Pro Cys Pro Thr Tyr Pro Ser Ile Gln
        50                  55                  60 ttg gcg gtg cta ccg ggc gag aaa gtg cgg agg cgt atc act gaa ctg       240
Leu Ala Val Leu Pro Gly Glu Lys Val Arg Arg Arg Ile Thr Glu Leu
65                  70                  75                  80 gct cct cac gca ctg cac gtg gcg acg gaa ggg cct ctg ggg tgg gca       288
Ala Pro His Ala Leu His Val Ala Thr Glu Gly Pro Leu Gly Trp Ala
                85                  90                  95 gcg cgc aac ttt gcg gtg gag ctt ggc atc ccc ttc acg acg gct gtg       336
Ala Arg Asn Phe Ala Val Glu Leu Gly Ile Pro Phe Thr Thr Ala Val
            100                 105                 110 cat act cgc ttc cca gag tat gtg tac gcg cgc ttg gcc ttg ccc ttg       384
His Thr Arg Phe Pro Glu Tyr Val Tyr Ala Arg Leu Ala Leu Pro Leu
        115                 120                 125 cgt atc acc tat cgt tat ctc cga tgg ttc cat ttt cat tcc aaa gcg       432
Arg Ile Thr Tyr Arg Tyr Leu Arg Trp Phe His Phe His Ser Lys Ala
130                 135                 140 ata atg gtc cct aca cct atg gtc aag cgt gat ttg gag ggt cat ggt       480
Ile Met Val Pro Thr Pro Met Val Lys Arg Asp Leu Glu Gly His Gly
145                 150                 155                 160 ttt gag aat gtc caa ctg tgg agc cgc ggt gtc gat aca gac gtc ttt       528
Phe Glu Asn Val Gln Leu Trp Ser Arg Gly Val Asp Thr Asp Val Phe
                165                 170                 175 cac acc ccc gct gca ggc att cgt ttg cct gcg agt gat tcg acc tac       576
His Thr Pro Ala Ala Gly Ile Arg Leu Pro Ala Ser Asp Ser Thr Tyr
            180                 185                 190 ccc atc ttt ttg tac gca ggc cgc gta gca gta gaa aag aac gtt gaa       624
Pro Ile Phe Leu Tyr Ala Gly Arg Val Ala Val Glu Lys Asn Val Glu
        195                 200                 205
```

-continued

| | |
|---|---|
| gcc ttc ttg gca ttg gac ttg ccc ggg cag aag tgg gtt gtg ggg gac<br>Ala Phe Leu Ala Leu Asp Leu Pro Gly Gln Lys Trp Val Val Gly Asp<br>210               215                    220 | 672 |
| ggg ccc gcc ttg gag ggg cta caa gcc gct tat ccc gaa gcc cgc tat<br>Gly Pro Ala Leu Glu Gly Leu Gln Ala Ala Tyr Pro Glu Ala Arg Tyr<br>225                 230              235                 240 | 720 |
| ttt gga ttt ttg aac cag acg gag ttg gcc aag att tat cag cag tcg<br>Phe Gly Phe Leu Asn Gln Thr Glu Leu Ala Lys Ile Tyr Gln Gln Ser<br>                 245                   250                    255 | 768 |
| agc gtt ttt gta ttt ccc agc aag acg gat acc ttt ggg ctt gtt cta<br>Ser Val Phe Val Phe Pro Ser Lys Thr Asp Thr Phe Gly Leu Val Leu<br>           260                    265                    270 | 816 |
| ctt gag gcc atg gca aca ggg ctg ccc gta gcc gca tat ccc gtc tca<br>Leu Glu Ala Met Ala Thr Gly Leu Pro Val Ala Ala Tyr Pro Val Ser<br>                 275                   280                 285 | 864 |
| ggg ccg att gat gtc gtc agc act tcc ggt gcg ggt gta tta gac aat<br>Gly Pro Ile Asp Val Val Ser Thr Ser Gly Ala Gly Val Leu Asp Asn<br>290               295                    300 | 912 |
| gac ctg cgc tcg gcg tgt ctg cgg gca ttg aac att gat ccg gcc gtg<br>Asp Leu Arg Ser Ala Cys Leu Arg Ala Leu Asn Ile Asp Pro Ala Val<br>305               310                    315                 320 | 960 |
| gct cga gcg cat gcg gag aaa tac tcg tgg acg gcg gcg acg caa atg<br>Ala Arg Ala His Ala Glu Lys Tyr Ser Trp Thr Ala Ala Thr Gln Met<br>                 325                   330                 335 | 1008 |
| ttt gcc tcg aat ttg cag tat atc tca ccg ttt atc ttt gcg gaa ggg<br>Phe Ala Ser Asn Leu Gln Tyr Ile Ser Pro Phe Ile Phe Ala Glu Gly<br>           340                    345                    350 | 1056 |
| gtg cgg gag tgg agc aac gcc aga ttc cta gac gat ggg agc aat gat<br>Val Arg Glu Trp Ser Asn Ala Arg Phe Leu Asp Asp Gly Ser Asn Asp<br>                 355                   360                 365 | 1104 |
| ttg gtc tcg tcg ttg ccc gcg cat ttg gta aac tgg ttg gac aag acg<br>Leu Val Ser Ser Leu Pro Ala His Leu Val Asn Trp Leu Asp Lys Thr<br>370               375                    380 | 1152 |
| gga gcg gtg gag gag aag gag ggg ata gta ggc ggc cga ttg att cgg<br>Gly Ala Val Glu Glu Lys Glu Gly Ile Val Gly Gly Arg Leu Ile Arg<br>385               390              395                 400 | 1200 |
| agg gct gtc gag gcg gca gaa gcc gca aag tcg gag acc ccc atc tct<br>Arg Ala Val Glu Ala Ala Glu Ala Ala Lys Ser Glu Thr Pro Ile Ser<br>                     405                   410                 415 | 1248 |
| cta aca ttc cca cca gct gaa acc gcg acg tca act ttc tcc tcc agc<br>Leu Thr Phe Pro Pro Ala Glu Thr Ala Thr Ser Thr Phe Ser Ser Ser<br>           420                    425                    430 | 1296 |
| aac agc agc aac aat agc agc agc agc acg cca tgc ttg cag gcg<br>Asn Ser Ser Asn Asn Ser Ser Ser Ser Thr Pro Cys Leu Gln Ala<br>                 435                   440                 445 | 1344 |
| gcc acg agt gag gac cct ttc ctg aac ccg ggg gga aat gga ggg cca<br>Ala Thr Ser Glu Asp Pro Phe Leu Asn Pro Gly Gly Asn Gly Gly Pro<br>450               455                    460 | 1392 |
| agc tcg gat ttg acg ttt ggg gtg cac cat tac gat agc acc tcc tgg<br>Ser Ser Asp Leu Thr Phe Gly Val His His Tyr Asp Ser Thr Ser Trp<br>465               470              475                 480 | 1440 |
| acg tac ttg atg gtg gtg tgt atg ggt gca aca atg att gga aat tat<br>Thr Tyr Leu Met Val Val Cys Met Gly Ala Thr Met Ile Gly Asn Tyr<br>                   485                   490                 495 | 1488 |
| gtg gcc tca ttt ttc ttc aag gct cgc gga ggg aag agc atg ggt ttt<br>Val Ala Ser Phe Phe Phe Lys Ala Arg Gly Gly Lys Ser Met Gly Phe<br>           500                    505                    510 | 1536 |
| ggg gcg acg acg agg agg gcg cca ata ttc agg agg cca ctg ttg ctg<br>Gly Ala Thr Thr Arg Arg Ala Pro Ile Phe Arg Arg Pro Leu Leu Leu<br>               515                   520                 525 | 1584 |

```
tcc ggc gat gat ggt cgc agt gtc ggg agt atc act ccg ccc ctg tcc        1632
Ser Gly Asp Asp Gly Arg Ser Val Gly Ser Ile Thr Pro Pro Leu Ser
    530                 535                 540 cct gct tca acg tgc agt cat acg aac tcg ttc cac gag gac gcc ctc        1680
Pro Ala Ser Thr Cys Ser His Thr Asn Ser Phe His Glu Asp Ala Leu
545                 550                 555                 560 tgg taa                                                                1686
Trp

<210> SEQ ID NO 41
<211> LENGTH: 1842
<212> TYPE: DNA
<213> ORGANISM: Nannochloropsis sp.
<220> FEATURE:
<221> NAME/KEY: CDS
<222> LOCATION: (1)..(1839)

<400> SEQUENCE: 41 atg cca tgc ggc gac cat gcc cca cga ctg ccg aat gag gac cta gag         48
Met Pro Cys Gly Asp His Ala Pro Arg Leu Pro Asn Glu Asp Leu Glu
1               5                  10                  15 gag gca gcc ggt cac tac tcg gag gaa tct tac gac gcc cgt cgg gac         96
Glu Ala Ala Gly His Tyr Ser Glu Glu Ser Tyr Asp Ala Arg Arg Asp
                20                  25                  30 aag cac cat cac tac ctt acc caa tac cag cta caa caa caa ctg ccc        144
Lys His His His Tyr Leu Thr Gln Tyr Gln Leu Gln Gln Gln Leu Pro
            35                  40                  45 caa caa ggg tcc act agc agc cgt acc agc agt gtt agc agc tgc tcc        192
Gln Gln Gly Ser Thr Ser Ser Arg Thr Ser Ser Val Ser Ser Cys Ser
        50                  55                  60 aca gcg ctt ctc gcc gac acg gac cac atc tgt ctt gaa gca gaa gca        240
Thr Ala Leu Leu Ala Asp Thr Asp His Ile Cys Leu Glu Ala Glu Ala
65                  70                  75                  80 agc gag gag gaa gga tcc agc ggt ggg gac agg ttt gag agc gga gcg        288
Ser Glu Glu Glu Gly Ser Ser Gly Gly Asp Arg Phe Glu Ser Gly Ala
                85                  90                  95 gca ccg cgg gtg gtg att ttt acc gct gct tat tac gtg tgt gat ggc        336
Ala Pro Arg Val Val Ile Phe Thr Ala Ala Tyr Tyr Val Cys Asp Gly
                100                 105                 110 gtg agt ctc aca ata cgg aaa ctc cgg ggg cac ctt caa tcg aaa ggg        384
Val Ser Leu Thr Ile Arg Lys Leu Arg Gly His Leu Gln Ser Lys Gly
            115                 120                 125 atc gca tcc cgc gtc gta tcg tgt ggg cct gcg ggc tgg agc gaa cca        432
Ile Ala Ser Arg Val Val Ser Cys Gly Pro Ala Gly Trp Ser Glu Pro
        130                 135                 140 gat gta ttt acg gtc cct tca att ccg ttg ccg att att aat gca gat        480
Asp Val Phe Thr Val Pro Ser Ile Pro Leu Pro Ile Ile Asn Ala Asp
145                 150                 155                 160 gat aac ttt ggg tat tct cta ggg ctc aaa ctg acg gaa cgt tgc aag        528
Asp Asn Phe Gly Tyr Ser Leu Gly Leu Lys Leu Thr Glu Arg Cys Lys
                165                 170                 175 gcg cag atc aag agt ttt aag cct tcg gtc att cac ttc act gtg ccg        576
Ala Gln Ile Lys Ser Phe Lys Pro Ser Val Ile His Phe Thr Val Pro
            180                 185                 190 gat ttt ttg gct ttg gat gcc ctg agg tgg gcg aag gcg gag cat atc        624
Asp Phe Leu Ala Leu Asp Ala Leu Arg Trp Ala Lys Ala Glu His Ile
        195                 200                 205 cca gtg atg ggc aca tgg cac agc aat tat tcc gat tat ctg aag ttt        672
Pro Val Met Gly Thr Trp His Ser Asn Tyr Ser Asp Tyr Leu Lys Phe
210                 215                 220
```

| | | |
|---|---|---|
| tat cat ttg aat ata att cga ttg ccc gtg gag agg tac att agg tcg<br>Tyr His Leu Asn Ile Ile Arg Leu Pro Val Glu Arg Tyr Ile Arg Ser<br>225                  230                  235                  240 | | 720 |
| ttt tac gtt aac atg ccc atc tac gtt ccc acg ccg ttt att cgc aag<br>Phe Tyr Val Asn Met Pro Ile Tyr Val Pro Thr Pro Phe Ile Arg Lys<br>                  245                  250                  255 | | 768 |
| cgg ttg ttg gat agt ggg ttt ccg aca gaa cga gtg gga ata tgg ggg<br>Arg Leu Leu Asp Ser Gly Phe Pro Thr Glu Arg Val Gly Ile Trp Gly<br>                260                  265                  270 | | 816 |
| agg ggg gtc gat ttc aat atg ttc aag ccg tcg aat cga tcg atg gca<br>Arg Gly Val Asp Phe Asn Met Phe Lys Pro Ser Asn Arg Ser Met Ala<br>            275                  280                  285 | | 864 |
| ttc agg cgg gag agg ggg gtt gag gat gat gag gtc gtc ata ttg tgg<br>Phe Arg Arg Glu Arg Gly Val Glu Asp Asp Glu Val Val Ile Leu Trp<br>290                  295                  300 | | 912 |
| gtg ggg cgt ctg gtt aag gaa aag agt cct gat ata tgg gcg gag gta<br>Val Gly Arg Leu Val Lys Glu Lys Ser Pro Asp Ile Trp Ala Glu Val<br>305                  310                  315                  320 | | 960 |
| ata cgg aga ttg gaa aga gag ggg tta aga ttt cga gct ctg gtg gtg<br>Ile Arg Arg Leu Glu Arg Glu Gly Leu Arg Phe Arg Ala Leu Val Val<br>                        325                  330                  335 | | 1008 |
| ggg agc ggg agt tgg gag gag aat atg aaa aaa ttg cca agg aca gag<br>Gly Ser Gly Ser Trp Glu Glu Asn Met Lys Lys Leu Pro Arg Thr Glu<br>            340                  345                  350 | | 1056 |
| cat ttg ggg tgg ttg agt ggg gag gcg ttg gcg cgg gtg tat gcg agt<br>His Leu Gly Trp Leu Ser Gly Glu Ala Leu Ala Arg Val Tyr Ala Ser<br>355                  360                  365 | | 1104 |
| gtg gac gtg ttt tta ttc ccg agc gag gtg gag acg ttt ggt aat gtc<br>Val Asp Val Phe Leu Phe Pro Ser Glu Val Glu Thr Phe Gly Asn Val<br>370                  375                  380 | | 1152 |
| acg ttg gag gcc ttg gca agc ggc gtg ccg tgt gtg gcg tca gcg gga<br>Thr Leu Glu Ala Leu Ala Ser Gly Val Pro Cys Val Ala Ser Ala Gly<br>385                  390                  395                  400 | | 1200 |
| tgc agt gga cat ctg gta agt cat ggg atc aat ggt ttt gtg gtg gga<br>Cys Ser Gly His Leu Val Ser His Gly Ile Asn Gly Phe Val Val Gly<br>                        405                  410                  415 | | 1248 |
| aag gcg gat gtg gag gag tat tat atg ttg acg agg cgt ttg gtg gtg<br>Lys Ala Asp Val Glu Glu Tyr Tyr Met Leu Thr Arg Arg Leu Val Val<br>            420                  425                  430 | | 1296 |
| gac aag gga ttg agg gag cga ttt gcg gcg aaa gca agg ggc agc atc<br>Asp Lys Gly Leu Arg Glu Arg Phe Ala Ala Lys Ala Arg Gly Ser Ile<br>435                  440                  445 | | 1344 |
| aag gaa ctg gag cat gat aga gtg atg gat atg atg gtc acg aat tat<br>Lys Glu Leu Glu His Asp Arg Val Met Asp Met Met Val Thr Asn Tyr<br>450                  455                  460 | | 1392 |
| gag ggg gta atg cat gct tat cat cag gtt ggg ggg gac ggc tgc gcg<br>Glu Gly Val Met His Ala Tyr His Gln Val Gly Gly Asp Gly Cys Ala<br>465                  470                  475                  480 | | 1440 |
| agt cgg agt aat ggc tgg ggg gat gtc tgg ata gcg atg ata ttt cac<br>Ser Arg Ser Asn Gly Trp Gly Asp Val Trp Ile Ala Met Ile Phe His<br>                        485                  490                  495 | | 1488 |
| ttt ttt tcg ttt tta ctt tgg ttg ggg aca ccg ttg atg aag gga tat<br>Phe Phe Ser Phe Leu Leu Trp Leu Gly Thr Pro Leu Met Lys Gly Tyr<br>            500                  505                  510 | | 1536 |
| gtg gct gtc gcg agt ggg gtg ggg gca tgc tgg agg cgg ccg ttt tgg<br>Val Ala Val Ala Ser Gly Val Gly Ala Cys Trp Arg Arg Pro Phe Trp<br>515                  520                  525 | | 1584 |
| ggg gga ttg ccg gat cgg atg ctg atg ggc ttt gca cgg tgt ttt tct<br>Gly Gly Leu Pro Asp Arg Met Leu Met Gly Phe Ala Arg Cys Phe Ser<br>530                  535                  540 | | 1632 |

```
tgt ttg ata cga cgg cag cag ctg cag ctg cct cga gta ggg ggg gga      1680
Cys Leu Ile Arg Arg Gln Gln Leu Gln Leu Pro Arg Val Gly Gly Gly
545                 550                 555                 560 agg gga ggt gga gaa agg gaa gga ggg agg ccg gta ttt cga gag cgg      1728
Arg Gly Gly Gly Glu Arg Glu Gly Gly Arg Pro Val Phe Arg Glu Arg
                565                 570                 575 gtg aag atg ttg gcg atc tgt gtg tgg ttg tct gca att gtg ata gta      1776
Val Lys Met Leu Ala Ile Cys Val Trp Leu Ser Ala Ile Val Ile Val
            580                 585                 590 tat cac acg tat acg agc atg gac tgg aaa gca acg gtt gga ggt tgg      1824
Tyr His Thr Tyr Thr Ser Met Asp Trp Lys Ala Thr Val Gly Gly Trp
        595                 600                 605 gga ggg gag gag agg tag                                              1842
Gly Gly Glu Glu Arg
610

<210> SEQ ID NO 42
<211> LENGTH: 2481
<212> TYPE: DNA
<213> ORGANISM: Nannochloropsis sp.
<220> FEATURE:
<221> NAME/KEY: CDS
<222> LOCATION: (1)..(2478)

<400> SEQUENCE: 42 atg tgg ggc tta tta tgg aaa cac atg acc cta cga ctc ctc ttc gtc        48
Met Trp Gly Leu Leu Trp Lys His Met Thr Leu Arg Leu Leu Phe Val
1               5                   10                  15 tca gtc tgc ttg gtc acc tcc tcc atc ggc gcc aac atg atg gcc ctc        96
Ser Val Cys Leu Val Thr Ser Ser Ile Gly Ala Asn Met Met Ala Leu
            20                  25                  30 gcc ctc ttc ctc gtc atc cga ccc ttt tcc cgc tcg ctg tat cga cgg       144
Ala Leu Phe Leu Val Ile Arg Pro Phe Ser Arg Ser Leu Tyr Arg Arg
        35                  40                  45 ttg gtg tca cag tgt gtg gca tgc atg tgg atc gat gca ctg tcc ttg       192
Leu Val Ser Gln Cys Val Ala Cys Met Trp Ile Asp Ala Leu Ser Leu
    50                  55                  60 ctc cta ccg gga acc aac atc cac att gct gct gac tct gac atg ccc       240
Leu Leu Pro Gly Thr Asn Ile His Ile Ala Ala Asp Ser Asp Met Pro
65                  70                  75                  80 gac ggg atc act gcc ggc atc gtg gtg gcc aat cac caa tac gaa ggt       288
Asp Gly Ile Thr Ala Gly Ile Val Val Ala Asn His Gln Tyr Glu Gly
                85                  90                  95 gat tgg tgg ttc atg ctc atg gtc gcc cgc ttc ctg ggc ctg cat ggg       336
Asp Trp Trp Phe Met Leu Met Val Ala Arg Phe Leu Gly Leu His Gly
            100                 105                 110 aac gtg aag ata ata gtc agg gag ggc ctt aag aag atc ccc ctc ttg       384
Asn Val Lys Ile Ile Val Arg Glu Gly Leu Lys Lys Ile Pro Leu Leu
        115                 120                 125 ggg tgg ctg gtc cgg ctt gtc gag tac cca ttc atc tcc tcc tcc tgg       432
Gly Trp Leu Val Arg Leu Val Glu Tyr Pro Phe Ile Ser Ser Ser Trp
    130                 135                 140 tcg ctc tcc cgc acg aac ctc ttt ggg ctg ctg cgg agt ttc aat gcg       480
Ser Leu Ser Arg Thr Asn Leu Phe Gly Leu Leu Arg Ser Phe Asn Ala
145                 150                 155                 160 gac gac ttc ccc gtc ctc ctc ttc cag ttc ccc gag ggc gat cgc atc       528
Asp Asp Phe Pro Val Leu Leu Phe Gln Phe Pro Glu Gly Asp Arg Ile
                165                 170                 175 gat gcc aaa gtc cgt cag caa tcg ctt gcc ttt gcg gcc aag gag caa       576
Asp Ala Lys Val Arg Gln Gln Ser Leu Ala Phe Ala Ala Lys Glu Gln
            180                 185                 190
```

| | | | | | | | | | | | | | | | | |
|---|---|---|---|---|---|---|---|---|---|---|---|---|---|---|---|---|
| cgc | ccg | cac | ctc | ctc | cac | gtc | ctc | ctc | ccc | cgt | act | acc | ggt | ttc | aac | 624 |
| Arg | Pro | His | Leu | Leu | His | Val | Leu | Leu | Pro | Arg | Thr | Thr | Gly | Phe | Asn | |
| | | 195 | | | | 200 | | | | 205 | | | | | | |
| acc | tgc | atc | gaa | gcg | ctt | agg | act | tcc | cat | ccc | ccc | gtc | tat | gat | atg | 672 |
| Thr | Cys | Ile | Glu | Ala | Leu | Arg | Thr | Ser | His | Pro | Pro | Val | Tyr | Asp | Met | |
| | 210 | | | | | 215 | | | | | 220 | | | | | |
| aca | att | gcc | atc | cct | ggc | acc | acg | ggc | cag | cct | tcc | tcc | tcc | tcc | tcc | 720 |
| Thr | Ile | Ala | Ile | Pro | Gly | Thr | Thr | Gly | Gln | Pro | Ser | Ser | Ser | Ser | Ser | |
| 225 | | | | | 230 | | | | | 235 | | | | | 240 | |
| tcc | tcc | tca | cct | tct | gct | gca | gct | gct | gcg | gcg | tct | cca | tct | gct | ggt | 768 |
| Ser | Ser | Ser | Pro | Ser | Ala | Ala | Ala | Ala | Ala | Ala | Ser | Pro | Ser | Ala | Gly | |
| | | | | 245 | | | | | 250 | | | | | 255 | | |
| gcg | gcg | gcg | gcg | gcg | gcg | gcg | gcg | agc | aac | aca | tca | acc | aac | cct | tct | 816 |
| Ala | Ala | Ala | Ala | Ala | Ala | Ala | Ala | Ser | Asn | Thr | Ser | Thr | Asn | Pro | Ser | |
| | | | 260 | | | | | 265 | | | | | 270 | | | |
| tcc | aac | cct | ccc | tcg | agc | agc | agc | acc | gat | act | agt | cca | gct | gct | gct | 864 |
| Ser | Asn | Pro | Pro | Ser | Ser | Ser | Ser | Thr | Asp | Thr | Ser | Pro | Ala | Ala | Ala | |
| | | 275 | | | | | 280 | | | | | 285 | | | | |
| gct | gct | gct | gct | gct | gat | gcc | gct | gct | gcc | gag | agt | cat | gac | gct | tct | 912 |
| Ala | Ala | Ala | Ala | Ala | Asp | Ala | Ala | Ala | Ala | Glu | Ser | His | Asp | Ala | Ser | |
| | 290 | | | | | 295 | | | | | 300 | | | | | |
| ctc | ttt | cac | acc | ttc | ctc | cgt | ttc | tgc | aac | ggc | gag | ggc | cca | cgg | gac | 960 |
| Leu | Phe | His | Thr | Phe | Leu | Arg | Phe | Cys | Asn | Gly | Glu | Gly | Pro | Arg | Asp | |
| 305 | | | | | 310 | | | | | 315 | | | | | 320 | |
| gtg | cat | atc | aga | ctc | aag | cgc | tac | tcc | ctc | aac | gac | gtc | ctg | gcc | gac | 1008 |
| Val | His | Ile | Arg | Leu | Lys | Arg | Tyr | Ser | Leu | Asn | Asp | Val | Leu | Ala | Asp | |
| | | | | 325 | | | | | 330 | | | | | 335 | | |
| ccc | cac | tgg | ctc | gac | acc | aaa | tgg | gcc | gag | aaa | gac | cgc | gtc | ttg | acc | 1056 |
| Pro | His | Trp | Leu | Asp | Thr | Lys | Trp | Ala | Glu | Lys | Asp | Arg | Val | Leu | Thr | |
| | | | 340 | | | | | 345 | | | | | 350 | | | |
| tac | ttt | tcc | cgc | cac | gcc | tgc | ttt | cct | gct | ccg | ctc | cct | ccc | cac | atg | 1104 |
| Tyr | Phe | Ser | Arg | His | Ala | Cys | Phe | Pro | Ala | Pro | Leu | Pro | Pro | His | Met | |
| | | 355 | | | | | 360 | | | | | 365 | | | | |
| gcc | aat | ggt | ggg | ggc | agc | act | cag | aca | cac | ggg | ggg | agg | ggg | ggc | ccc | 1152 |
| Ala | Asn | Gly | Gly | Gly | Ser | Thr | Gln | Thr | His | Gly | Gly | Arg | Gly | Gly | Pro | |
| | 370 | | | | | 375 | | | | | 380 | | | | | |
| aga | ggg | ccg | gcg | ggc | tct | cat | gcc | gtg | gtg | gga | gca | gcg | ggt | aac | gcc | 1200 |
| Arg | Gly | Pro | Ala | Gly | Ser | His | Ala | Val | Val | Gly | Ala | Ala | Gly | Asn | Ala | |
| 385 | | | | | 390 | | | | | 395 | | | | | 400 | |
| cag | tat | ctc | cgg | tcg | ttc | aat | tcc | cgg | aaa | ttc | aaa | gca | gaa | acg | agt | 1248 |
| Gln | Tyr | Leu | Arg | Ser | Phe | Asn | Ser | Arg | Lys | Phe | Lys | Ala | Glu | Thr | Ser | |
| | | | | 405 | | | | | 410 | | | | | 415 | | |
| ttt | ttg | gcg | ttg | gca | cga | ctg | tta | ctc | acg | ccg | ttg | tgc | ctt | ccc | ttg | 1296 |
| Phe | Leu | Ala | Leu | Ala | Arg | Leu | Leu | Leu | Thr | Pro | Leu | Cys | Leu | Pro | Leu | |
| | | | 420 | | | | | 425 | | | | | 430 | | | |
| ttg | ttg | ctg | atg | gcc | tgt | ccg | ctc | atg | act | ctg | tat | gta | tgc | gtg | agc | 1344 |
| Leu | Leu | Leu | Met | Ala | Cys | Pro | Leu | Met | Thr | Leu | Tyr | Val | Cys | Val | Ser | |
| | | 435 | | | | | 440 | | | | | 445 | | | | |
| acc | gtc | cga | agg | tgg | ttg | ggg | gag | gag | att | gtg | ttc | tcg | cca | gga | gga | 1392 |
| Thr | Val | Arg | Arg | Trp | Leu | Gly | Glu | Glu | Ile | Val | Phe | Ser | Pro | Gly | Gly | |
| | 450 | | | | | 455 | | | | | 460 | | | | | |
| cgg | gag | gga | ggg | agg | gag | ggc | ggt | ata | cca | cgg | gtc | agc | tcg | agg | gga | 1440 |
| Arg | Glu | Gly | Gly | Arg | Glu | Gly | Gly | Ile | Pro | Arg | Val | Ser | Ser | Arg | Gly | |
| 465 | | | | | 470 | | | | | 475 | | | | | 480 | |
| ggg | gac | ggg | ggg | agg | aag | gag | ggg | ttg | aat | ggg | gga | gag | gag | agt | gtg | 1488 |
| Gly | Asp | Gly | Gly | Arg | Lys | Glu | Gly | Leu | Asn | Gly | Gly | Glu | Glu | Ser | Val | |
| | | | | 485 | | | | | 490 | | | | | 495 | | |
| acg | ccg | ttg | ccg | att | ccg | acg | ccg | ttt | ttg | ccg | cag | acg | ccg | ttt | acg | 1536 |
| Thr | Pro | Leu | Pro | Ile | Pro | Thr | Pro | Phe | Leu | Pro | Gln | Thr | Pro | Phe | Thr | |

-continued

| | | | | | | | | | | | | | | | |
|---|---|---|---|---|---|---|---|---|---|---|---|---|---|---|---|
| | | | 500 | | | | 505 | | | | | 510 | | | |
| agt | ccg | tta | att | gga | gcg | ttt | gaa | ctg | ggg | gct | ggg | agg | gag | gga | ggg | 1584 |
| Ser | Pro | Leu | Ile | Gly | Ala | Phe | Glu | Leu | Gly | Ala | Gly | Arg | Glu | Gly | Gly | |
| | | | 515 | | | | 520 | | | | | 525 | | | | |
| agg | gag | gga | ggg | gga | ggg | ggt | aat | ggt | gga | gca | gga | gga | ggc | aga | gga | 1632 |
| Arg | Glu | Gly | Gly | Gly | Gly | Gly | Asn | Gly | Gly | Ala | Gly | Gly | Gly | Arg | Gly | |
| | 530 | | | | | 535 | | | | | 540 | | | | | |
| ggt | ggt | ggg | aaa | gga | gga | ggg | gca | ggg | aag | ggg | ggg | gga | ggg | agg | ggg | 1680 |
| Gly | Gly | Gly | Lys | Gly | Gly | Gly | Ala | Gly | Lys | Gly | Gly | Gly | Gly | Arg | Gly | |
| 545 | | | | 550 | | | | | 555 | | | | | 560 | | |
| ggg | gag | agt | ggt | gta | cag | aag | aga | gtg | cac | agt | ttt | gat | atg | cca | agg | 1728 |
| Gly | Glu | Ser | Gly | Val | Gln | Lys | Arg | Val | His | Ser | Phe | Asp | Met | Pro | Arg | |
| | | | | 565 | | | | | 570 | | | | | 575 | | |
| agg | gag | gaa | ggg | agt | gaa | ggg | ggg | gga | ggg | gga | agg | gga | gga | ggg | agt | 1776 |
| Arg | Glu | Glu | Gly | Ser | Glu | Gly | Gly | Gly | Gly | Gly | Arg | Gly | Gly | Gly | Ser | |
| | | | | | 580 | | | | | 585 | | | | | 590 | |
| agt | ttg | agt | gcg | agt | agt | ctg | gca | ggt | ggc | agt | agt | ttg | aat | gcc | ccg | 1824 |
| Ser | Leu | Ser | Ala | Ser | Ser | Leu | Ala | Gly | Gly | Ser | Ser | Leu | Asn | Ala | Pro | |
| | | | | 595 | | | | | 600 | | | | | 605 | | |
| tat | cag | gga | gga | ggg | agg | gag | gga | ggg | agg | gag | gga | gga | ggg | gtt | ggg | 1872 |
| Tyr | Gln | Gly | Gly | Gly | Arg | Glu | Gly | Gly | Arg | Glu | Gly | Gly | Gly | Val | Gly | |
| | 610 | | | | | 615 | | | | | 620 | | | | | |
| aag | ccg | cct | atg | cac | aat | ttg | ggg | tcc | gcg | ggc | gca | gga | ggt | tct | tcc | 1920 |
| Lys | Pro | Pro | Met | His | Asn | Leu | Gly | Ser | Ala | Gly | Ala | Gly | Gly | Ser | Ser | |
| 625 | | | | 630 | | | | | 635 | | | | | 640 | | |
| tcc | ctc | ccg | tcc | tcg | tcc | tcc | ttc | tcg | tcc | tcg | tcg | cag | cat | tcc | cag | 1968 |
| Ser | Leu | Pro | Ser | Ser | Ser | Ser | Phe | Ser | Ser | Ser | Ser | Gln | His | Ser | Gln | |
| | | | | 645 | | | | | 650 | | | | | 655 | | |
| cat | tcg | acg | tca | cag | gag | cag | cag | gag | gag | gaa | atg | atg | ctg | gcg | gcg | 2016 |
| His | Ser | Thr | Ser | Gln | Glu | Gln | Gln | Glu | Glu | Glu | Met | Met | Leu | Ala | Ala | |
| | | | | | 660 | | | | | 665 | | | | | 670 | |
| atg | gcc | atg | cag | cag | ggc | gcg | gag | gga | ggg | atg | gag | gga | gat | gta | gga | 2064 |
| Met | Ala | Met | Gln | Gln | Gly | Ala | Glu | Gly | Gly | Met | Glu | Gly | Asp | Val | Gly | |
| | | | 675 | | | | | 680 | | | | | 685 | | | |
| gcg | ggc | gtt | gga | gag | agg | ctg | agc | agc | ggg | aag | att | tcg | gac | gag | gga | 2112 |
| Ala | Gly | Val | Gly | Glu | Arg | Leu | Ser | Ser | Gly | Lys | Ile | Ser | Asp | Glu | Gly | |
| | 690 | | | | | 695 | | | | | 700 | | | | | |
| agg | agg | ggg | gga | gga | gga | gga | agc | gga | gga | ggg | tgg | ggg | cat | gct | ttt | 2160 |
| Arg | Arg | Gly | Gly | Gly | Gly | Gly | Ser | Gly | Gly | Gly | Trp | Gly | His | Ala | Phe | |
| 705 | | | | 710 | | | | | 715 | | | | | 720 | | |
| gcg | atg | agt | tcc | tcc | tcg | aca | ttg | ggc | gga | aag | gag | gag | gtg | gag | gag | 2208 |
| Ala | Met | Ser | Ser | Ser | Ser | Thr | Leu | Gly | Gly | Lys | Glu | Glu | Val | Glu | Glu | |
| | | | | 725 | | | | | 730 | | | | | 735 | | |
| gaa | ggg | gga | ggg | ggc | ggg | agg | gaa | ggg | gaa | gag | gac | gtg | gca | acg | tcc | 2256 |
| Glu | Gly | Gly | Gly | Gly | Gly | Arg | Glu | Gly | Glu | Glu | Asp | Val | Ala | Thr | Ser | |
| | | | | 740 | | | | | 745 | | | | | 750 | | |
| tcg | acg | acc | tcg | gga | cca | agt | tcc | gag | agt | gac | ttg | tcg | tcg | ccc | gca | 2304 |
| Ser | Thr | Thr | Ser | Gly | Pro | Ser | Ser | Glu | Ser | Asp | Leu | Ser | Ser | Pro | Ala | |
| | | | 755 | | | | | 760 | | | | | 765 | | | |
| gac | gta | tct | ccc | gga | gga | gga | ggg | gaa | gga | gga | ggg | gga | ggg | aag | acg | 2352 |
| Asp | Val | Ser | Pro | Gly | Gly | Gly | Gly | Glu | Gly | Gly | Gly | Gly | Gly | Lys | Thr | |
| | 770 | | | | | 775 | | | | | 780 | | | | | |
| gag | gga | gag | cag | ggg | ctt | gta | atg | gcg | cgt | ggg | ctt | acg | tcc | tcg | ctt | 2400 |
| Glu | Gly | Glu | Gln | Gly | Leu | Val | Met | Ala | Arg | Gly | Leu | Thr | Ser | Ser | Leu | |
| 785 | | | | 790 | | | | | 795 | | | | | 800 | | |
| ccg | ggt | atg | gtg | gtg | ttg | acg | gag | gag | gcg | gtt | tcg | ggg | tta | gag | tgg | 2448 |
| Pro | Gly | Met | Val | Val | Leu | Thr | Glu | Glu | Ala | Val | Ser | Gly | Leu | Glu | Trp | |
| | | | | 805 | | | | | 810 | | | | | 815 | | |
| agg | gga | ggg | agg | gag | gga | ggg | agg | gag | gga | taa | | | | | | 2481 |

```
Arg Gly Gly Arg Glu Gly Gly Arg Glu Gly
        820                 825
```

<210> SEQ ID NO 43
<211> LENGTH: 477
<212> TYPE: DNA
<213> ORGANISM: Nannochloropsis sp.
<220> FEATURE:
<221> NAME/KEY: CDS
<222> LOCATION: (1)..(474)

<400> SEQUENCE: 43

```
atg gcc ggc ccc atc atg acc tct gcg ccc tcc gcg acc acg ccc acg      48
Met Ala Gly Pro Ile Met Thr Ser Ala Pro Ser Ala Thr Thr Pro Thr
  1               5                  10                  15 ggc aag aca atg ccg ttc aag cag cct ttc aag act gtg gcc acg ctg      96
Gly Lys Thr Met Pro Phe Lys Gln Pro Phe Lys Thr Val Ala Thr Leu
             20                  25                  30 tcc gcc aag act ggc aac att acc aag ccc atc gac cct gcc atc tcc     144
Ser Ala Lys Thr Gly Asn Ile Thr Lys Pro Ile Asp Pro Ala Ile Ser
         35                  40                  45 aag acc att gac ttc gtc tac aat ggt tac tcg acg gtc aag acc aag     192
Lys Thr Ile Asp Phe Val Tyr Asn Gly Tyr Ser Thr Val Lys Thr Lys
     50                  55                  60 gtt gac aag gcc cct aag gta aac ccc tac ctg ctc att gcc ggc ggc     240
Val Asp Lys Ala Pro Lys Val Asn Pro Tyr Leu Leu Ile Ala Gly Gly
 65                  70                  75                  80 ctc gtc ctc tcg tgc atc atc tcc atg tgc ctg ctc gtc ccg gcc gtg     288
Leu Val Leu Ser Cys Ile Ile Ser Met Cys Leu Leu Val Pro Ala Val
                 85                  90                  95 atc ttc ttc ccc gtc acc atc ttc ctg ggt gtc gct acg tcg ttt gcg     336
Ile Phe Phe Pro Val Thr Ile Phe Leu Gly Val Ala Thr Ser Phe Ala
            100                 105                 110 ctc att gca ttg gcc ccc gtg gct ttt gtg ttc ggg tgg atc ctg atc     384
Leu Ile Ala Leu Ala Pro Val Ala Phe Val Phe Gly Trp Ile Leu Ile
        115                 120                 125 tcc tct gct ccg atc cag gat aag gtg gtg gtg ccc gcc ttg gac aag     432
Ser Ser Ala Pro Ile Gln Asp Lys Val Val Val Pro Ala Leu Asp Lys
    130                 135                 140 gtg ctg gcc aat aag aag gtg gcg aag ttc ctc ctc aag gag taa         477
Val Leu Ala Asn Lys Lys Val Ala Lys Phe Leu Leu Lys Glu
145                 150                 155
```

<210> SEQ ID NO 44
<211> LENGTH: 1133
<212> TYPE: DNA
<213> ORGANISM: Nannochloropsis sp.
<220> FEATURE:
<221> NAME/KEY: promoter
<222> LOCATION: (1)..(1133)

<400> SEQUENCE: 44

```
ggctgtgtta gttgttggaa gagggagggc aagtgctgct ggtactcctt ttgatggatg      60
ggcggggaga ctctggtcaa accgcacaca ccactcgctc tgccttgcct gctgcctgtg     120
tccgtgtgac agaagtgata ccagcgcgtg ttacttgagt gaagcgggag ttttgtggcc     180
aaaagaacgc gcggttgaat agaaatgggg gcgatgaccg gctgcggcca agcaaacctc     240
gagatatgac gaatgtacac gcaatggcaa tatatgatgc atatgccccc tagtgcaatg     300
aggcgtcgct tcgatgacta ctacgaccac attaccacac taaacggcac ctacccagtt     360
tgcgcgtagc gtaccatttt gtgtccgctt tgttcgcgtc ggcgcgctct acatatacta     420
```

-continued

| | |
|---|---|
| cgttgcatgt gttgcccgct ccatataaga tgatgagatg aataagaaga acaatacctc | 480 |
| ggcctgccgc ctgggcacgg gcaagcagaa caaacgaaaa aggcagtggc gtgcgcgatg | 540 |
| cctcaacctc tgtggcattt ttgggtgcat ccttgagtgg tacgcgtcgg ccgatgaaga | 600 |
| ctcaaagaag cagaggccac cgccgtcgtc tttgtacgga ttgttgctgc ggatgatggt | 660 |
| ggtccgccag atgctgccag gtggaacgct catgccctct ctctccgttc cctcctcacc | 720 |
| cggcacatgc tgacagaaga ggcgcacaca acacaggttg tcgggctgc actcctcgtc | 780 |
| actgcaacag ttgcgtcgct ttttggcctc ctgctgctgt cggcttgctt tcccatcgtg | 840 |
| tcccatctta ctacctcggt tgaatgccac agcccaccgg agcagatctc acagtactca | 900 |
| gtacacaaac aaaggacacg caacagcgca ccacatcgtg cagcgacacg gttcctatac | 960 |
| gcaggcaggc ctccatctgc gagttctgcc accttcaaat cgaattgcaa ctagtgtaag | 1020 |
| gtttaagcag ccttccttcc accatctcct ccacctcctc cttctcctca ccaccacgct | 1080 |
| catccaccgt cctcgcttca atcaatcttg gggaggaaag gagctacagc aag | 1133 |

<210> SEQ ID NO 45
<211> LENGTH: 1026
<212> TYPE: DNA
<213> ORGANISM: Nannochloropsis sp.
<220> FEATURE:
<221> NAME/KEY: promoter
<222> LOCATION: (1)..(1026)

<400> SEQUENCE: 45

| | |
|---|---|
| ccgtcgaggt ctatgaggac ggcagcgaca tcgcacaagc tgagatgtat agcatcattg | 60 |
| atgctgggta cgggtctttg cttgtactgt tctgcaacaa tggcaagctt accttgaact | 120 |
| acaactatgc cgcctaatga gagaacggga tgctgaataa tataattgaa tcaacggacc | 180 |
| agcttctcat tccaatctcc atgttttgc tgttatgtgt cgtgttgtgt tgcggggatg | 240 |
| tgagtgtctt atgtgtcgtg ttgtgttgcg gggatgtgtg tgtctctcgc ggcgtcctgt | 300 |
| taattctatt tctgcgcggg aatgtgagca tataattcag ggaccggtga gagcccggca | 360 |
| accccatcag aagccttgat ggatgaacaa tcagattgta acgagtggcg aagttgtgaa | 420 |
| agaattaaaa agaaggtgcc gaagatgaaa atttagctaa tgctttcttc cccccccccc | 480 |
| cagtttttt gggttttgt tcatagaaga tcaccgagcc atctgtaaga aggccataag | 540 |
| ccaccaagct gatgtttgct gggcgtgtag atatggatta tctcacagag tgacaggagt | 600 |
| ctgatatcaa gatagaggag tctcaagact tctggagatc gcacaccgtg tctcctcgca | 660 |
| agggatgcag tgttggccag cttctgtaga aaaggtgggc ataagttaag cacaatttgc | 720 |
| tgtcatcgtc gtaattgctg cttgtttcc tccgcacaac taaatcccac tgttacatag | 780 |
| taaatttcat gtccttttcc ccgttttgc acggtgttac attcgcgcca gattgccttc | 840 |
| atgaacgaat ccttgtgttc cgattctaaa atcaccaccc acccacccat cccaccacca | 900 |
| gaggcctcag agccccaacc acacgtgcta ggttactcaa tcatggtgtc gtccacaggt | 960 |
| tgtggatgtc gcatgggtga aaatgaccag gccgcgacct ccaccgcttc cacttggacg | 1020 |
| ccgatc | 1026 |

<210> SEQ ID NO 46
<211> LENGTH: 767
<212> TYPE: DNA
<213> ORGANISM: Nannochloropsis sp.
<220> FEATURE:
<221> NAME/KEY: promoter
<222> LOCATION: (1)..(767)

```
<400> SEQUENCE: 46
gtctctaaga tggagtggat ggaggaggag gcgagcgtag cagcaagcgt gagttataca      60
gccaggcaca tgtcgcaatc cttcggtctc gggcttaaaa tccacgcact aatcacgctg     120
ggccatgcaa agagcaatgc cgaggcccac cacacaaaac gctgtgtcgc gcgttgcggc     180
ctgaagcttc atacttctta gtcgccgcca aaagggctcg agagacgaga cccgttggca     240
tgaccgatgt tgttcgacgc ggtttgcttc gtcacagtcg acgtgattca ggaatctgga     300
gcctgcagat cattttttc agcctgatat cgttcttttc cactgagaac catcagacca     360
ccttttcttc cattgtgtga aggagtagga gttgccgtgc tgctttgtgg gagacatctg     420
cgatggtgac cagcctcccg tcgtctggtc gacgtgacga gcctcttcac tgttcttcga     480
cggagagacg caagcgagac ggctctagac cttttggaca cgcattctgt gtgtgaacta     540
gtggacagtg ataccacgtc tgaaagctca ccactgccca tggtgcagct acttgtcaca     600
aagttttgac tccgtcggta tcaccattcg cgctcgtgtg cctggttgtt ccgccacgcc     660
ggcctgcccc ggggcggggc aatattctaa aatctcacgc aaaacaccgc acttacccct     720
cacacatatt cgtgatagac caccaccaat ctcagcccgc atcaaca                   767

<210> SEQ ID NO 47
<211> LENGTH: 19
<212> TYPE: DNA
<213> ORGANISM: Artificial Sequence
<220> FEATURE:
<223> OTHER INFORMATION: Description of Artificial Sequence:primer

<400> SEQUENCE: 47
accttctaca acgagctgc                                                   19

<210> SEQ ID NO 48
<211> LENGTH: 22
<212> TYPE: DNA
<213> ORGANISM: Artificial Sequence
<220> FEATURE:
<223> OTHER INFORMATION: Description of Artificial Sequence:primer

<400> SEQUENCE: 48
gaacgtctca aacataatct gg                                               22

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence:primer

<400> SEQUENCE: 49
gttcgtgcag ttcagtgtgg                                                  20

<210> SEQ ID NO 50
<211> LENGTH: 17
<212> TYPE: DNA
<213> ORGANISM: Artificial Sequence
<220> FEATURE:
<223> OTHER INFORMATION: Description of Artificial Sequence:primer

<400> SEQUENCE: 50
cgggcagaat ccgaaca                                                     17
```